(12) United States Patent
Morris et al.

(10) Patent No.: US 7,422,586 B2
(45) Date of Patent: Sep. 9, 2008

(54) TISSUE SURFACE TREATMENT APPARATUS AND METHOD

(75) Inventors: David L. Morris, Sydney (AU); Steven A. Daniel, Fremont, CA (US); Daniel J. Balbierz, Redwood City, CA (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 09/797,409

(22) Filed: Feb. 28, 2001

(65) Prior Publication Data

US 2002/0120260 A1    Aug. 29, 2002

(51) Int. Cl.
*A61B 18/18* (2006.01)

(52) U.S. Cl. .......................................... 606/41; 607/101

(58) Field of Classification Search ................... 606/41, 606/42, 44–50, 32; 607/104, 105, 101, 102, 607/98, 115, 116
See application file for complete search history.

(56) References Cited

U.S. PATENT DOCUMENTS

| | | | | |
|---|---|---|---|---|
| 5,215,088 A * | 6/1993 | Normann et al. | ............ | 600/377 |
| 5,363,861 A * | 11/1994 | Edwards et al. | ............. | 600/585 |
| 5,370,675 A * | 12/1994 | Edwards et al. | ............. | 607/101 |
| 5,490,850 A | 2/1996 | Ellman et al. | | |
| 5,536,267 A * | 7/1996 | Edwards et al. | ................ | 606/41 |
| 5,697,281 A | 12/1997 | Eggers et al. | | |
| 5,697,909 A | 12/1997 | Eggers et al. | | |
| 5,888,198 A | 3/1999 | Eggers et al. | | |
| 6,077,257 A * | 6/2000 | Edwards et al. | ................ | 606/45 |
| 6,126,657 A | 10/2000 | Edwards et al. | | |
| 6,277,116 B1 * | 8/2001 | Utely et al. | .................... | 606/42 |
| 6,337,998 B1 | 1/2002 | Behl et al. | | |
| 6,358,273 B1 * | 3/2002 | Strul et al. | ..................... | 607/96 |
| 6,413,255 B1 * | 7/2002 | Stern | ........................... | 606/41 |
| 6,419,673 B1 | 7/2002 | Edwards et al. | | |
| 6,530,922 B2 | 3/2003 | Cosman et al. | | |
| 6,595,934 B1 | 7/2003 | Hissong et al. | | |
| 6,628,990 B1 * | 9/2003 | Habib et al. | ................. | 607/101 |
| 6,638,275 B1 | 10/2003 | McGaffigan et al. | | |
| 7,008,421 B2 * | 3/2006 | Daniel et al. | .................. | 606/50 |
| 7,223,264 B2 * | 5/2007 | Daniel et al. | .................. | 606/41 |

(Continued)

FOREIGN PATENT DOCUMENTS

WO    WO 03/005919    1/2003

*Primary Examiner*—Michael Peffley
(74) *Attorney, Agent, or Firm*—Abelman, Frayne & Schwab; Harry K. Ahn

(57) ABSTRACT

A tissue surface reatment apparatus includes a housing having a proximal end, a distal end including a tissue contacting surface, an interior defined by the housing and a handpiece coupled to the housing. The contactine surface has a plurality of apertures. An energy delivery device including an electrode is positionable in the housing interior. The electrode includes a tissue penetrating distal end in substantial alignment with an aperture. The electrode is configured to be advanced from the housing interior through the aperture and into a target tissue site to define an ablation volume at least partly bounded by a tissue surface. An advancement device is coupled to the energy deliveru device and is at least partly positionable within at least one of the housing or the handpiece. The advancement device is configured to advance the electrode fdro the housing interior into the target tissuesite and withdrawal the electrode into the housing interior. A cable is coupled to the housing or the energy delivery device and is configured to be coupled to an energy source.

23 Claims, 40 Drawing Sheets

U.S. PATENT DOCUMENTS

2002/0120261 A1    8/2002    Morris et al.
2002/0133149 A1    9/2002    Bessette
2003/0216726 A1    11/2003    Eggers et al.
2005/0137662 A1    6/2005    Morris et al.

\* cited by examiner

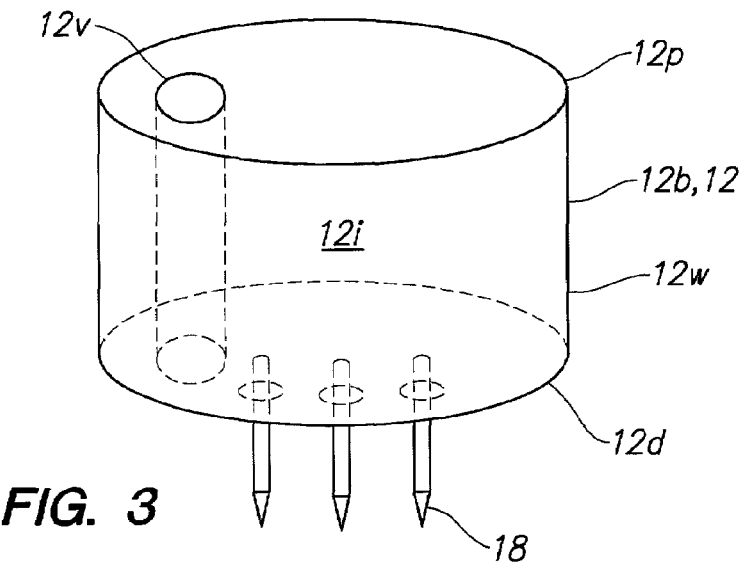
FIG. 3
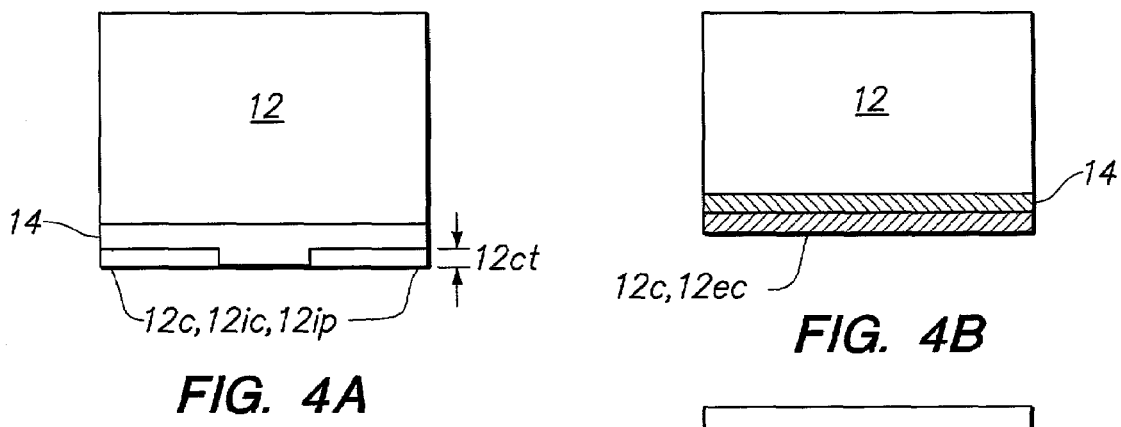
FIG. 4A
FIG. 4B
FIG. 4C
FIG. 4D
FIG. 4E

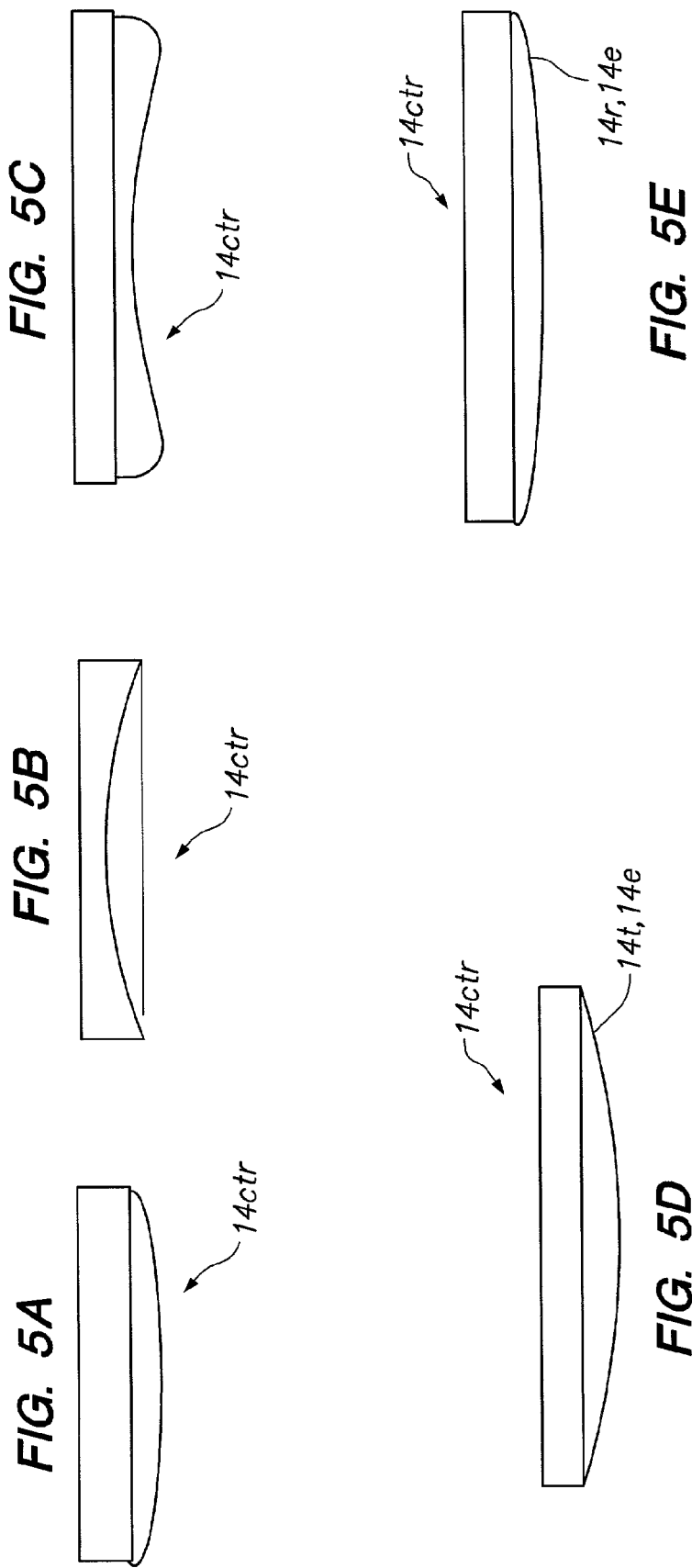

TISSUE SURFACE TREATMENT APPARATUS AND METHOD

BACKGROUND OF THE INVENTION

1. Field of the Invention

This invention relates generally to an apparatus and method for the minimally invasive treatment and ablation of tissue masses such as tumors, and more particularly to a tissue surface treatment apparatus with independently deployable electrodes configured to controllably ablate a tumor proximate or beneath a tissue surface.

2. Description of the Related Art

Standard surgical procedure, such as resection, for treating benign and malignant tumors of the liver and other organs have several key shortcomings affecting efficacy, morbidity and mortality. In an effort to fully remove or resect the tumor, the surgeon may be forced to remove or injure healthy tissue, compromising the function of the target organ. Further, the surgeon must exercise care in not cutting the tumor in a manner that creates seeding of the tumor, resulting in metastasis and spread of the disease. Also surgical resection procedures are contraindicated for instances of diffuse disease and/or small amounts of remaining healthy tissue.

Ablative treatment methods such as radio-frequency ablation, cryo-ablation, and microwave ablation have been employed as an alternative to resection to treat benign and malignant tumors in organs such as the prostate. However, these therapies in their present form have several critical drawbacks including: (i) inability to ablate/necrose the entire tumor; (ii) inability to ablate or necrose tissue along the entire length/perimeter of the tumor margin; (iii) inability to reduce lesion size sufficiently to reduce pain levels; (iv) inability to treat smaller tumors without potentially damaging surrounding healthy tissue and/or critical organs and structures; (v) inability of introducer to deploy device at an angle or otherwise access difficult to reach tumors; and (vi) inability to determine a meaningful clinical endpoint In particular tumors lying near or underneath an organ surface present a distinct set of problems to current ablative therapies. In order to superficially treat these type of tumors it is desirable for the physician to be able to deliver ablative treatment into the tumor, while avoiding all together or minimizing injury to critical anatomical structures that are adjacent and/or underneath the target tumor mass.

SUMMARY OF THE INVENTION

An embodiment of the invention provides a tissue surface treatment apparatus that includes a housing having a proximal end, a distal end including a tissue contacting surface and an interior defined by the housing. A hand piece is coupled to the housing. The tissue contacting surface has a plurality of apertures. An energy delivery device including at least one electrode is positionable in the housing interior. The at least one electrode includes a tissue penetrating distal end in substantial alignment with an aperture of the plurality of apertures. The at least one electrode is configured to be advanced from the housing interior through the aperture and into a target tissue site to define an ablation volume at least partly bounded by a tissue surface. An advancement device is coupled to the energy delivery device. The advancement device is at least partly positionable within at least one of the housing or the handpiece. The advancement device is configured to advance the at least one electrode from the housing interior into the target tissue site and completely withdraw the at least one electrode into the housing interior. A cable is coupled to one of the housing or the energy delivery device. The cable is configured to be coupled to an energy source.

Another embodiment of the invention includes a switching device coupled to at least one of the at least one electrode, a power supply coupled to the at least one electrode or a ground pad electrode coupled to the power supply. Impedance measurement circuitry is coupled to at least one of the at least one electrodes or the ground pad electrode. Logic resources are coupled to at least one of the impedance measurement circuitry or the switching device. The logic resources are configured to redirect at least a portion of a current flow going to the ground pad electrode responsive to an impedance change measured by the impedance measurement circuitry.

In still another embodiment, the energy delivery device includes a first electrode and a second electrode. The first electrode is deployable to a first depth and a second electrode is deployable to a second depth independent of the first depth.

In yet another embodiment, the handpiece includes a bendable or a curved portion. The bendable portion facilities access by the physician to difficult to reach areas of the liver such as a posterior portion or a portion adjacent or touching another anatomical structure.

In still another embodiment, the surface treatment apparatus includes a first RF electrode, a second RF electrode and a third RF electrode. Each of the first, second and third RF electrodes have a tissue piercing distal end and are positionable in the housing. The first and second RF electrodes are selectably deployable with curvature from the housing to a tissue site. The third RF electrode is deployable from the introducer with less curvature than the first and second RF electrodes.

Still yet another embodiment of the invention provides a tissue surface treatment apparatus that includes a housing having a proximal end, a distal end including a tissue contacting surface and interior defined by the housing. A handpiece is coupled to the housing. A fluid delivery device is positionable in the housing interior. The fluid delivery device includes at least one hollow non-conducting infusion member with at least one infusion aperture and a tissue penetrating distal end. The at least one infusion member is configured to be advanced from the housing interior and into a target tissue site to infuse a fluid into tissue and define a tissue infusion volume. The fluid delivery device is configured to be coupled to a fluid source. An advancement device is coupled to the fluid delivery device. The advancement device is at least partly positionable within at least one of the housing or the handpiece. The advancement device is configured to advance at least a portion of the at least one infusion member from the housing interior into the target tissue site and completely withdraw the at least one infusion member into the housing interior. A conductor is coupled to at least one of the fluid delivery device or the at least one infusion member. The conductor is configured to be coupled to an energy source.

BRIEF DESCRIPTION OF THE FIGURES

FIG. 3 is a lateral view illustrating an embodiment of the housing.

FIGS. 4a–4e are lateral views illustrating embodiments of the housing having various coatings.

FIGS. 5a–5e are lateral views of the tissue-contacting surface illustrating various contours of the surface as well as the shape of the surface edge including radiused and tapered edges

FIG. 15d is a lateral view illustrating an embodiment of the tissue contact surface having tissue access ports.

FIGS. 23a–23h are lateral views illustrating various configurations of the electrode including ring-like, ball, hemispherical, cylindrical, conical and needle-like.

FIG. 38b is a lateral view illustrating the spacing between electrode rows for the embodiment of FIG. 38a.

FIG. 44a shows an embodiment with a single positive and negative electrode. FIG. 44b shows a multiple positive electrodes in a circular pattern with a centrally located return electrode. FIG. 44c shows an arc shaped pattern of positive electrodes with a single return electrode.

DETAILED DESCRIPTION

In order to superficially treat organ tumors (e.g. hepatic tumors), particularly those near the tissue surface it is desirable for the physician to be able to deploy electrodes into the tumor while avoiding and minimizing injury to adjacent critical anatomical structures that are adjacent and underneath the target tumor mass.

The present invention provides an apparatus and method to address this and other need in performing surface treatment of tissue masses and tumors such as liver tumors using both open chest procedures and minimally invasive procedures. In particular, embodiments of the invention are configured to selectively deploy individual electrodes or an array of electrodes into a tumor or tissue mass so as to achieve a particular pattern to precisely treat the tumor while avoiding adjacent critical anatomical structures such as vasculature (e.g. hepatic veins) and nerve plexi. Further, the apparatus of the present invention allows the electrodes to be deployed to a selective depth again to solve the problem of deploying electrodes into the tumor mass while avoiding deeper healthy tissue. In a preferred embodiment, the electrodes are deployable to a depth of 1.5 cm.

Also, various embodiments are configured to treat not only accessible anterior portions of the liver but also posterior portions and/or portions obstructed by overlying or adjacent tissue and other organs and tissue. This capability is achieved through the use of components with sufficient flexibility and resiliency to bend, curve around or conform to tissue and anatomical structures including organs, bone and vasculature. Components of the apparatus of the invention having this flexibility can include the handpiece, housing and tissue contact surface described in detail herein. This flexibility enables the apparatus to not only be readily manipulated and positioned in at least partially obstructed tissue but also to deliver energy, fluids and apply pressure to and on obstructed or otherwise difficult to reach target tissue sites.

Figure 1:
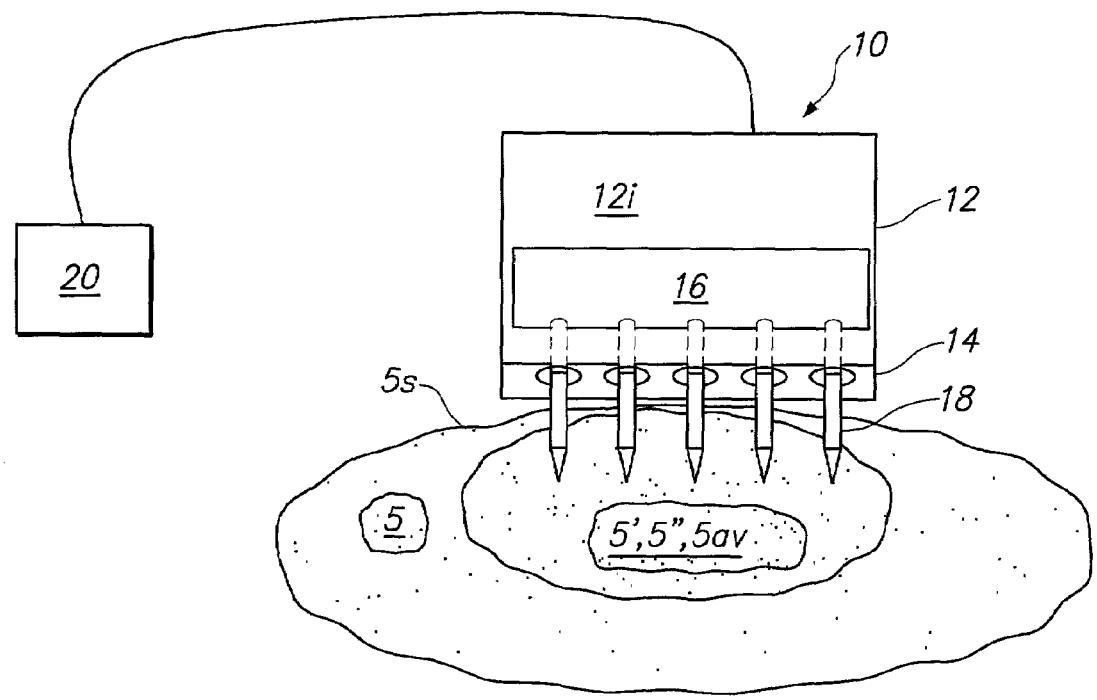
FIG. 1 is a lateral view illustrating the placement of a surface treatment apparatus to treat a tissue mass at or beneath a tissue surface in an embodiment of the method of the present invention.
Figure 2:
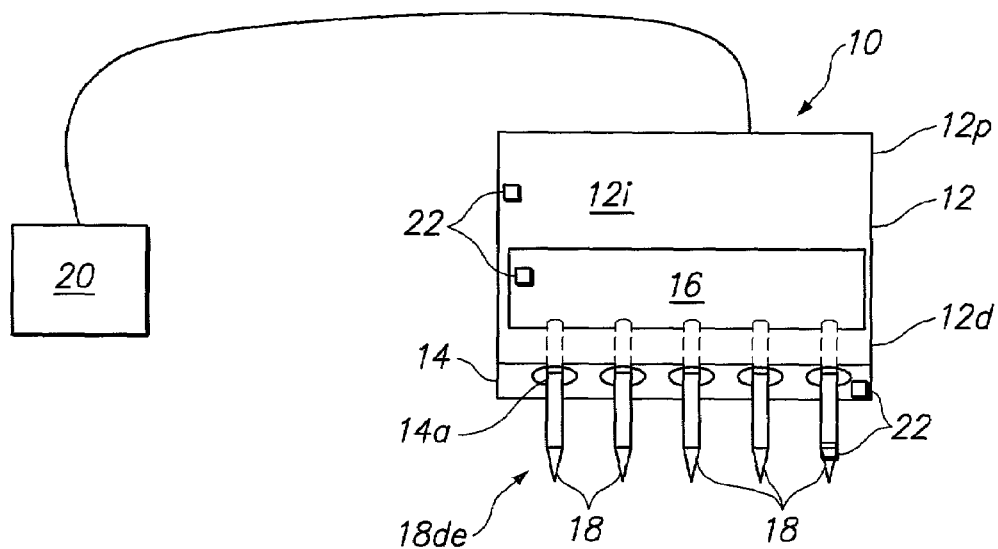
FIG. 2 is a lateral view illustrating the components of an embodiment of a surface treatment apparatus including the housing, tissue contacting surface, energy delivery device and advancement member.

Referring to FIGS. 1 and 2, FIG. 1 shows an embodiment of surface treatment apparatus 10 to superficially treat a tumor mass 5" in a target tissue site 5' at or beneath the surface 5*s* of tissue 5 by delivering energy to produce an ablation volume 5*av*. As shown in FIG. 2 apparatus 10 includes a housing 12 that has a proximal and distal portion 12*p* and 12*d* and an interior space 12*i*. All or a portion of housing 12 can be configured to contact a tissue surface 5*s* at a target tissue site 5'. In an embodiment housing 12 includes a tissue contacting surface 14 positioned at distal portion 12*d*. Tissue contacting surface 14 can have one or more apertures 14*a*. An electrode advancement member 16 is positionable within the housing and coupled to one or more energy delivery devices 18. The energy delivery devices 18 can have distal ends 18*de* sufficiently sharp to penetrate tissue electrodes. Energy delivery devices 18 are positionable within the housing 12 and configured to be advanced out of the apertures 14*a* into tissue to a target tissue site 5'. Energy delivery device 18 can be configured to be coupled to an energy or power source 20. A sensor 22 may be coupled to energy delivery device 18, as well as housing 12 including tissue contacting surface 14. Sensors 22 can be configured to measure temperature, impedance or other physical properties of the housing, energy delivery device and adjacent tissue.

A variety of energy delivery devices and power sources can be utilized by embodiments of the invention. Specific energy delivery devices 18 and power sources 20 that can be employed in one or more embodiments include, but are not limited to, the following: (i) a microwave power source coupled to a microwave antenna providing microwave energy in the frequency range from about 915 MHz to about 2.45 GHz; (ii) a radio-frequency (RF) power source coupled to an RF electrode; (iii) a coherent light source coupled to an optical fiber or light pipe; (iv) an incoherent light source coupled to an optical fiber; (v) a heated fluid coupled to a catheter with a closed or at least partially open lumen configured to receive the heated fluid; (vi) a cooled fluid coupled to a catheter with a closed or at least partially open lumen configured to receive the cooled fluid; (viii) a cryogenic fluid; (ix) a resistive heating source coupled to a conductive wire; (x) an ultrasound power source coupled to an ultrasound emitter, wherein the ultrasound power source produces ultrasound energy in the range of about 300 KHZ to about 3 GHz; and (xi) combinations thereof. For ease of discussion for the remainder of this application, the energy delivery device 18 is one or more RF electrodes 18 and the power source utilized is an RF power supply. However all energy devices and sources discussed herein are equally applicable.

Housing 12 can have a variety of shapes including rectangular, circular, oval and pyramidal. Referring to FIG. 3, in a preferred embodiment housing 12 has a cylindrical shape, in which the proximal and distal ends 12*p* and 12*d* comprise the two ends of the cylinder with a wall 12*w*. Ends 12*p* and 12*d* can be fixedly attached to the body of the cylinder 12*b* or can be movable therein which can include sliding and reciprocal movement. Housing 12 can be fabricated from a variety of polymers known in the art including rigid polymers, including but not limited to polycarbonate, acrylic, polyester, ABS and combinations thereof using injection molding or rim methods known in the art. Also housing 12 can be machined from both plastics and metals such as aluminum, stainless steel and the like, using machining methods known in the art. Housing 12 can also be made from flexible metals such as or from compliant or resilient polymers that enable housing 12 to be flexible in one or more directions. Examples of flexible metals include, but are not limited to, nickel titanium alloys. Examples of resilient polymers include, but are not limited to, elastomers including silicone, polyurethane, PEBAX® and combinations thereof. Flexibility of housing 12 can also be achieved through the use of an accordion or bellow construction of housing walls 12w. Also, in an embodiment all or portions of housing 12 can have transparent portions or viewing ports 12v made of transparent polymers such as polycarbonate so as to enable the physician to observe the tissue contacted by the housing as well as the position and advancement of the energy delivery devices there into. In use, this embodiment not only allows the physician to observe the tissue during placement of the housing 12, but also during the delivery of thermal energy to tissue site 5″ and thus observe tissue blanching and other color changes indicative of the size of the developing ablation volume.

Referring to FIGS. 4a–4e, in various embodiments all or a portion of housing 12, including tissue contacting surface 14 can have a coating 12c which can be an insulative coating 12ic, an electrical conductive coating 12ec, a lubricous coatings 12lc or a thermally reflective coating 12tr. These and other coatings can be applied using dip coating, spray coating, electro-deposition, plasma coating, lithographic and other coating methods known in the art.

For purposes of this application, an insulative coating is defined to be both an electrical and a thermal insulative coating. In a preferred embodiment, tissue contact surface 14 has an insulative coating 12ic that insulates against the transmission of RF energy. Coating 12ic can be made from electrically and thermally insulative polymers known in the art including, but not limited to, polyamide, polyamide fluorocarbons, PTFE and TEFLON®. Such coatings can range in thickness 12ct from 0.0001 to 0.1 inches with a preferred embodiment of 0.001 to 0.003 inches. Also in an embodiment, coating 12ic can be a peelable coating so as to be detachable or movable on housing 12, enabling the user to create a selectable insulative portion 12ip. Coating 12ic can be configured to be peelable and re-attachable using re-attachable, low strength adhesives known in the art.

In a related embodiment, coating 12c can be a non-stick or lubricous coating 12ic configured to keep surface 14 or other portion of housing 12 or energy delivery 18 from sticking to tissue surface 5s before during or after ablation. This solves the problem of coagulated or burnt tissue undesirably sticking to surface 14 preventing its removal and/or causing unwanted tearing and other trauma to tissue surface 5s or tissue 5. Such coatings can include PTFE, TEFLON® and other fluorocarbon polymers, silicones, paralene and other low surface tension non-stick coatings known in the art.

In another embodiment, coating 12c can be a thermally reflective coating 12trc. Examples of thermal reflective coating include metal coatings such as aluminum coating, silver coating, alloys thereof and the like. In use thermal reflective coating 12trc on contact surface 14 serves to reflect radiated heat back into the tissue surface at the target site 5' and thereby increase the rate of heating of the tissue site 5' including tissue mass 5″ resulting in faster and larger ablation volumes with less delivered power.

In still another embodiment coating 12c can be a textured coating 12tc configured to increase the coefficient of friction with tissue surface 5s. In use, this serves to stabilize contact surface 14 on tissue surface 5s and/or reduce movement of contact surface. Suitable coatings and patterns can include high friction polyurethane-polyether or polyester polymer coatings carbide coatings, knurled and diamond pattern coatings and the like known in the art.

Turning now to a discussion of the tissue contacting surface 14 (also called tissue contact surface 14), this component can have a variety of shapes including but not limited to circular, oval, rectangular, square and combinations thereof. Referring now to FIGS. 5a to 5e, contact surface 14 can have a variety of contours 14ctr including curved contours including convex or concave curved contours and combinations thereof. Additionally, the edges 14e of contacting portion 14 can be tapered 14t or radiused 14r.

Figure 6:
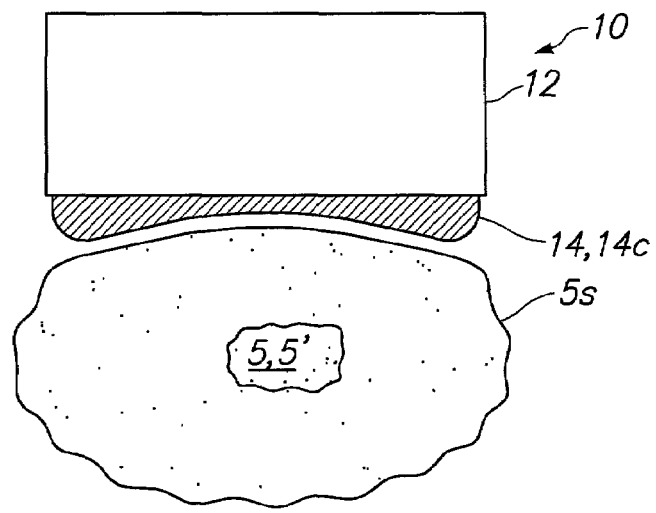
FIG. 6 is lateral view illustrating placement and use of an embodiment of the invention having a conformable tissue surface.

Referring to FIG. 6, in various embodiments all or a portion of the tissue contact surface 14 can be a conformable surface 14c that conforms or bends to the shape of tissue surface 5s. This can be accomplished by constructing all or a portion of surface 14 from resilient polymers including but not limited to elastomers such as silicone and polyurethane and polymers thereof as wells as foam rubber. Surface 14c can be fabricated from such materials using injection molding or mandrel dip coating methods known in the art.

In use, a conformable or movable surface solves the problem of assuring and maintaining contact with an uneven or obstructed tissue surface before, during or after the ablation without causing undesired tissue trauma. In a related embodiment, a conformable surface 14c can also be coupled to a deflecting mechanism described herein to allow the physician to remotely deflect or shape contact surface 14 to a shape that at least partially matches that of a selected target tissue surface 5s or otherwise facilitates positioning of surface 14 on target tissue surface 5s. This embodiment solves the problem of allowing the physician to position surface 14 when the target tissue surface 5s is obstructed by tissue and anatomical structures or is otherwise in a difficult position to reach.

Figure 7A:
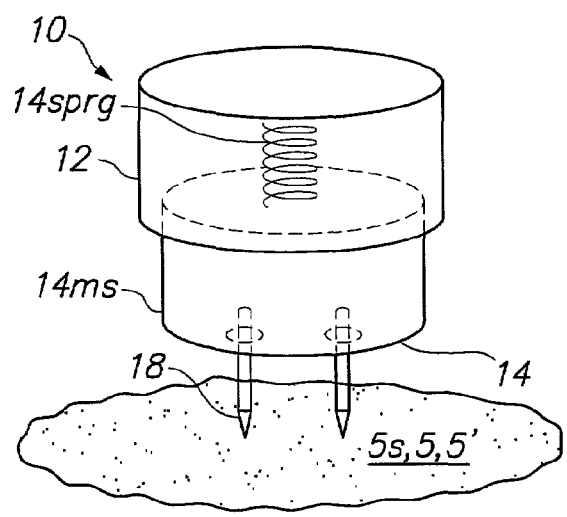
FIGS. 7a and 7b are perspective views illustrating an embodiment of a movable tissue contacting surface.
Figure 7B:
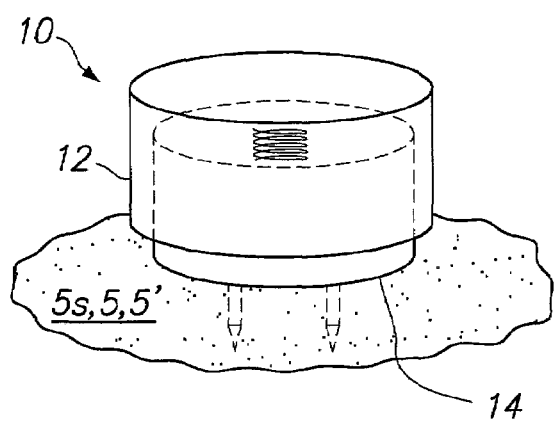

Referring to FIGS. 7a and 7b, in another embodiment the tissue contacting surface 14 is movable (longitudinally or otherwise) in response to force applied by the tissue surface onto the tissue surface 14. This can be achieved through a variety of known spring mechanisms including constructing surface 14 on a movable cylinder or sleeve 14ms which can travel under or over housing 12 and then positioning and coupling one or more compressed coiled springs 14sprg to and between the surface 14 and housing 12. This embodiment solves the problem of assuring and maintaining contact with the tissue surface before, during or after the ablation without causing undesired tissue trauma due to the application of excessive force to the tissue.

Figure 8:
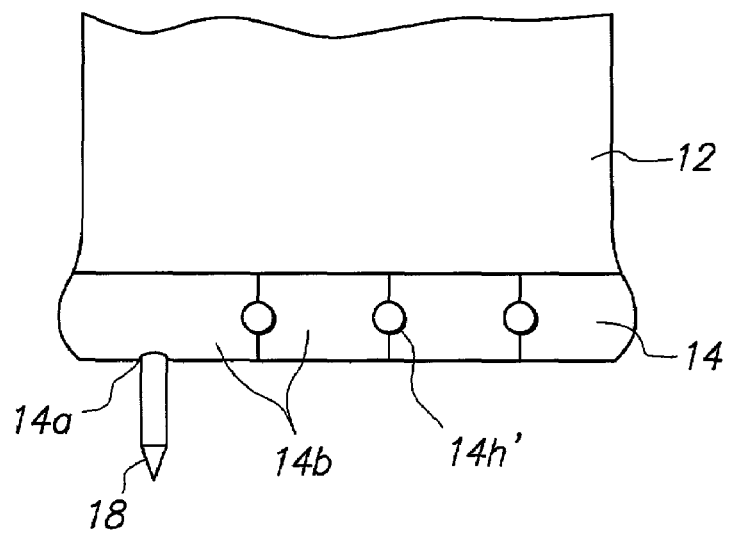
FIG. 8 is a lateral view illustrating an embodiment of a bendable tissue contacting surface with hinged sections.
Figure 9A:
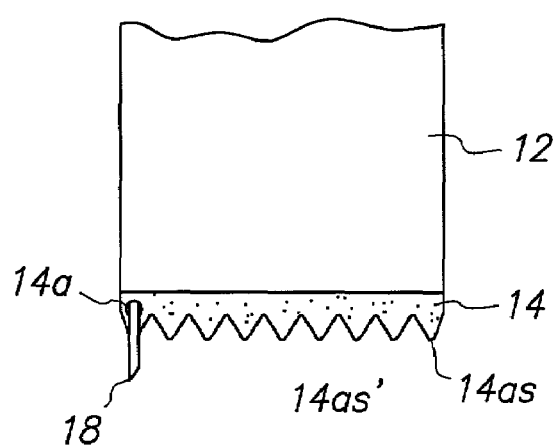
FIGS. 9a and 9b are lateral and bottom views illustrating an embodiment of a bendable tissue contacting surface with articulated sections.
Figure 9B:
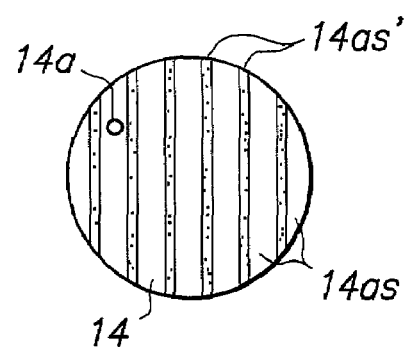
Figure 10:
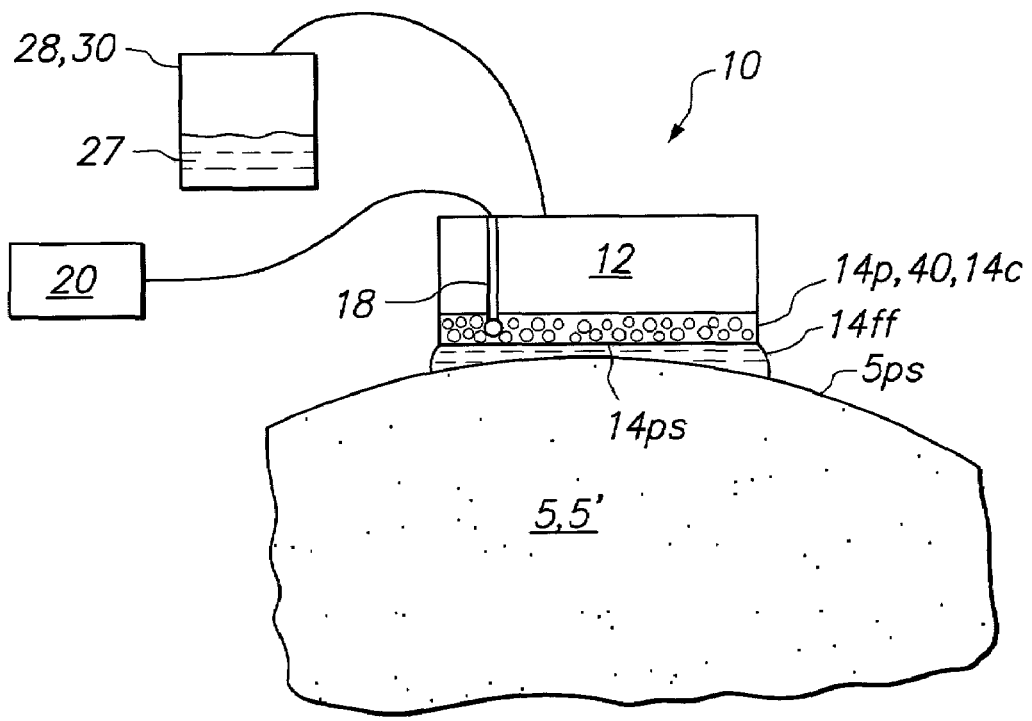
FIG. 10 is a lateral view illustrating an embodiment of a porous tissue contacting surface including delivery of a fluid film.

Referring to FIGS. 8, 9a and 9b in other embodiments surface 14 can comprise one or more bendable sections 14b. In an embodiment shown in FIG. 8, bendable sections 14b can include hinges 14h' to allow surface 14 to be moved and shaped by the physician prior to or during application of surface 14 to the target tissue surface. The hinges 14h' used can include those known in the art including spring loaded hinges giving the bendable sections 14b shape resilience. Hinges 14h' can also include bearings, roller bearings, and miniature bearings such as those manufactured by RMB Miniature Bearings (Biel-Bienne, Switzerland). In a related embodiment shown in FIGS. 9a and 9b, all or portion of surface 14 can include articulated sections 14as fabricated using known methods of articulated construction such as use of corrugated sections made using molding methods known in the art. Articulated sections 14*as* have a sufficient number of articulations 14*as*' to allow robust movement of surface 14 in one or more directions. Articulated sections 14*as* can be configured to bend or deflect with a selectable amount of applied force which can be in the range of 0.01 to 2 lb with specific embodiment of 0.05, 0.1, 0.25, 0.5 and 1 lb of force.

Referring to FIGS. 10–14, in various embodiments, all or a portion of surface 14 including conformable surface 14*c* can be constructed from a porous material fluidly coupled to a fluid source and/or fluid delivery device described herein. In an embodiment shown in FIG. 10, a porous portion or section 14*p* of surface 14 is configured to deliver a fluid film 14*ff* to target tissue surface 5*s*. Porous portion 14*p* can be made from a porous membrane or other porous material. Suitable porous materials can include but are not limited to foam, foam rubber, polyurethane foam, cellulose and woven or knitted DACRON, knitted polyester, continuous filament polyester, polyester-cellulose, rayon, polyamide, polyurethane, polyethylene and the like. The delivery of a fluid film in this manner can be configured to perform one or more of the following functions: (i) produce a virtual fluid electrode adjacent or in the tissue surface to uniformly deliver RF energy to the selected tissue surface and underlying tissue when using a conductive solution; (ii) produce a virtual and electrically uniform ground pad electrode on the selected tissue surface to act as a return path for RF energy when using a conductive solution; and (iii) provide cooling over the selected tissue surface when a cooling solution is used which can also be a conductive solution. Porous surface 14*ps* can have selectable and/or variable amounts of porosity. In one embodiment, porous portion 14*p* has uniform porosity and thickness so as to be able to achieve a substantially uniform delivery of fluid over porous portion surface 14*ps*. In another embodiment the porosity is varied over portion 14*p* including surface 14*ps* to produce varying amounts of fluid flow. For example, higher porosity on the perimeter to produce greater flows on the perimeter or edges of section 14*p* or alternatively greater porosities in the center portion. Also the porosity of section 14*p* can be controlled to retain fluid within the interior of section 14*p* in order to have section 14*p* act as a virtual or enhanced electrode 40 (described here in) including a virtual flexible electrode. Alternatively, one or more RF electrodes, such as plate or ring shaped RF electrodes 18, may be positioned within section 14*p* to both cool the electrode and conduct RF energy to section 14*p* to allow section 14*p* to act as an RF electrode to deliver RF energy to tissue surface 5*s* and underlying tissue.

Figure 11:
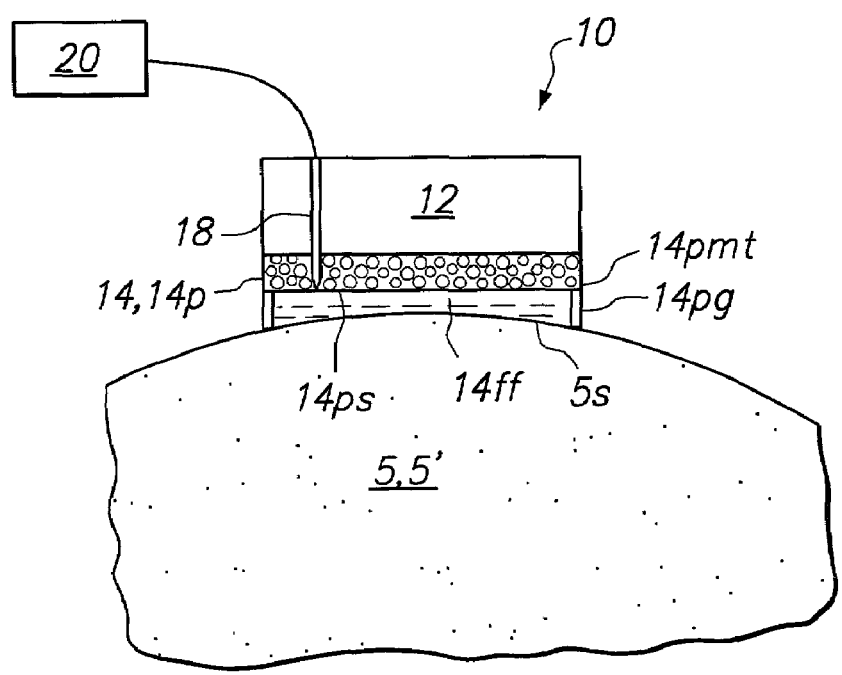
FIG. 11 is a lateral view illustrating an embodiment of a porous tissue contacting surface including a flexible lip.

As shown in FIG. 11, porous section 14*p* can include a flexible lip or gasket section 14*pg* to trap or otherwise contain the fluid film between contact surface 14 and tissue surface 5*s*. Gasket section 14*pg* can be made out of resilient polymers including elastomers such as silicone and can be located anywhere along surface 14 including all or a portion of the perimeter 14*pmt* of contact surface 14.

Figure 12A:
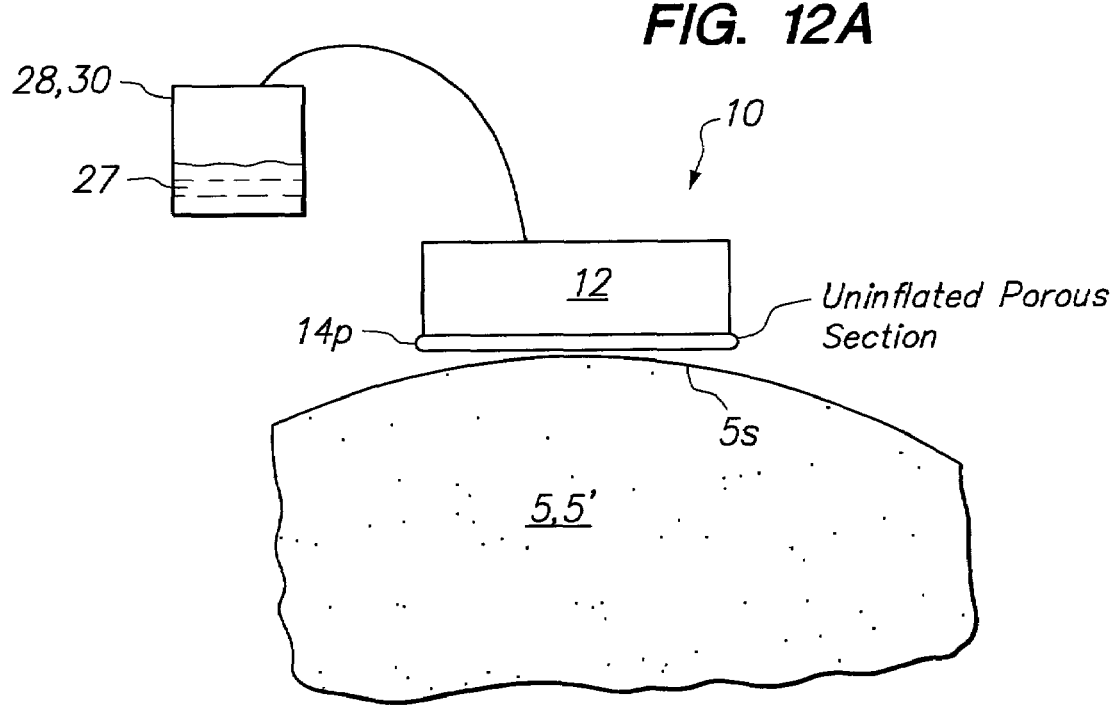
FIGS. 12a and 12b are lateral views illustrating use of an inflatable porous tissue contacting surface.
Figure 12B:
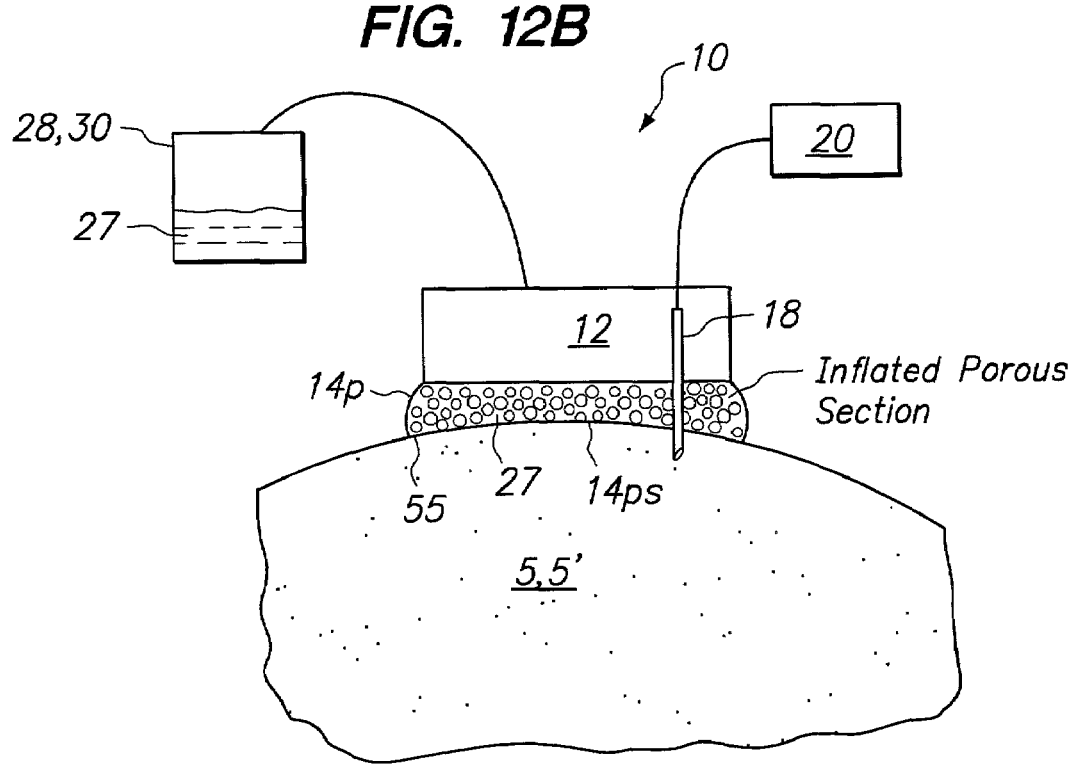

As shown in FIGS. 12*a* and 12*b*, in related embodiments the porosity of porous portions 14*p* can be used to control the flexibility stiffness of surface 14 by retaining greater or lesser amounts of fluid within section 14*p* to control its hydrostatic pressure (when the surface is coupled to a pressurized fluid delivery device such as an IV pump) and effectively inflate or deflate the section 14*p* (similar to an inflatable balloon) to a desired stiffness and shape. This can also be done by controlling the fluid pressure of the fluid delivery device 28 or fluid source 30 coupled to porous section 14*p*. Shape and conformability of porous surface 14*p* can also be controlled by controlling the viscoelasticity of the inflationary media/fluid 27. In an embodiment, the inflation media 27 can be a viscoelastic gel such as a silicone gel or a conductive gel such as a carboxymethylcellulose gel mixed with saline solution. The viscosity of inflation media 27 can range between 1–100 centipoise with specific embodiments of 5, 10, 25, 50 and 75 centipoise. In an embodiment shown in FIG. 12*b*, the viscosity of solution 27 can be sufficient to form a substantial fluidic seal around a protruding electrode 18.

Figure 13A:
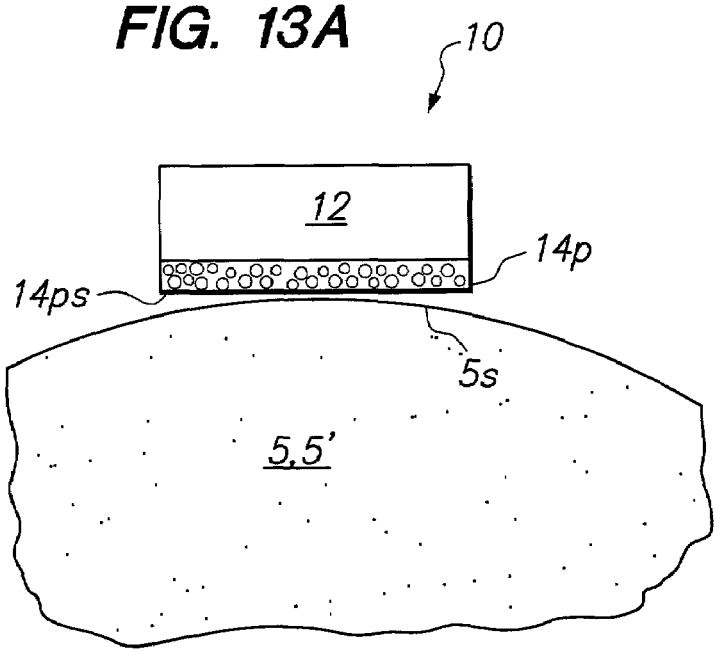
FIGS. 13a and 13b are lateral views illustrating use of a vacuum source coupled to porous tissue contacting surface.
Figure 13B:
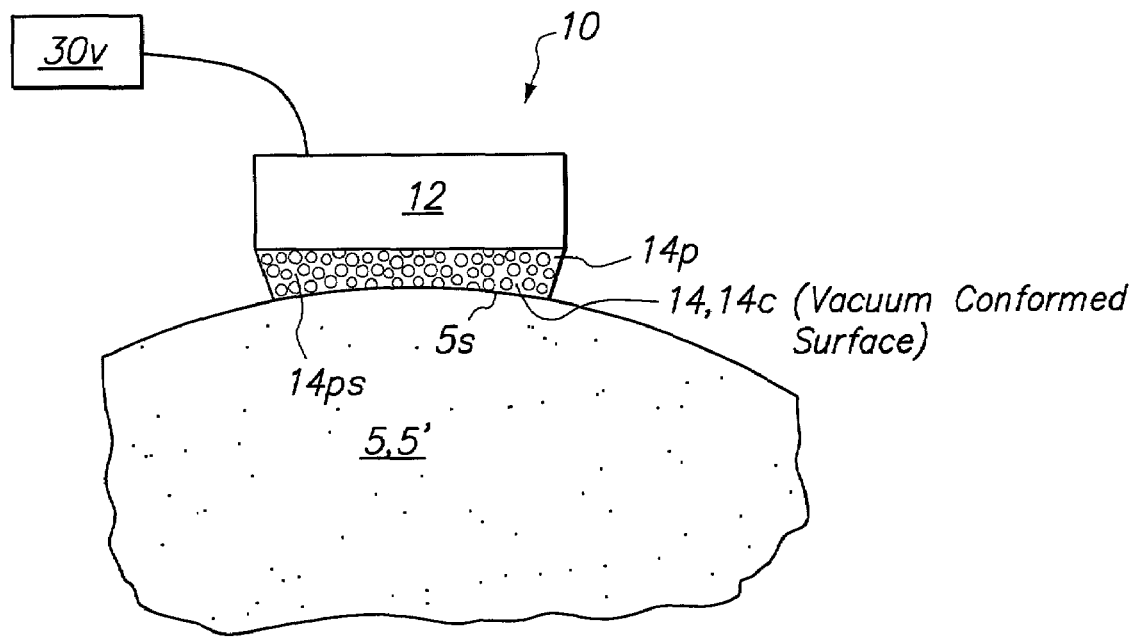

As shown in FIGS. 13*a* and 13*b*, in another embodiment porous portion 14*p* can also be configured to deliver a vacuum to between tissue contact surface 14 and tissue surface 5*s*. This can be achieved by coupling portion 14*p* and apparatus 10 to a vacuum source 30*v* known in the medical equipment art. The generation of a vacuum at tissue contact surface 14 via portion 14*p* or other means can provide one or more of the following benefits: (i) rapidly get all or portions of contact surface 14 to conform to the shape of tissue 5*s*, which is particularly beneficial when access to apparatus 10 and tissue surface 14 is limited or obstructed (e.g. when surface 14 is placed on the posterior side or otherwise underneath the liver); and (ii) provide sufficient vacuum to stabilize or even fixedly attached contact surface 14 onto tissue surface 5*s* to prevent undesired movement of housing 12 and surface 14 during electrode deployment, respiration, involuntary muscle contraction, or inadvertent jarring during the medical procedure.

Figure 14:
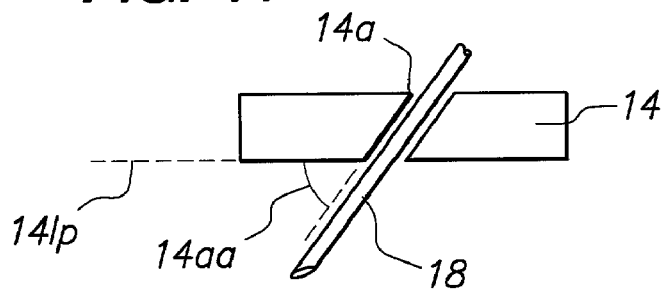
FIG. 14 is a lateral view illustrating the angle of an aperture positioned in the housing for purposes of electrode advancement in an embodiment of the invention.

Referring to FIG. 14, apertures 14*a* in surface 14 can be configured to have a selectable angle, 14*aa* with respect to a longitudinal plane 14*lp* of tissue contact surface 14 such that electrode 18 exists the aperture and enters into tissue at that angle. Angle 14*aa* can be in the range of 1 to 180° with specific embodiments of 30, 45, 60, 90, 120 and 135°.

Figure 15A:
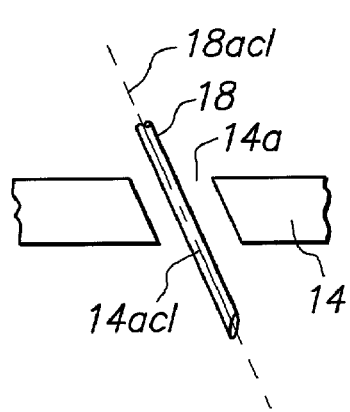
FIGS. 15a–15d are lateral views illustrating various alignments for the aperture and electrodes of the embodiment in FIG. 14.
Figure 15B:
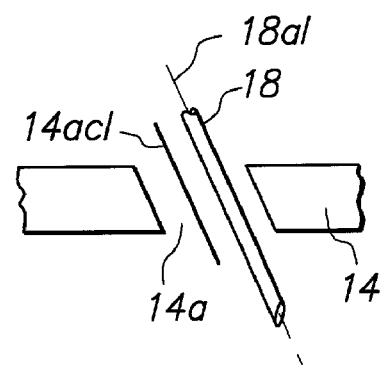
Figure 15C:
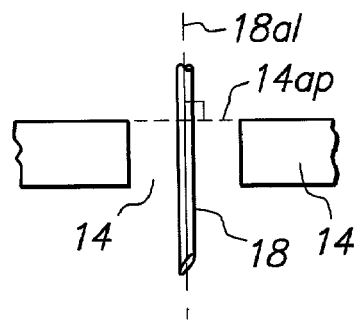

Referring to FIGS. 15*a*–15*c*, in various embodiments aperture 14*a* and electrode 18 can have different alignments including but not limited to the following: (i) aperture centerline 14*acl* aligned with the centerline axis 18*acl* of electrode 18; (ii) aperture centerline axis 14*acl* substantially parallel with the electrode longitudinal axis 18*al*; and (iii) electrode longitudinal axis 18*al* substantially perpendicular to aperture plane 14*ap*.

Figure 15D:
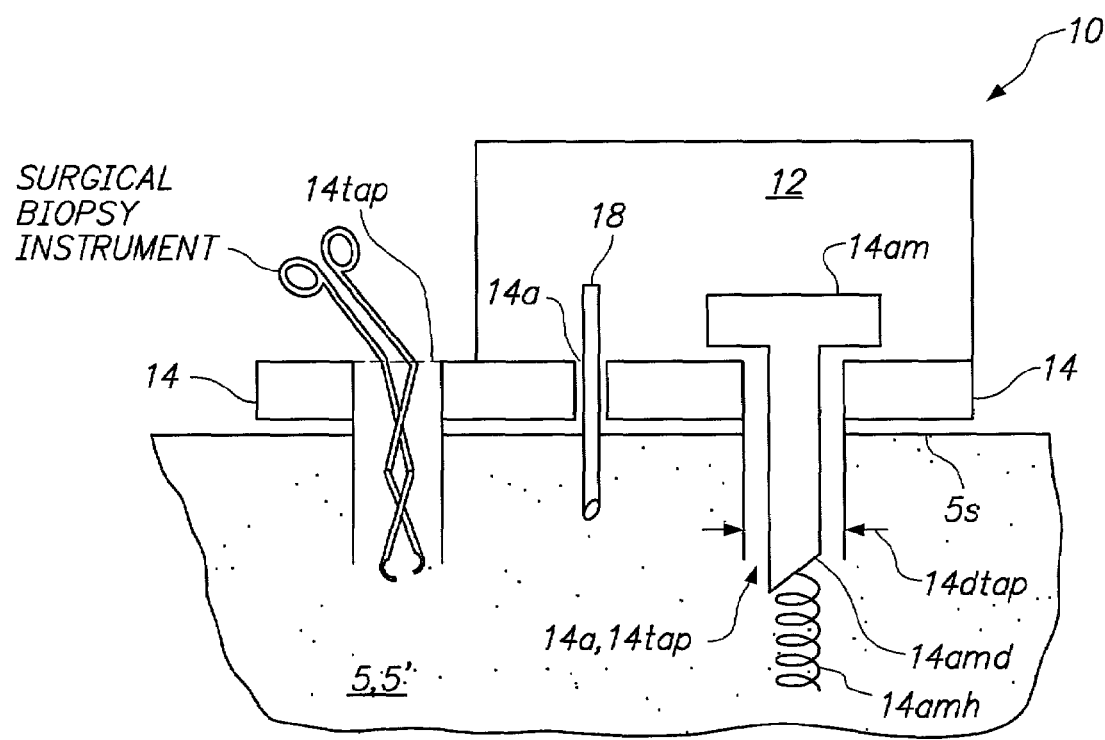

Referring to FIG. 15*d*, in various embodiments tissue contact surface 14, including housing 12, can include one or more tissue access ports 14*tap* or access ports 14*ap* that are distributed in one or more locations in surface 14 which can be the same as or distinct from apertures 14*a*. Access ports 14*tap*, and 14*ap* can have sufficient diameter to allow access by various surgical instruments including trocars, scalpels, hemostats, biopsy needles and surgical scissors. The diameter 14*dtap* of port 14 *tap*, 14*ap* can range from 0.1 to 1" with specific embodiments of 0.25, 0.5 and 0.75 inches. Also, access port 14 *tap*, 14*ap* can be covered with transparent covers. In use, access ports 14 *tap*, 14*ap* are configured to allow the physician access to tissue surface 5*s* and underlying tissue to in order to obtain biopsies, insert surgical instruments, do resections and other surgical procedures. Access ports 14 *tap*, 14*ap* can also be configured to provide an anchoring function for contact surface 14 and housing 12. To this end, access ports 14 *tap*, 14*ap* can include or coupled to an anchoring member 14*am* which extends from the access port to a selectable depth in tissue. Anchoring member 14*am* can have a sharpened distal tip 14*amd* that can be a trocar or other needle shape known in the art or described herein. In use, anchoring member 14*am* serves to stabilize and anchor housing 12 and tissue contact surface 14 to tissue surface 5*s*. In an embodiment, anchoring member 14*am* can have a helical or corkscrew shape 14*amh* which can be screwed into tissue including fibrous tissue and encapsulated tissue. In a related embodiment, one or more electrodes 18 can also have a helical shape to provide an anchoring function as well.

Turning now to a discussion of advancement member 16, this component is configured to controllably advance energy electrodes 18 from the interior 12*i* of housing 12 into tissue at the target tissue site. Advancement member 16 can be freely moving within the interior of housing 12 with movement including reciprocal linear motion, axial motion, lateral motions, rotary motion and combinations thereof. Advancement member 16 can also be at least partially positionable in a handpiece 24(described herein) coupled to housing 12.

Figure 16:
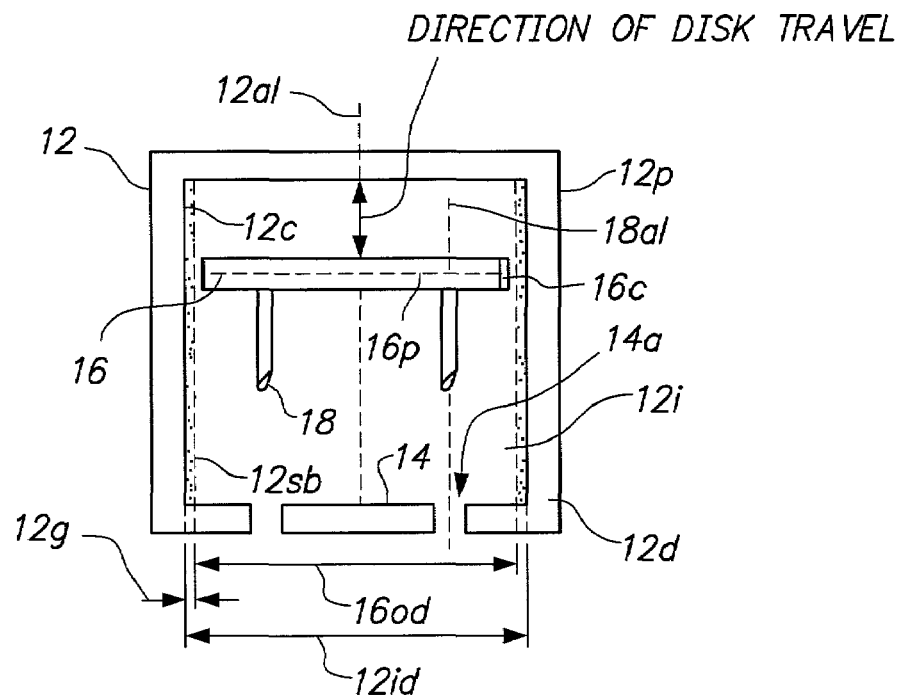
FIG. 16 is a lateral view illustrating the configuration and use of an embodiment of a disk-shaped advancement member.

In an embodiment shown in FIG. 16, advancement member 16 comprises a disk parallel to proximal or distal end 12*p* or 12*d*, coupled or attached to one or more electrodes 18 that preferably have an longitudinal axis 18*al* perpendicular to the surface plane 16*p* of advancement device 16. Disk 16 can be configured to move within housing interior 12*i* in a reciprocal fashion with respect to the longitudinal axis 12*al* of housing 12. The movement can be slidable, rotational or a combination thereof. This is achieved by selecting the outer disk 16*od* to be slightly less than the internal housing diameter 12*id*. The resulting gap 12*g* between the two can be in the range of 0.001 to 0.010 with preferred embodiments of 0.003 and 0.005 inches. Motion between the two can also be facilitate through use of a lubricous coating 12*c* or 16*c* on one or both of the contacting surfaces of housing 12 or disk 16. Alternatively a sleeve bearing or insert 12*sb* can be placed within the contact surface of housing interior 12*i*. Sleeve bearing 12*sb* can have shape and materials known in the art.

Figure 17:
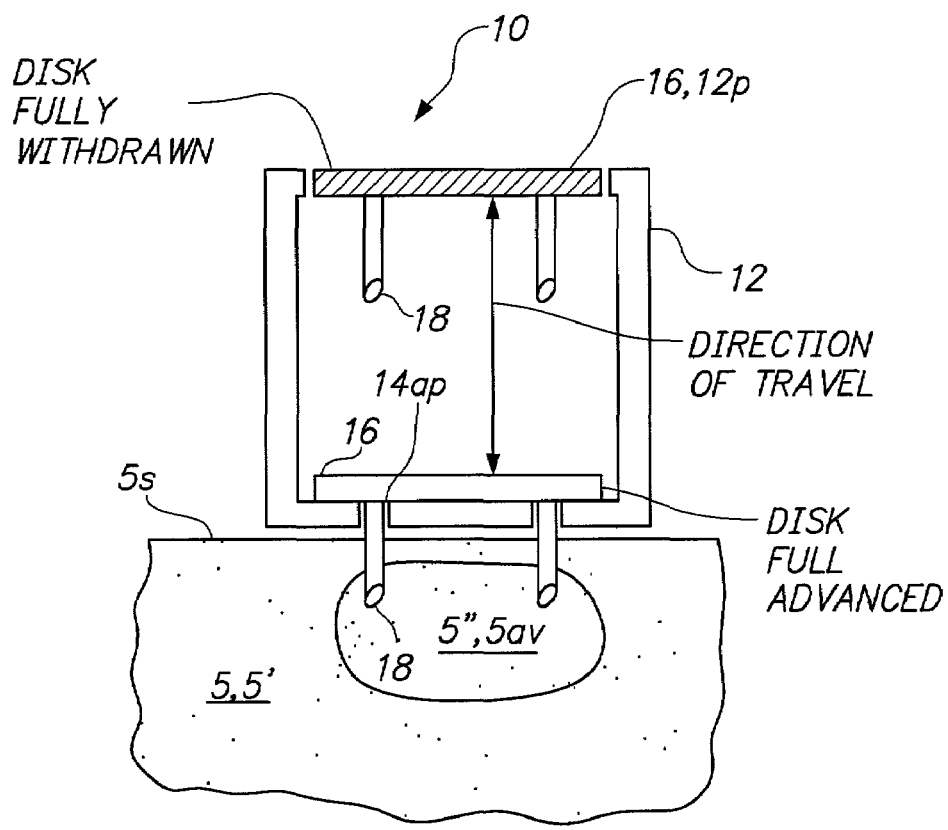
FIG. 17 is a lateral view of an embodiment of a disk-shaped advancement member integral to the housing.

In an embodiment shown in FIG. 17, member 16 which can be disk shaped or another shape, can comprise all or a portion of proximal end 12*p* of housing 12, thus making proximal end 12*p* movably coupled to housing interior 12*i*. In this and related embodiments, movable proximal end 12*p* can be configured to move or slide reciprocally within in housing 12.

Figure 18:
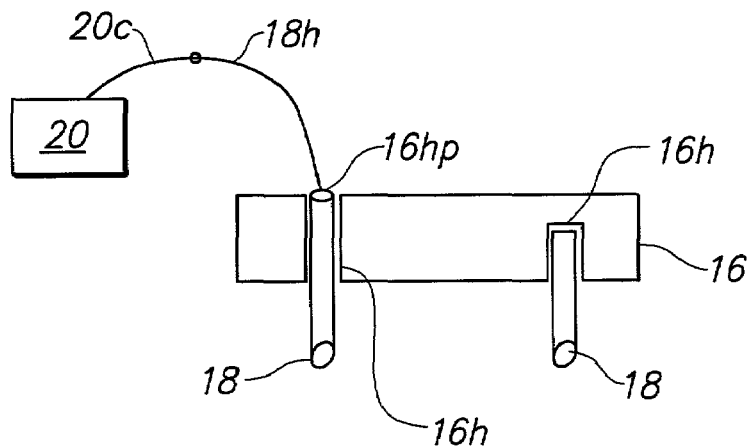
FIG. 18 is a cross sectional view illustrating the placement of electrodes with the advancement member.

Referring to FIG. 18, electrodes 18 can be positioned in holes 16*h* formed or drilled in disk surface 16*s* and then subsequently adhered in place using adhesive known in the art including but not limited to medical grade including medical grade adhesives such as medical grade epoxies. Also the fit between electrode 18 and hold 16*h* can be an interference fit or within 0.001 to 0.005 of an inch. Hole 16*h* can be a through or a blind hole. Preferably hole 16*h* has a proximal opening 16*hp* to allow a wire 18*h* to be electrically coupled (e.g. by soldering) to each electrode. Wire 18*h* either then is coupled directly to power source 20 or to a cable 20*c* electronically coupled to power source 20.

Figure 19:
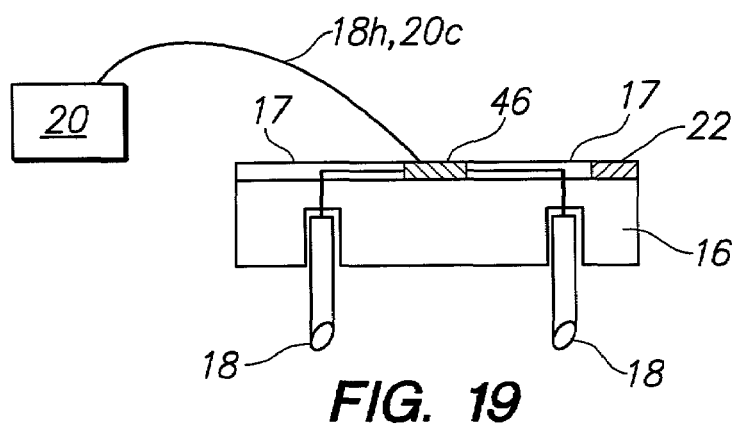
FIG. 19 is a cross sectional view illustrating the use of a printed circuit board in the advancement member.

In an alternative embodiment shown in FIG. 19, electrodes 18 can be coupled to a printed circuit board 17 (using a solder joint or pin coupling), which can be a flex circuit, positioned on the surface 16*s* (proximal or distal) or the interior of disk 16. Circuit board 17 can include a connector 17*c* such as a tab, pin, blade or mechanical connector known in the art, to connect to electrodes 18. Also circuit board 17 can include integral multiplexing or switching circuitry 46 as well as impedance and temperature sensors 22.

Referring to FIGS. 20*a*–20*e*, advancement member 16 can be advanced by a number of different mechanical, electromechanical or pneumatic means known in the art that can be coupled or integral to advancement member 16. In these and related embodiments advancement member 16 can an advancement device 16 or otherwise include an advancement device. In a preferred embodiment shown in FIG. 20*a*, member 16 is advanced by means of a push rod or stiffened cable 16*c* coupled to member surface 16*s* and a handpiece 24 actuable by an actuator 24" on handpiece 24 both described herein. In this and other embodiments retraction of member 16 (e.g. proximal movement) can be achieved through the use of one or more springs 16*sprg*, such as coil spring coupled to the proximal or distal surface of member 16 and the proximal or distal surface of housing interior 12*i*. When member 16 is advanced in the proximal direction spring 16*sprg* is stretched such that the spring now exerts a spring force on member 16 in the proximal direction. When the deployment force exerted by the push rod, servo motor, air pressure or other means described herein is removed, the spring force is sufficient to cause member 16 to be withdrawn back to its starting position and withdrawal electrodes 18 from their deployed state in tissue. In various embodiments, the spring force of the one or more springs 16*sprg* can be in the range of 0.1 to 5 lbs with specific embodiments of 0.25, 0.5, 0.75, 1 and 2.5 lbs. Springs 16*sprg* can be made from spring steel known in the art. In one embodiment springs 16*sprgs* are configured to have a selectable amount of spring force achieved through the amount of compression or deflection of the spring.

Figure 20B:
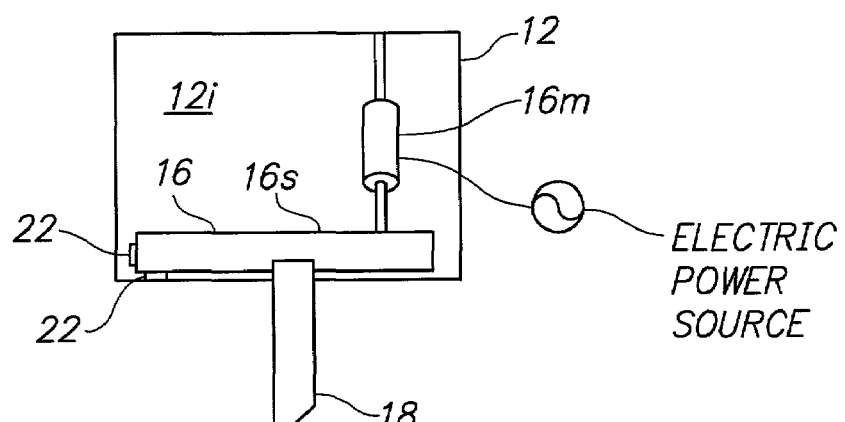
FIG. 20b is a lateral view illustrating an embodiment utilizing a motor or solenoid to advance the advancing the advancement member.
Figure 20A:
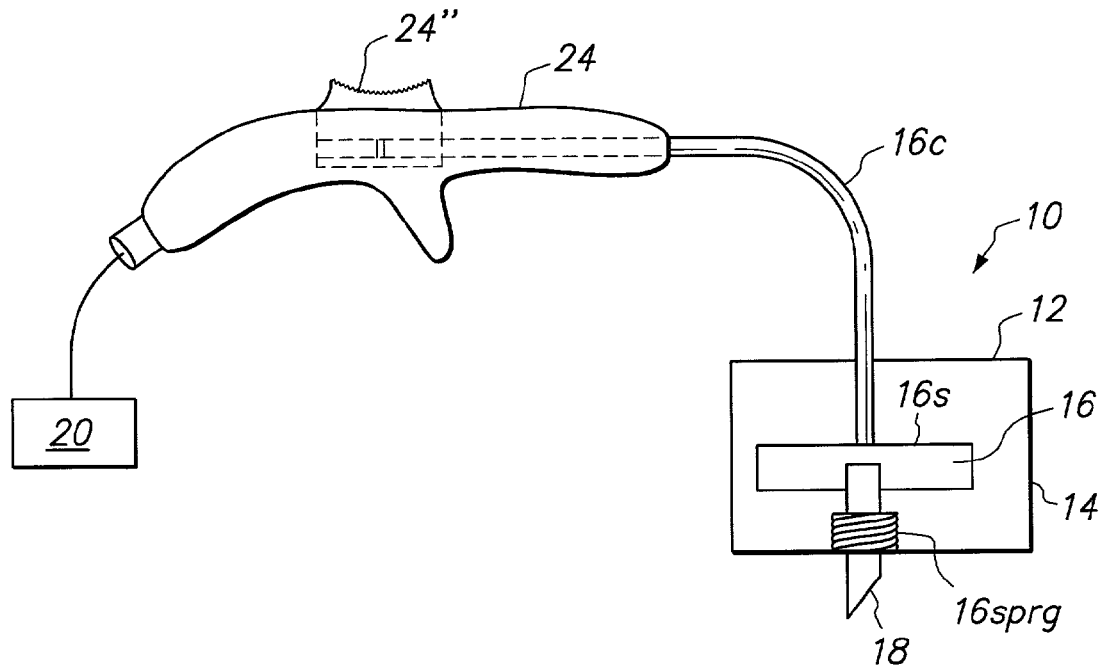
FIG. 20a is a lateral view illustrating an embodiment utilizing a push rod to advance the advancement member as well as the use of springs for retracting the advancement member.
Figure 20C:
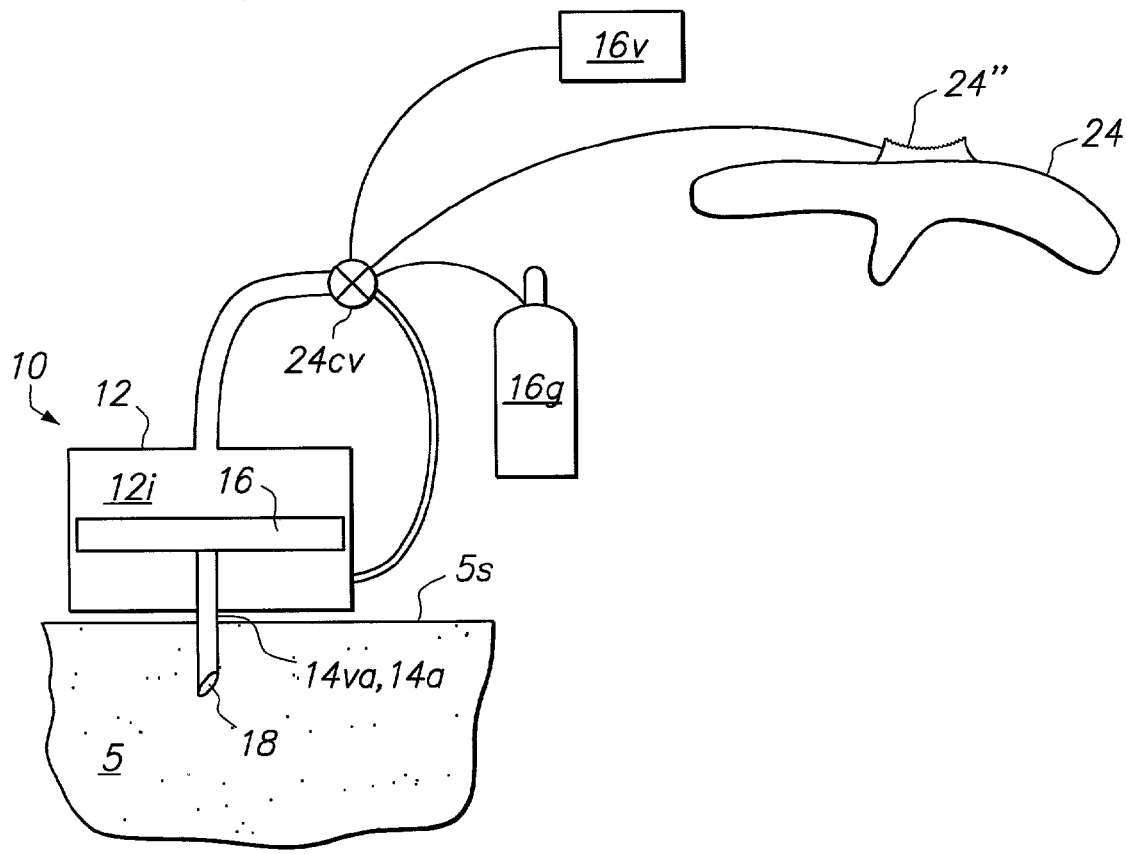
FIG. 20c is a lateral view illustrating an embodiment utilizing pneumatic means to advance the advancing the advancement member as well as the use of vacuum source.

In an alternative embodiment shown in FIG. 20*b*, member 16 can be advanced by a motor, servo motor or solenoid 16*m* known in the art positioned on the interior or exterior of housing 12 and mechanical coupled to member 16. Motor 16*m* can include miniature electric motors including the types used for positioning auto-focus lenses such as those manufactured by RMB Miniature Bearings (Switzerland). Position sensors 22 such as LVDT's can be positioned on member 16 or housing interior 12*i* to provide information on the location of member 16 and amount of deployment of electrodes 18. In still another embodiment shown in FIG. 20*c*, member 16 can be advanced by pneumatic means such as a source of compressed air or inert gas 16*g* and the like 16*g* fluidically coupled to housing interior 12*i*. Gas 16*g* can also be used to cool the housing 12 including surface 14, electrode 18 and tissue surface 5*s*. In a related embodiment, member 16 and housing interior 12*i* are coupled to a vacuum source 16*v* configured to reverse the motion of member 16 and withdrawal coupled electrodes 18. Vacuum source 16*v* can also be used to provide suction and adherence of contacting surface 14 to tissue surface 14 via the use of one or more suction apertures 14*va* positioned on surface 14. Apertures 14*va* can be the same as 14*a*. This solves the problem of achieving and maintaining good contact between contact surface 14 and tissue surface 5*s* (before, during and after energy delivery) as well allowing rapid release between the two. Both compressed gas source 16*g* and vacuum 16*v* can be actuable by actuator 24" which can be or otherwise electronically coupled to a control valve 24*cv* known in the art.

Figure 20D:
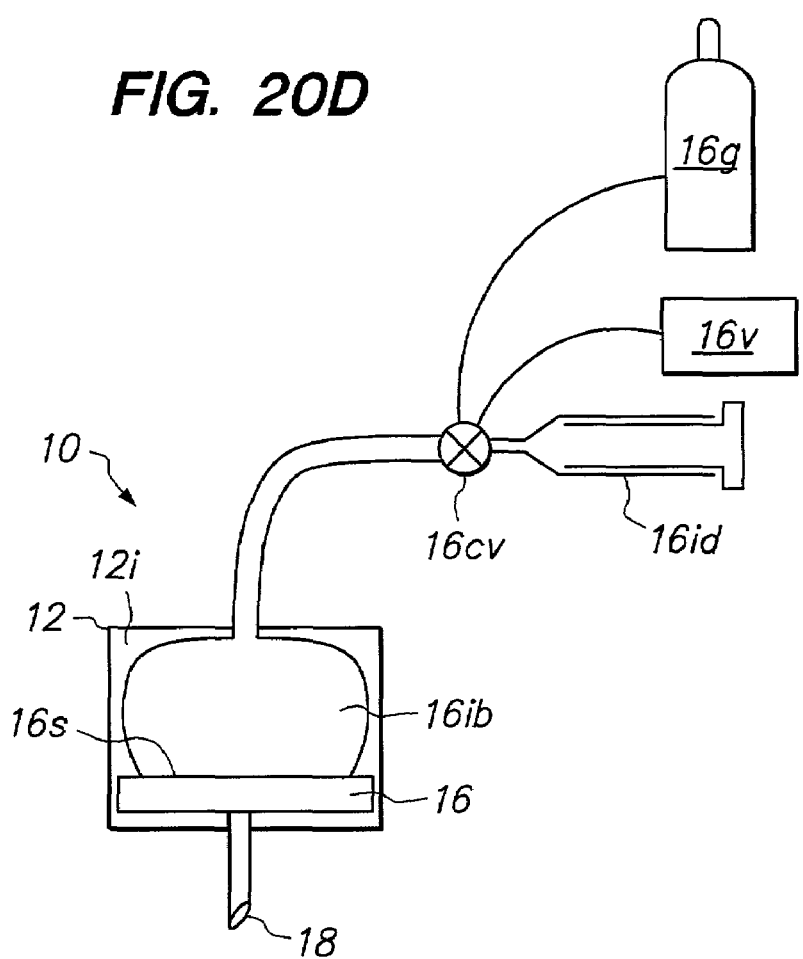
FIG. 20d is a lateral view illustrating an embodiment utilizing an inflatable balloon to advance the advancing the advancement member.

In another embodiment shown in FIG. 20*d*, advancement member 16 is advanced by inflatable balloon device 16*ib* positioned within housing interior 12*i* and coupled (movably or attached) to member 16. Inflation of balloon 16*ib* exerts sufficient force against member surface 16*s* (which is opposed by an equal opposite force on housing interior 12*i*) so as to push member 16 in a distal direction and deploy electrodes 18. Balloon device 16*ib* can be coupled to an inflation/deflation device 16*id* known in the art or to compressed gas source 16*g* and/or vacuum source 16*v*. In an embodiment balloon device 16*ib* can be mechanically coupled, directly attached to or integral with member 16 and housing interior 12*i* such that the inflation/deflation of balloon 16*ib* directly advances and retracts member 16 so as to deploy and retract electrodes 18.

Balloon device 16*ib* can be a balloon catheter or other medical balloon device known in the art made from balloon materials known in the medical device arts including but not limited to polyester, polyethylene (HDPE including radiated HDPE) latex and other non-compliant and compliant balloon materials. Balloon device 16*ib* can be fabricated using balloon blowing methods known in the art including the use of mold blown balloons.

Figure 20E:
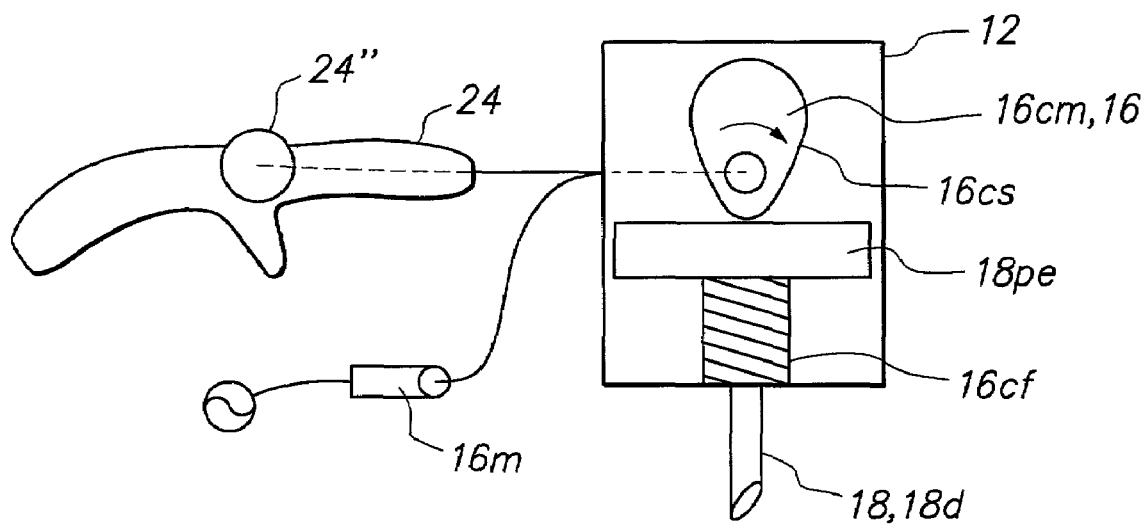
FIG. 20e is a lateral view illustrating an embodiment wherein the advancement member includes a cam to advance the advancement member
Figure 21:
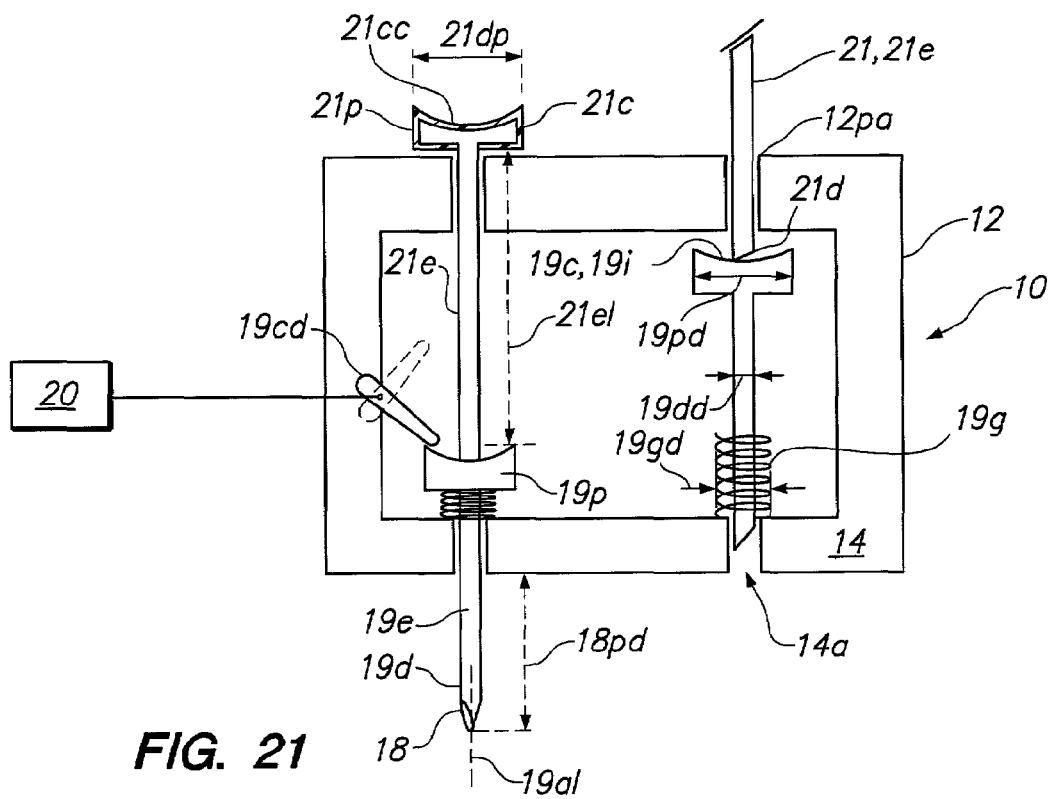
FIG. 21 is a lateral view illustrating an embodiment of an advancement member comprising one or more pushable advancement members with coupled electrodes.
Figure 22:
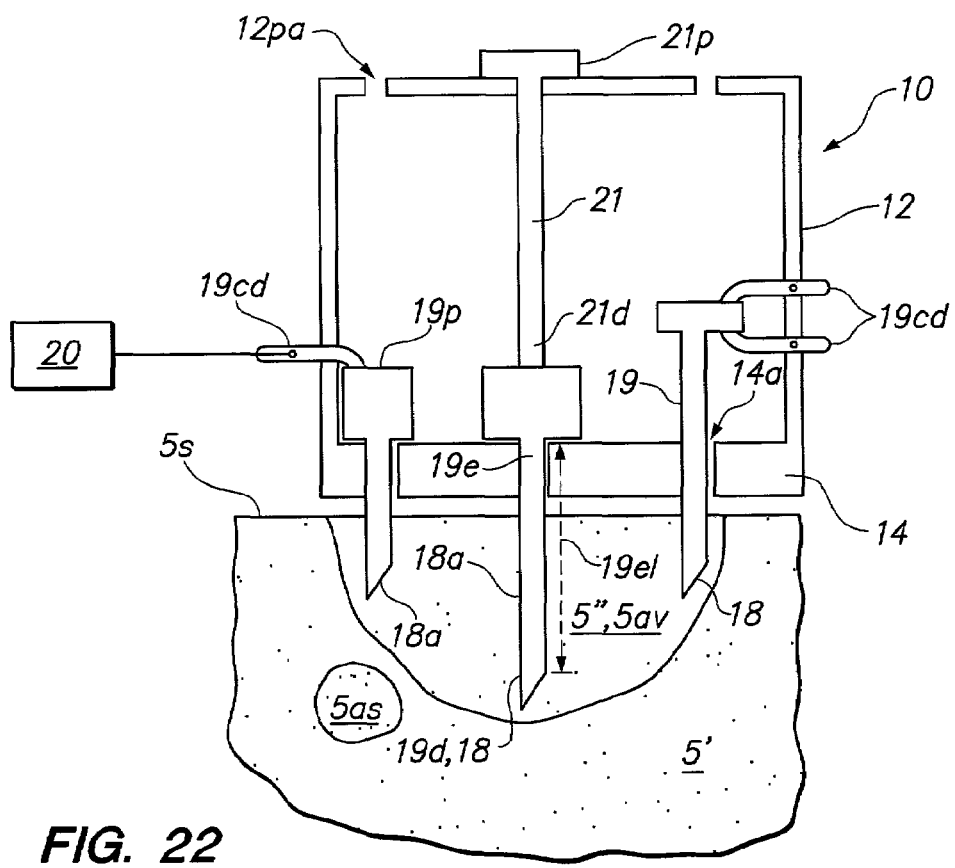
FIG. 22 is a perspective view illustrating the use of the embodiment of the apparatus of FIG. 21.
Figure 23A:
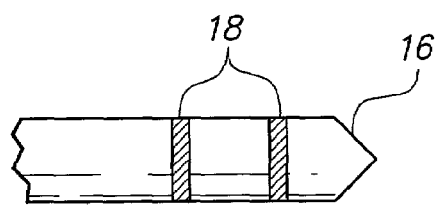
Figure 23B:
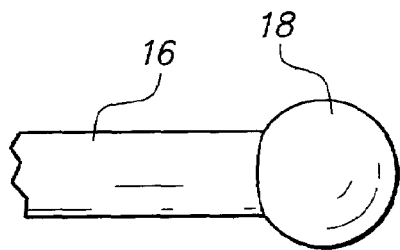
Figure 23C:
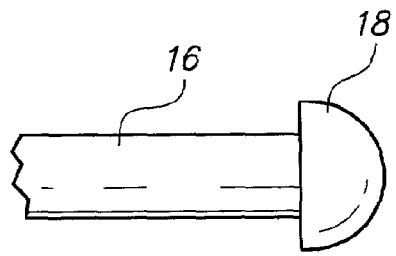
Figure 23D:
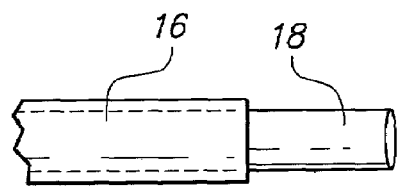
Figure 23E:
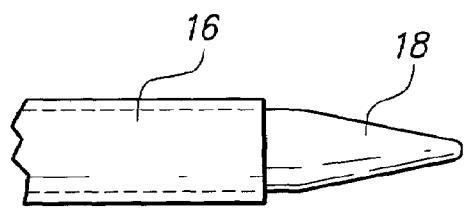
Figure 23F:
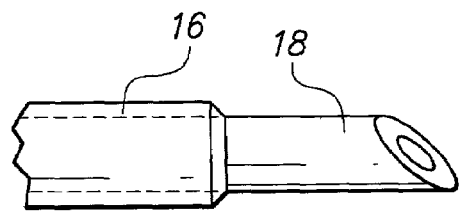
Figure 23G:
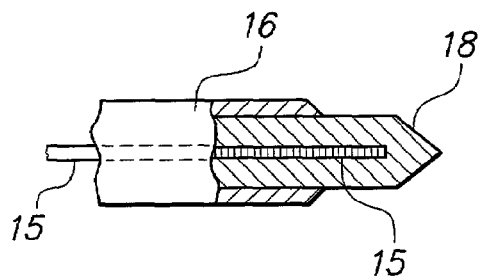
Figure 23H:
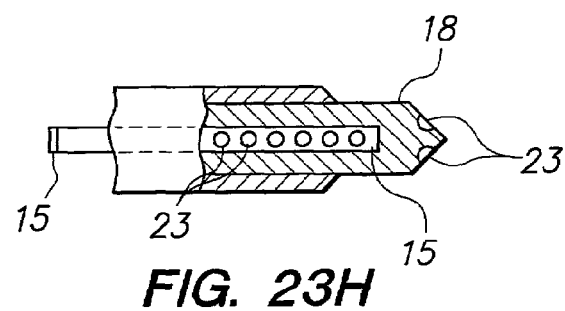

Referring to FIG. 20*e*, in an embodiment advancement member 16 can be an advancement device 16 and can comprise a cam 16*cm* known in the art whose motion serves to advance energy delivery device 18 through contact of the cam surface 16*cs* with the proximal end 18*pe* or other portion the energy delivery device. Cam 16*cm* can be mechanically coupled to an actuator 24" or can coupled to an electric motor 16*m*. Suitable cams include disk cams, translational cams or cylindrical cams configured to operate within housing 12 using rotary, axial or lateral motion and a suitable cam follower 16*cf* which can be coupled to energy delivery device 18 or can be energy delivery device 18 itself. Suitable cam followers include coiled springs. In another embodiment, the advancement device 16 can be movably or detachably coupled to electrodes 18 including rotational, pivotal and reciprocal couplings. Referring to FIGS. 21 and 22, in an embodiment shown in FIG. 21 advancement member 16 comprises one or more individual pushable advancement members 19 each coupled to or including an individual electrode 18 that is aligned with a corresponding apertures 14*a* so as to exit from aperture 14*a*. Pushable advancement members 19 can in turn, be configured to be mechanically advanced by means of an advancement tool 21 that is configured to be inserted through a proximal aperture 12*pa* that is aligned with advancement member longitudinal axis 19*al*.

Pushable member 19 has proximal portion 19*p* and an elongated portion 19*e* including a distal portion 19*d*. Proximal portion 19*p* can have an inward convex curve 19*c* or indentation 19*i* to facilitate force application and advancement by pushing tool 21. Similarly the advancements tool 21 can have a recessed or convex curved contour 21*cc* at its proximal portion to facilitate finger manipulation. At least a portion of distal portion 19*d* comprise electrode 18. The proximal portion can have a significantly larger diameter 19*dp* relative to distal portion diameter 19*dd* rendering proximal portion stiffer than distal portion. The ratio of diameters of proximal to distal portion can be in the range of 1:2 to 1:10, with corresponding ratios of column strength or stiffness. Proximal portion 19*p* has sufficient diameter and column strength to advance the entire length of electrode 18 into various tissue include hard fibrous tissue such. Proximal portion 19*p* can have a diameter in the range of 0.1 to 0.5 inches with specific embodiment of 0.2, 0.3 and 0.4 inches. The proximal portion 19*p* can be made of a conductive high strength metal such as 304 or 304V stainless steel or hardened tool steel. Proximal portion 19*p* and distal portion 19*d* can be an integral component or can be joined using metal working methods known in the art including soldering, brazing and welding. Advancement member 19 can be configured to be retracted by means of a spring such as a coiled spring 19*g* that can be positioned over distal portion 19*p* or otherwise coupled to advancement member 19. Spring 19*g* has diameter 19*gd* configured to fit over distal portion 19*d*/electrode 18, but be contained or but up against the larger diameter of proximal portion 19*p*. A releasable locking or clamp device 19*cd* can be coupled to spring 19*g* and advancement member to be able lock advancement member 19 and electrode position deployed. Clamp 19*cd* can also serve as a electrical/switch to electrically couple electrode 18/member 19 to a power source when member 19 is in a deployed position.

Advancement tool 21 has a proximal portion 21*p* and elongated portion 21*e*, including a distal portion 21*d*. Proximal portion can have a cylindrical shape configured to held and pushed with finger including a recessed proximal contour 21*cp*. Also all, or portions of tool 21, including a proximal portion 21*p*, can be include an electrically insulative layer 21*c* to electrically isolate tool 21 from member 19. Elongated portion 21*e* can be a solid cylindrical shaft configured to be inserted through proximal aperture 12*pa* and make contact with and advance advancement member 19. Proximal portion 21*p* can be configured to remain outside of the housing 12 (by virtue of it having a larger diameter than proximal aperture 12*a*), such that the length 21*e* of elongated portion 21*e* controls the penetration depth 18*pd* of electrode 18. Accordingly, the length 21*el* of elongated portion 21*e* can be in the range of 0.1 to 5 cm with specific embodiment of 0.5, 1.0, 1.5, 2.0, 2.5, 3.0 and 4.0 cm. All or portions of tool 21 can be made from rigid injection moldable polymers such as polycarbonate or ABS or machined tool steel known in the art. In an embodiment, tool 21 can be thumbtack shaped with a plastic proximal portion 21*p* and an embedded elongated portion 21*e*.

Referring to FIG. 22, in a method of the invention the physician can use one or more advancement members 19 having different elongated section lengths 19*e* to deploy one or more selected electrodes of electrode array 18*a* to selectable depths to produce a volumetric pattern 5*p* or profile of deployed electrode 18 to correlate to a tumor mass 5" and avoid nearby critical structures so as to produce a selectable ablation volume 5*av*. The physician could use locking device 19*cd* to lock each electrode in place during energy delivery and subsequently release one or more selected electrode and then re-deploy those electrodes to a different depth for a second delivery of energy to produce a continuous ablation volume or two or more distinct ablation volumes.

Figure 24:
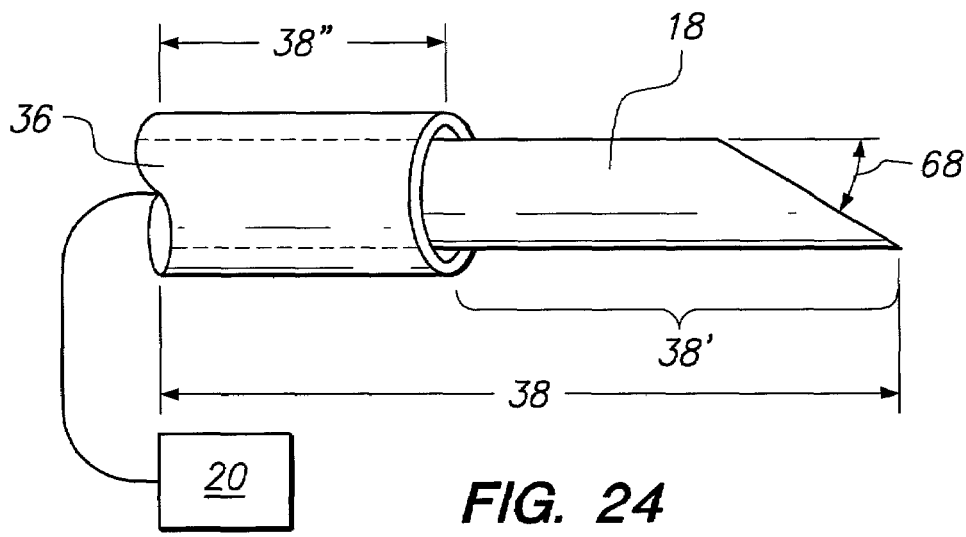
FIG. 24 is lateral view illustrating an embodiment of a needle electrode configured to penetrate tissue.
Figure 25:
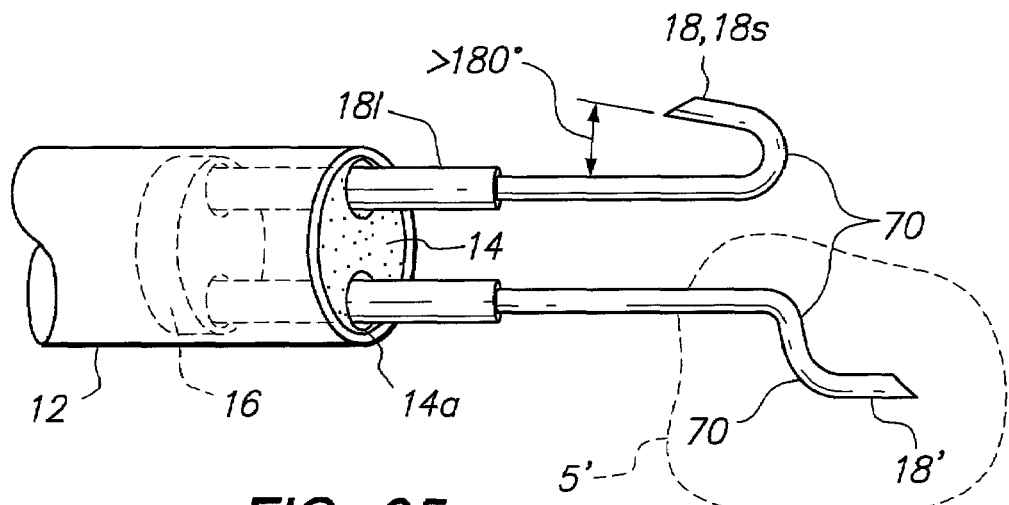
FIG. 25 is lateral view illustrating a needle electrode having at least one radii of curvature.
Figure 26:
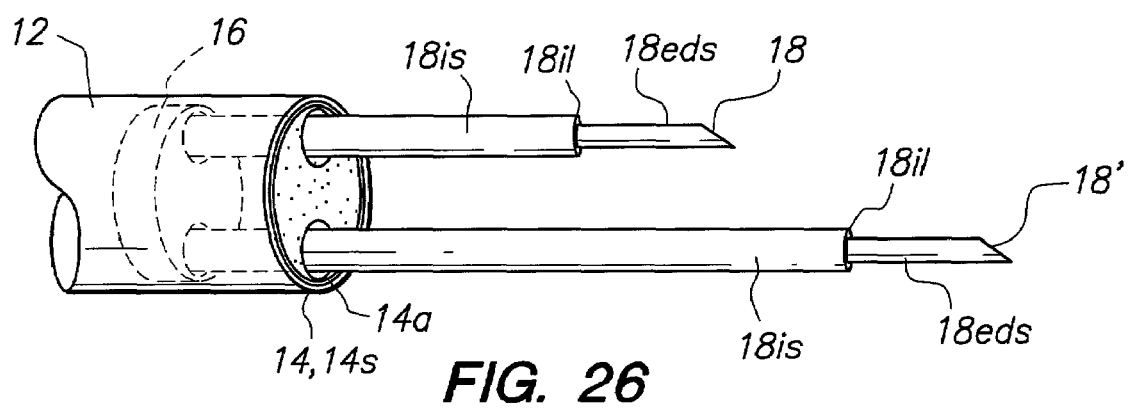
FIG. 26 is a perspective view of a surface treatment apparatus that includes insulation sleeves positioned at exterior surfaces of the electrodes so as to define an energy delivery surface.

Turning now to a discussion of electrodes and electrode configurations, in various embodiments electrodes 18 can have a variety of shapes and geometries. Referring to FIGS. 23*a*–23*f*, example shapes and geometries can include, but are not limited to, ring-like, ball, hemispherical, cylindrical, conical, needle-like and combinations thereof. Referring to FIG. 24, in an embodiment electrode 18 can be a needle with sufficient sharpness to penetrate tissue including fibrous tissue including, encapsulated tumors cartilage and bone. The distal end 18*de* of electrode 18 can have a cut angle 68 that ranges from 1 to 60°, with preferred ranges of at least 25° or, at least 30° and specific embodiment of 25° and 30°. The surface of electrode 18 can be smooth or textured and concave or convex. The conductive surface area 18*s* of electrode 18 can range from 0.05 mm2 to 100 cm2. Referring to FIG. 25, electrode 18 can also be configured to be flexible and or deflectable having one or more radii of curvature 70 which can exceed 180° of curvature. In use, electrode 18 can be positioned to heat, necrose or ablate any selected target tissue volume 5'. A radiopaque marker 11 can be coated on electrodes 18 for visualization purposes.

Electrode 18 can be made of a variety of conductive materials, both metallic and non-metallic. Suitable materials for electrode 18 include, steel such as 304 stainless steel of hypodermic quality, platinum, gold, silver and alloys and combinations thereof. Also, electrode 18 can be made of conductive solid or hollow straight wires of various shapes such as round, flat, triangular, rectangular, hexagonal, elliptical and the like. In a specific embodiment all or portions of electrodes 18 and 18' can be made of a shaped memory metal, such as NiTi, commercially available from Raychem Corporation, Menlo Park, Calif.

Electrode 18 can be coupled to housing 12, contacting surface 14 or advancement member 16 using soldering, brazing, welding, crimping, adhesive bonding and other joining methods known in the medical device arts. Also, electrode 18 can include one or more coupled sensors 22 to measure temperature and impedance (both of the electrode and surrounding tissue), voltage and current other physical properties of the electrode and adjacent tissue. Sensors 22 can be at exterior surfaces of electrodes 18 at their distal ends or intermediate sections.

Referring now to FIGS. 26 through 29 in various embodiments one or more electrode 18 can be covered by an insulative layer 18il so as to have an exterior surface that is wholly or partially insulated and provide a non-insulated area which is an energy delivery surface 18eds. In an embodiment shown in FIG. 26, insulative layer 18il can comprise a sleeve that can be fixed or slidably positioned along the length of electrode 18 to vary and control the length of energy delivery surface 18eds. Suitable material for insulative layer 18il include polyimide and flouro-carbon polymer such as TEFLON.

Figure 27:
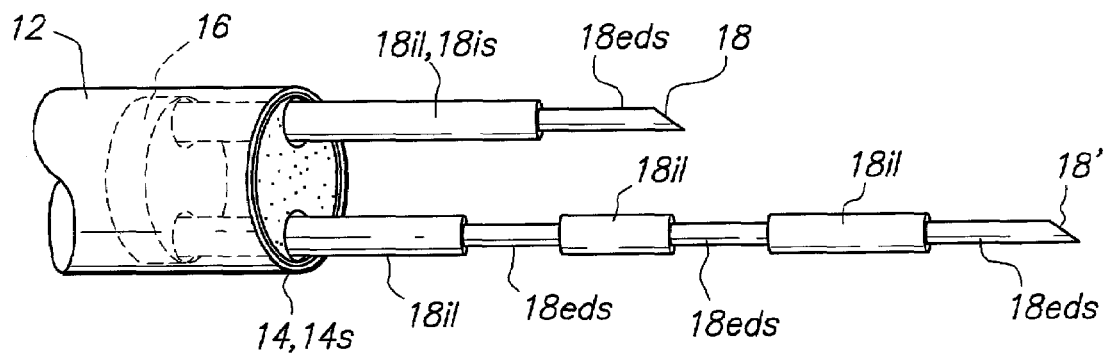
FIG. 27 is a perspective view of a surface treatment apparatus of the present invention that includes multiple insulation sleeves that circumferentially insulate selected sections of the electrodes.
Figure 28:
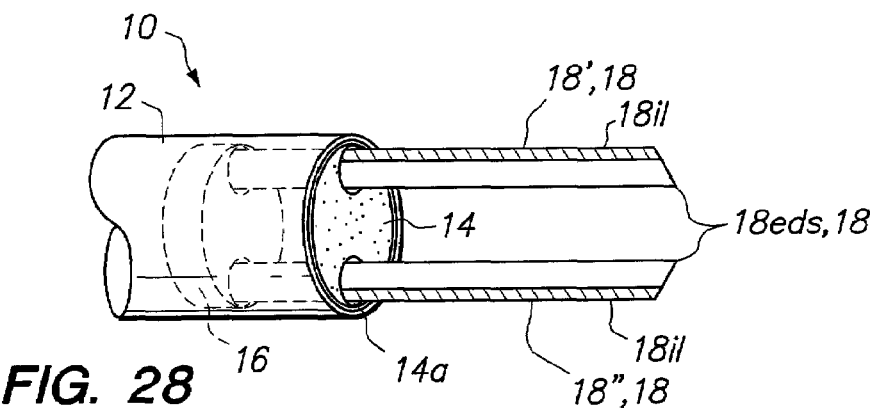
FIG. 28 is a perspective view of a surface treatment apparatus of the present invention with insulation that extends along longitudinal sections of the electrodes to define adjacent longitudinal energy delivery surfaces.
Figure 29:
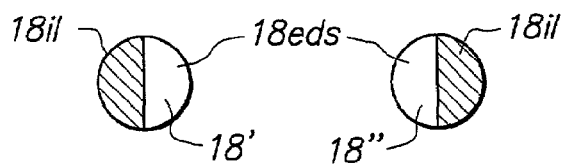
FIG. 29 is a cross-sectional view of the surface treatment apparatus of FIG. 28.

In the embodiment shown in FIG. 27, insulation 18il is formed at the exterior of electrodes 18 in circumferential patterns, leaving a plurality of energy delivery surfaces 18eds. In an embodiment shown in FIGS. 28 and 29, insulation 18il extends along a longitudinal exterior surface of electrodes 18. Insulation 18il can extend along a selected distance along a longitudinal length of electrodes 18 and around a selectable portion of a circumference of electrodes 18. In various embodiments, sections of electrodes 18 can have insulation 18il along selected longitudinal lengths of electrodes 18 as well as completely surround one or more circumferential sections of electrodes 18. Insulation 18il positioned at the exterior of electrodes 18 can be varied to define any desired shape, size and geometry of energy delivery surface 18eds. As described herein, insulation layer 18il can also be applied to contact surface 14l including conductive portion 14con in a similar variety of sizes and geometries.

Figure 30B:
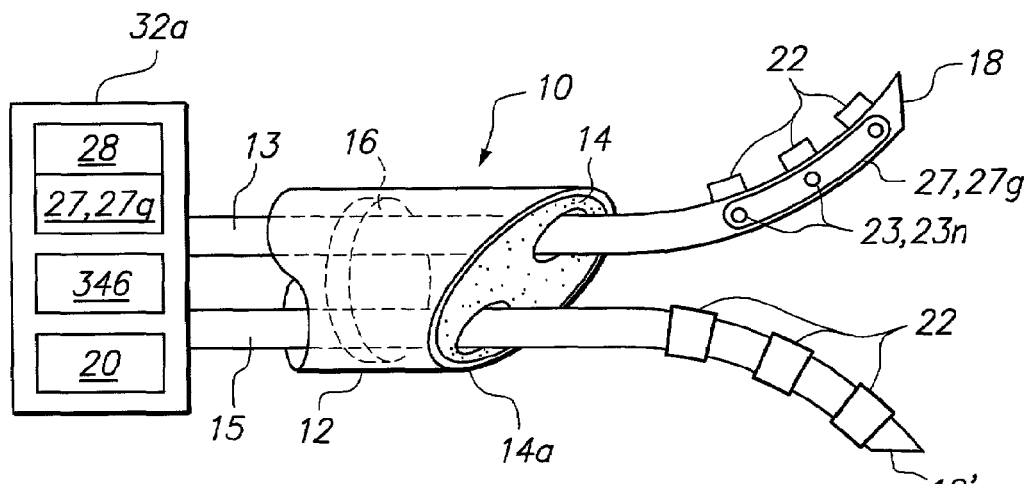
FIG. 30b is a lateral view illustrating of embodiment of the apparatus configured for the delivery of cooling solution to the electrode and surrounding tissue.
Figure 30A:
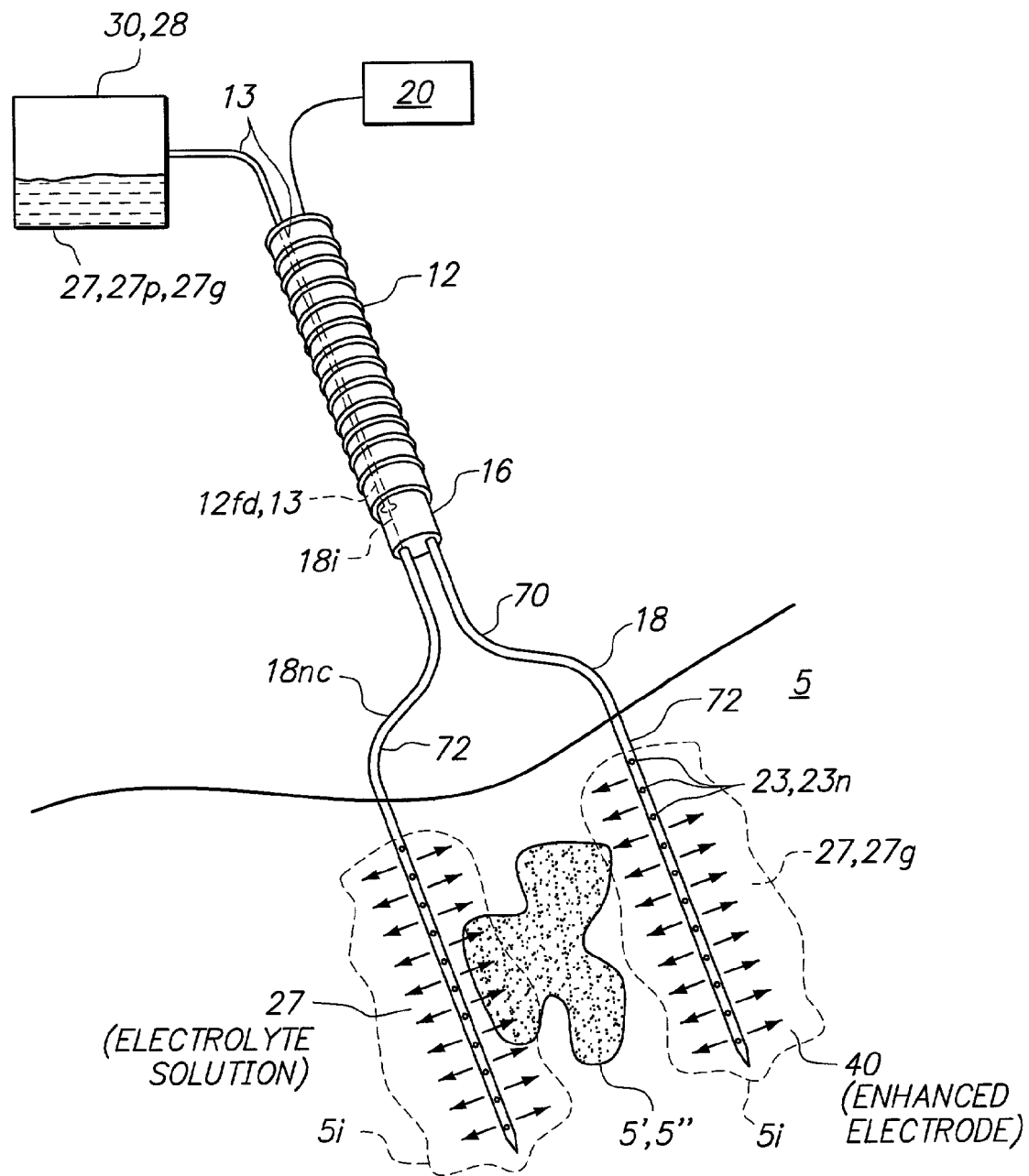
FIG. 30a is a lateral view illustrating an embodiment of the apparatus with an electrode having a lumen and apertures configured for the delivery of fluid and the use of infused fluid to create an enhanced electrode.

Referring now to FIGS. 30a and 30b, electrode 18 can include one or more lumens 72 (which can be contiguous with or the same as lumen 13) coupled to a plurality of fluid distribution ports 23 (which can be apertures 23) from which a variety of fluids 27 can be introduced, including conductivity enhancing fluids, electrolytic solutions, saline solutions, cooling fluids, cryogenic fluids, gases, chemotherapeutic agents, medicaments, gene therapy agents, photo-therapeutic agents, contrast agents, infusion media and combinations thereof. This is accomplished by having ports or apertures 23 that are fluidly coupled to one or more lumens 72 coupled to lumens 13 in turn coupled to fluid reservoir 30 and/or fluid delivery device 28.

In an embodiment shown in FIG. 30a, a conductivity enhancing solution 27 can be infused into target tissue site 5' including tissue mass 5". The conductivity enhancing solution can be infused before during or after the delivery of energy to the tissue site by the energy delivery device. The infusion of a conductivity enhancing solution 27 into the target tissue 5' creates an infused tissue area 5i that has an increased electrical conductivity (versus un-infused tissue) so as to act as an enhanced electrode 40. During RF energy delivery, the current densities in enhanced electrode 40 are greatly lowered allowing the delivery of greater amounts of RF power into electrode 40 and target tissue 5' without impedance failures. In use, the infusion of the target tissue site with conductivity enhancing solution provides two important benefits: (i) faster ablation times; and (ii) the creation of larger lesions; both without impedance-related shut downs of the RF power supply. This is due to the fact that the conductivity enhancing solution reduces current densities and prevents desiccation of tissue adjacent the electrode that would otherwise result in increases in tissue impedance. A preferred example of a conductivity enhancing solution is a hypertonic saline solution. Other examples include halide salt solutions, colloidal-ferro solutions, and colloidal-silver solutions. The conductivity of enhanced electrode 40 can be increased by control of the rate and amount of infusion and the use of solutions with greater concentrations of electrolytes (e.g. saline) and hence greater conductivity. In various embodiments, the use of conductivity enhancing solution 27 allows the delivery of up to 2000 watts of power into the tissue site impedance shut down, with specific embodiments of 50, 100, 150, 250, 500, 1000 and 1500 watts achieved by varying the flow, amount and concentration of infusion solution 27. The infusion of solution 27 can be continuous, pulsed or combinations thereof and can be controlled by a feedback control system described herein. In a specific embodiment, a bolus of infusion solution 27 is delivered prior to energy delivery followed by a continuous delivery initiated before or during energy delivery with energy delivery device 18 or other means.

In an alternative embodiment, conductivity enhancing fluid 27 is injected by electrically non conductive needles or infusion members 18nci (which include lumens 72 and apertures 23) coupled to advancement member 16 and/or housing 12. Members 18nci can be coupled to a fluid delivery device 12fdd positionable within housing 12. Fluid 27 in members 18nci is electrically coupled to an RF or other power source 20 via a conductor or electrode 18c that is positioned within lumens 72 and 13 and electrically coupled to power source 20. Members 18nci are configured to infuse a fluid 27 into target tissue 5' to define a tissue infusion tissue volume 5i. Electrically non-conductive infusion member 18nci can be fabricated from a variety of polymers known in the art including thermoset and rigid polymers such as ABS, acrylic and polycarbonate. Alternatively member 18nci can be fabricated from insulated metal using insulation materials described herein.

In various embodiments, the conductivity of the tumor mass 5' can be enhanced so as to preferentially increase the rate and total amount of delivery of energy to the tumor mass 5' relative to healthy tissue. This can be achieved by infusing conductivity enhancing solution 27 directly into the tumor mass 5' through the use of a needle electrode 18 place within the tumor mass only. In related embodiments solution 27 can be configured to remain or be preferentially absorbed or otherwise taken up by tumor mass 5". This can be achieved by controlling by one or more of the osmolality, viscosity and concentration of solution 27.

As shown in FIG. 30b apertures 23 can be also configured to provide cooling of electrodes 18 and surrounding tissue to prevent tissue desiccation and the deposition of charred tissue on the surface of electrode 18 and in turn, prevent the subsequent development of excessive impedance at or near electrode 18. The cooling is accomplished by both the use of a cooled solution to cool the electrodes by a combination of convection and conduction. The amount of cooling can be controlled by control of one or more of the following parameters: (i) temperature of the cooling solution; (ii) flow rates of the cooling solution; (iii) heat capacity (e.g. specific heat) of the cooling solution; and (iv) combinations thereof. Examples of cooling solutions include, water, saline solution and ethanol and combinations thereof. Other embodiments can utilize a cooling fluid or gas 27g that serves to cool electrodes 18 by ebullient cooling or Joule-Thomson Effect cooling as well as the mechanisms described above. Embodiments utilizing Joule-Thomson Effect cooling can have a nozzle-shaped aperture 23n to provide for expansion of a cooling fluid 27g. Suitable cooling fluids 27g can include, but are not limited to, chilled water, freon, liquid $CO_2$, liquid nitrogen, and other cryogenic gases.

Turning now to a discussion of power supplies and power delivery, when power supply 20 is a RF source it produces RF energy delivered to tissue through RF electrode 18. RF energy flowing through tissue causes heating of the tissue due to absorption of the RF energy by the tissue and ohmic heating due to electrical resistance of the tissue. The heating causes tissue temperature to rise sufficiently to cause cell injury and death particularly for temperatures in excess of 50–55° C. Increased amounts of power will resultant in higher temperature and greater magnitude of cell death it is desirable to be able to deliver a range of RF power levels depending upon a variety of parameters include but not limited to tumor size, tissue type, tumor location and amount of tumor vascularization. Accordingly in varying embodiments, RF power supply 20 can be figured to deliver between 5 to 200 watts, preferably 5 to 100, and still more preferably 5 to 50 watts of electromagnetic energy is to the electrodes of energy delivery device 18 without impeding out. This can be accomplished through the use of cooling solutions and methods described herein as well as the use of power duty cycles to allow for a certain amount of thermal dissipation in and around electrodes 18.

Electrodes 18 are electromagnetically coupled to energy source 20. The coupling can be direct from energy source 20 to each electrode 18 respectively, or indirect by using a collet, sleeve, connector, lemo connectors, cable, wire and the like which couples one or more electrodes to energy source 20. Energy can also be beamed or transmitted to electrodes 18 using RF transmission or diathermy methods known in the art. Delivered energies can be in the range of 1 to 100,000 joules, more preferably in the range 100 to 50000 joules, still more preferably in the range of 100 to 5000 and still yet more preferably in the range 100 to 1000 joules. Lower amounts of energy can be delivered for the ablation of smaller structures such as nerves and small tumors with higher amounts of energy for larger tumors. Also delivered energies can be modified (by virtue of the signal modulation and frequency) to ablate or coagulate blood vessels vascularizing the tumor. This provides the benefit of providing a higher degree of assurance of coagulating the blood supply of and to the tumor.

Turning to a discussion of sensors, sensor 22 can be selected to measure temperature, impedance, pressure or other tissue property described herein to permit real time monitoring, imaging and control of energy delivery or fluid delivery described herein. The use of one or more sensors 22 coupled to the housing 12, energy delivery surface 14, energy delivery devices 18 or handpiece 24 permits accurate measurement of temperature at tissue site 5' in order to determine the following: (i) the extent of cell necrosis; (ii) the amount of cell necrosis; (iii) whether or not further cell necrosis is needed; and (iv) the boundary or periphery of the ablated tissue mass. Further, the use sensor 22 reduces non-targeted tissue from being injured, destroyed or ablated.

Referring to back FIG. 2, one or more sensors 22 can be positioned at the exterior surfaces of electrodes 18, at their distal ends 18*de*, or intermediate sections. This allows monitoring of temperature, impedance or other tissue property at various points within and outside of the interior of tissue site 5', such that a determination of one or more of the following can be made: (i) the periphery of the selected tissue/tumor mass; (ii) the periphery of the developing ablation volume 5*av*; and (iii) a determination of when cell necrosis is complete. If at any time, sensor 22 determines that a desired cell necrosis temperature is exceeded, then an appropriate feedback signal is received at power source 20 coupled to energy delivery device 18 which then regulates the amount of electromagnetic energy delivered to electrodes 18. This reduces damage to healthy tissue surrounding the targeted mass to be ablated. Sensors 22 can be coupled to a multiplexer or other switching device (described herein) so as to integrate the signal from one or more sensors 22 to obtain a composite picture of the sensed property for all or selected portions of the tumor surface area 5*b*.

Sensor 22 can be of conventional design, including but not limited to thermal sensors, acoustical sensors, optical sensors, pH sensors, gas sensors, flow sensors positional sensors and pressure/force sensors. Thermal sensors can include thermistors, thermocouples, resistive wires, optical sensors and the like. A suitable thermal sensor 22 includes a T type thermocouple with copper constantene, J type, E type, K type, fiber optics, resistive wires, thermocouple IR detectors, and the like. Acoustical sensors can include ultrasound sensors including piezoelectric sensors which can be configured in an array. Pressure and force sensors can include strain gauge sensors including silicon-based strain gauges contained in a miniaturized silicon chip including an ASIC. Optical sensors can include photo-multipliers and micro-machined optical fibers. Gas sensors can include $O_2$ sensors such as Clark electrodes, $CO_2$ sensors and other electrochemical based sensors known in the art. Flow/velocity sensors can include ultrasound sensors, electromagnetic sensors and aneometric sensors which can be configured to detect both liquid and gaseous velocities and flow rates. Positional sensors can include LVDT's, and Hall effect sensors. Other sensors which can be employed include impedance sensors, antibody-based sensors, biosensors (e.g. glucose) and chemical sensors. In various embodiments, one sensor can be configured to detect multiple parameters or one or more sensors can be coupled together or arrayed so as to provide composite information of a tissue site 5'. Pressure sensors can be selected and/or configured to detect pressure differentials less than 1 mmHg and even less than 0.1 mmHg. In specific embodiments, pressure sensor 22 can be a micro-machined fiber optic sensor, a PSP-1 pressure sensor manufactured by Gaymar Industries Inc., (Orchard Park, N.Y.) or a Monolithic Integrated Pressure sensor made by the Fraunhofer-Institut (Duisburg, Germany). Suitable ultrasound sensors or transducers can include a Model 21362 imaging probe manufactured by the Hewlett Packard Company, Palo Alto, Calif.

In other embodiments, at least a portion of sensors 22 can be pressure or force sensors positioned on or in housing 12, including tissue contact surface 14, so as to be able to measure the force applied by surface 14 onto tissue surface 5*s* and into target tissue site 5' tissue tumor mass 5". Additionally, pressure/force sensors can provide an indication of the size of the ablation volume and/or the degree of thermal injury due to the tissue shrinkage that occurs with the thermal contraction and denaturization of collagen comprising tumor mass 5" as well as the shrinkage/coagulation of the vasculature within the tissue mass. Thus, a decreased pressure on surface 5*s* can be an indication of the size of an ablation volume and/or the completeness of ablation of a tumor mass. Also, an increase in pressure could provide an indication as well due to the development of steam and other gas pressure beneath tissue surface 5*s*. Measurement of pressure changes occurring during RF or other thermal ablation treatment described herein can be combined with temperature measurements to provide a more robust indication of complete tumor ablation and hence clinical endpoint. In one embodiment, an algorithm for determining an endpoint for ablation can include a polynomial equation and/or multi-variant analysis using both measurement tissue temperature and tissue pressure as input parameters.

Pressure or force sensors 22 can be strain gauges, silicon based pressure sensors, accelerometers, semiconductor gauge sensors, silicon strain gauges, heat resistant silicon strain gauges, micro-machined pressure sensors and the like. In an embodiment pressure sensor 22 can be a flexible silicon strain gauge manufactured by the BF Goodrich Advanced Micro Machines (Burnsville, Minn.).

Figure 31:
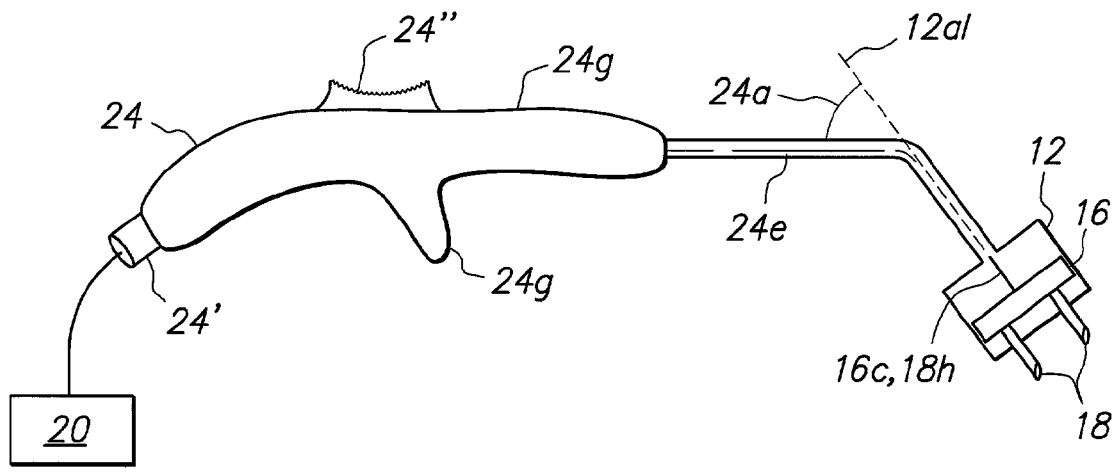
FIG. 31 is a lateral view illustrating an embodiment of a surface treatment apparatus including a handpiece.

Referring now to FIGS. 31–35, in various embodiments, housing 12 can include or be coupled to a graspable handle or handpiece 24. As shown in FIG. 31, handpiece 24 can include a grip portion 24g and elongated portion 24e. Elongated portion 24e can be attached at an angel 24a with respect to the longitudinal axis 12al of housing 12. Angle 24a can range from 0 to 360° with specific embodiments of 15, 30, 45, 60, 90, 120 and 180°. Also, all or portions of handpiece 24 can be integral to housing 12.

The grip portion 24g can have a variety of shapes and grips including, but not limited to, a screw driver grip, pistol grip and other grips known in the art. In various embodiments, elongated portion 24e can be a wire-reinforced or metal-braided polymer shaft, a catheter, a multi-lumen catheter, port device (such as those made by the Heartport® Corp., Redwood City, Calif.), subcutaneous port or other medical introducing device known to those skilled in the art. In a specific embodiment, elongated portion 24e is a trocar or a safety trocar and the like. Also as described herein, elongated portion 24e can be adapted to be coupled to or used in conjunction with various viewing devices including, endoscopes, optical fibers, video imaging devices and the like. Elongated portion 24e can be constructed of a variety of metal grade metals known in the art including stainless steel such as 304 or 304V stainless steel as well shape memory metal such as Nitinol. Elongated portion 24e can also be constructed from rigid polymers such as polycarbonate or ABS or resilient polymers including Pebax®, polyurethane, silicones HDPE, LDPE, polyesters and combinations thereof.

Figure 32A:
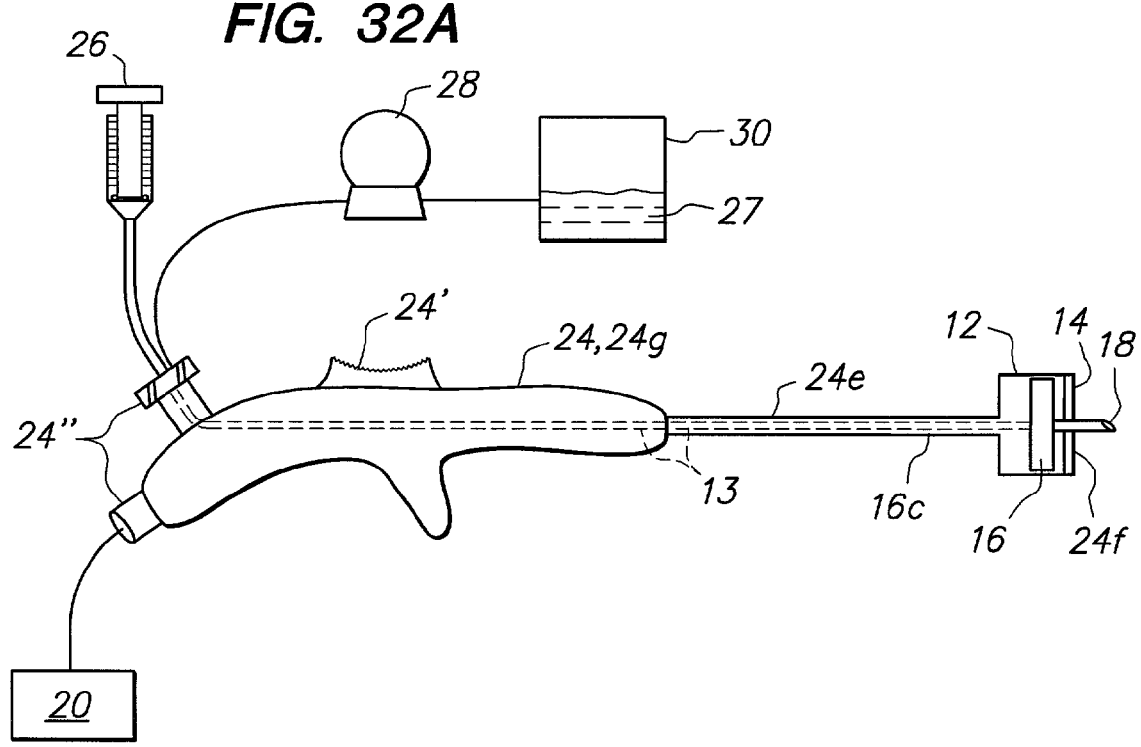
FIG. 32a is a lateral view illustrating an embodiment of the handpiece configured to be coupled to fluid delivery and aspirating devices.

In various embodiments, handpiece 24 can include ports 24' and actuators 24" shown in FIG. 32a. Ports 24' can be coupled to one or more lumens 13 and can include fluid and gas ports/connectors and electrical, optical connectors. In various embodiments, ports 24' can be configured for aspiration/vacuum (including the aspiration of tissue), and the delivery of cooling, conductivity enhancing, electrolytic, irrigation, polymer and other fluids (both liquid and gas) described herein. Ports 24' can include but are not limited to luer fittings, valves (one-way, two-way), toughy-bourst connectors, swage fittings and other adaptors and medical fittings known in the art. Ports 24' can also include lemo-connectors, computer connectors (serial, parallel, DIN, etc.) micro connectors and other electrical varieties well known to those skilled in the art. Further, ports 24' can include opto-electronic connections which allow optical and electronic coupling of optical fibers and/or viewing scopes (such as an endoscope) to illuminating sources, eye pieces, video monitors and the like.

Actuators 24" can include rocker switches, pivot bars, buttons, knobs, ratchets, cams, rack and pinion mechanisms, levers, slides and other mechanical actuators known in the art, all or portions of which can be indexed. These actuators can be configured to be mechanically, electro-mechanically, or optically coupled to pull wires, deflection mechanisms and the like allowing selective control and steering of introducer 12. Also actuators 24" can be configured such that longitudinal movement of actuators 24" is translated to a combination of lateral or longitudinal movement of electrodes 18, contact surface 14, or forceps 24p.

Figure 32B:
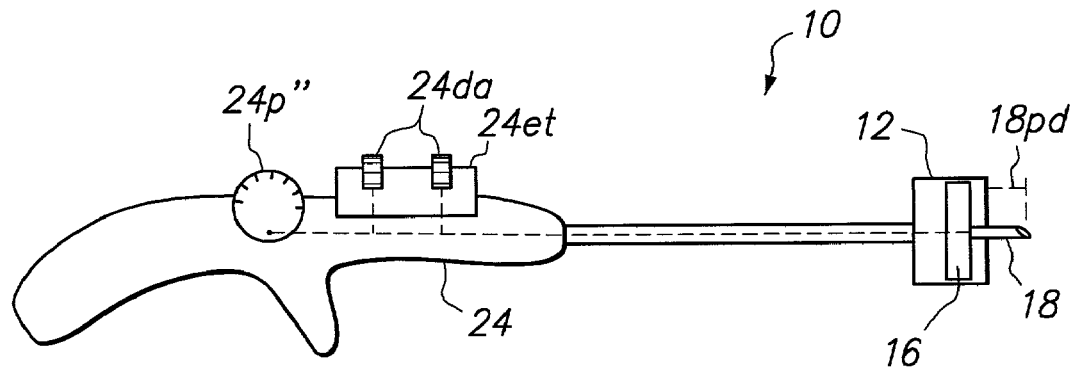
FIG. 32b is a lateral view illustrating an embodiment of the handpiece including a positioning fixture and/or a template for control of the deployment of electrodes into tissue.

In an embodiment shown in FIG. 32b, actuators 24" can include a positioning fixture 24"p to control the penetration depth of electrodes 18. Positioning fixture 24"p can include a rotatable positioning fixture, an indexed positioning fixture or a micro positioning fixture all known in the art. Also the handpiece can include an electrode deployment template 24et with individual deployment actuators 24da for each electrode that enables or disables deployment of individual electrode mechanically coupled to the electrode template.

As shown in FIG. 32a, hand piece 24 can also be configured to be coupled to tissue aspiration/collection devices 26, fluid delivery devices 28 (e.g. infusion pumps) fluid reservoirs (cooling, electrolytic, irrigation etc.) 30 or power source 20 through the use of ports 24'. Tissue aspiration/collection devices 26 can include syringes, vacuum sources coupled to a filter or collection chamber/bag. Fluid delivery device 28 can include medical infusion pumps, Harvard pumps, peristaltic pumps, syringes and the like.

Figure 33:
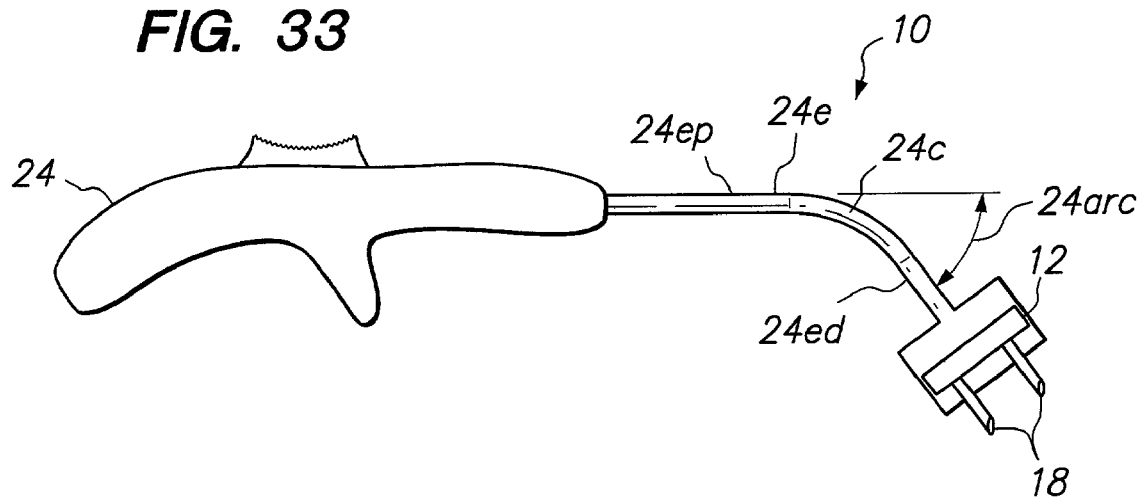
FIG. 33 is a lateral view illustrating an embodiment of the handpiece including a curved portion.

In an embodiment shown in FIG. 33 elongated portion 24e can include a curved portion 24c positioned at the proximal or distal sections 24ep and 24ed of elongate portion 24e. Curved portion 24c can have a preselected amount or arc of curvature 24arc ranging from 1 to 270° with specific embodiments of 30, 60, 90, 120 and 180. In various embodiments, the length, shape and amount of curvature of handpiece 24 including curved portion 24c are configured to allow the physician to position the housing 12 including tissue contacting surface 14 on the side (lateral) or back (posterior) surface of a target tissue site such as the liver using an anterior or other approach. Curved portion 24c can include a curvilinear, hyperbolic, parabolic or shaped curve or combinations thereof.

Figure 34:
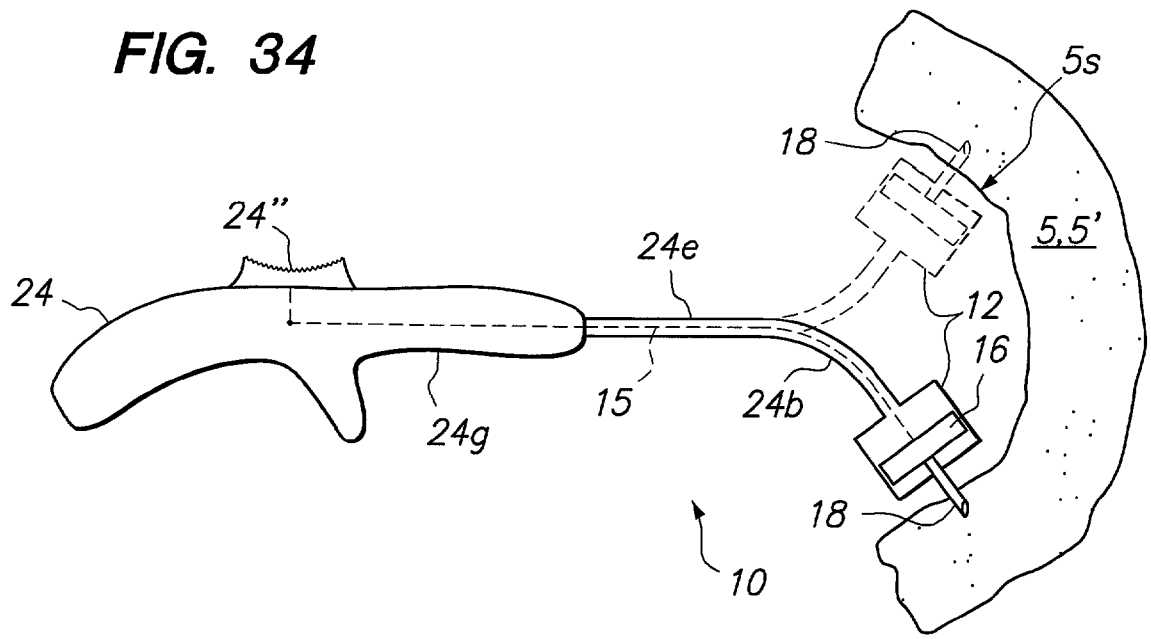
FIG. 34 is a lateral view illustrating an embodiment of the handpiece including a bendable portion.
Figure 35:
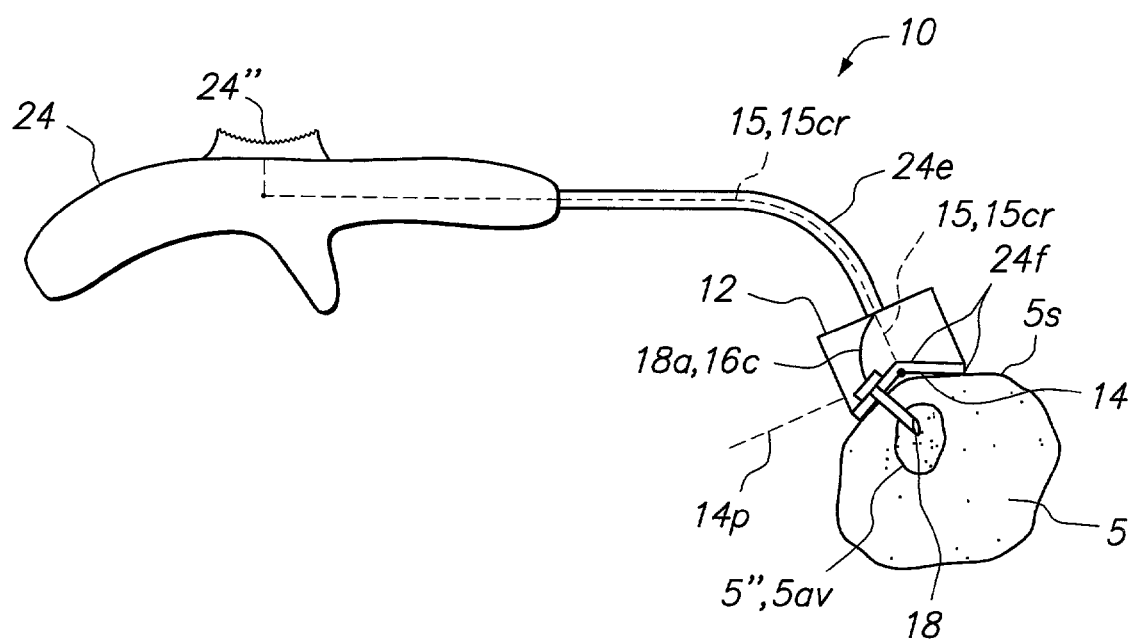
FIG. 35 is a lateral view illustrating an embodiment of a surface treatment apparatus having a handpiece configured to controllably manipulate the tissue contact surface.

In an embodiment shown in FIG. 34, handpiece 24 including elongated portion 24e can include a bendable or deflectable portion 24b which is configured to allow portions of handpiece 24 to bend a selectable amount to allow the physician to position housing 12 on a selected surface of a target organ 5 including the posterior and lateral surfaces of the organ. In various embodiments, bendable portion 24b can comprise an articulated section using corrugated polymers known in the art or a section made from flexible or resilient materials including elastomers such as silicone or polyurethane, a coiled spring, a bendable wire, or a wire reinforced catheter. In a preferred embodiment, bendable portion 24b comprises a braided resilient polymer tube known in the art. Bendable portion 24b can be deflected using a number of deflection mechanisms known in the art including pull wires 15 and the like. Alternatively, for embodiments having articulated bendable portions 24b, the articulations can have sufficient rigidity (e.g. bending force) to maintain its shape once the physician has bent it into a desired position. This can be achieved through the use of metallic or steel articulated sections 24b having bending force ranging from 0.5 to 10 lbs with specific embodiments of 1, 2.5 and 5 lbs of force.

In other embodiments, handpiece 24 can be configured to not only position housing 12 adjacent the desired target tissue site, but also to shape or otherwise manipulate tissue contact surface 14 so as to at least partially conform contact surface 14 and/or housing 12 to the contour of the target tissue surface. This can be accomplished through a variety of mechanical means known in the surgical instrument arts. In an embodiment shown FIG. 35, this can be accomplished by a pull wire 15 (contained within elongated section 24e) attached in two or more places to a bendable tissue contact surface 14 and also to handpiece 24 so as to be controlled by actuators 24". In a related embodiment, it can be accomplished through the use of a forceps device 24f attached to tissue surface 14 and mechanically coupled to handpiece 24 (including actuator 24") by a connecting rod 15cr or pull wire 15. Actuator 24", connecting rod 15cr or pull wire 15 can be so configured such that a longitudinal movement of actuator 24 (with respect to axis 12*al*) is translated into lateral or curved movement of surface 14 relative to a plane 14*p* of surface 14. Forcep device 24*f* can include forceps, curved forceps, hemostats, or any hinged or grasping device known in the surgical or mechanical arts.

The use of forcep device 24*f* allows the physician to not only shape the contact surface 14 to the tissue surface but also to apply a selectable amount of pressure to the tissue surface to do one or more of the following: (i) stabilize the housing on the tissue surface; (ii) at least partially immobilize the target tissue site; and (iii) at least partially stop the flow of blood to the target tissue through the application of direct pressure including onto a selected vessel or vasculature.

In use, coupled forcep device 24*f*, provides the benefit of improving the contact of surface 14 to the tissue surface so as to provide a more precise delivery of energy to the target tissue site and prevent damage to surrounding healthy structure. It also improves the ease and accuracy of the positioning and deployment of needles 18. Further, embodiments of the invention with coupled forcep device 24*f* reduce the amount of manipulation of the liver or other target organ to position housing 12 and needles 18 thus making associated ablation procedure less invasive and less traumatic reducing the likelihood of morbidity and mortality as well as reducing procedure time. This and related embodiments can be configured for endoscopic applications.

In use, a movable or bendable handpiece 24 and introducer solves the problem of allowing the physician to atraumatically access difficult to reach portions of the liver including the posterior portion and lateral portions that are butting up against adjacent organs and structures. More importantly, the handpiece allows the physician to reach such locations without having to appreciably move or distend diseased (e.g. cirrhosed) or damaged portions of the liver that are subject to injury including hemorrhage from such movement. In use embodiments having a bendable handpiece serve to reduce the likelihood of injury during the positioning of the device to the desired target tissue surface 5*s*. Coating of the exterior of one or more of the handpiece, introducer and housing with a lubricous coating known in the art also serves to make the positioning of the housing, less atraumatic, faster and easier. Such coatings can include TEFLON® and can be in the range of 0.0001 to 0.0003" in thickness.

Figure 36A:
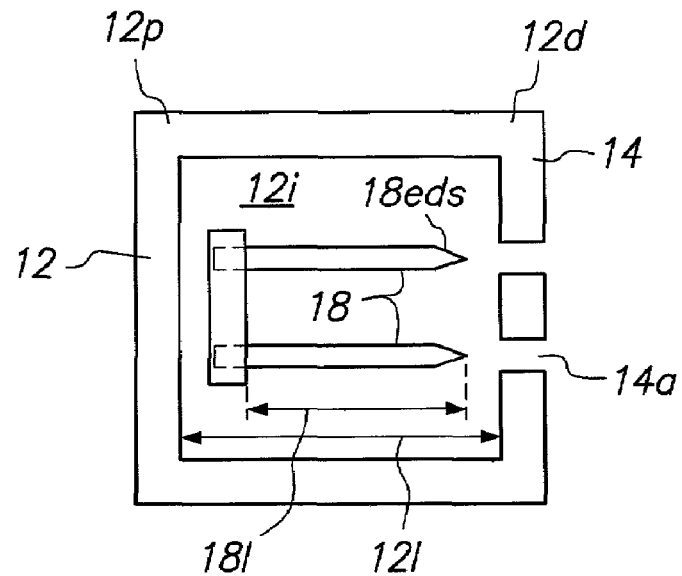
FIGS. 36a and 36b are lateral views illustrating an embodiment of the surface treatment apparatus with electrodes in a non-deployed and deployed state.
Figure 36B:
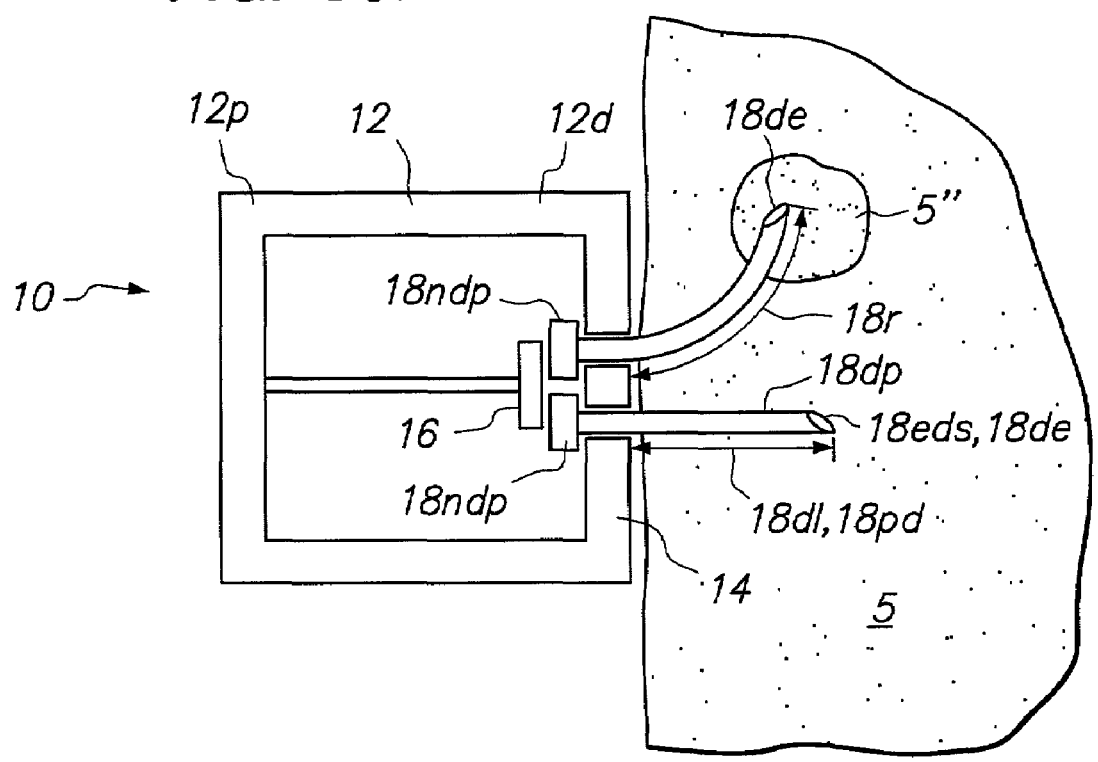

Turning to a discussion of electrode deployment, in various embodiments electrodes 18 can be controllably deployed from housing 12. Referring to FIGS. 36*a*–36*b*, electrodes 18 can have a non-deployed state in which they are contained within housing 12 and a deployed state in which at least a portion of the electrode is advanced out of the housing and into tissue. For embodiments having curved electrodes, electrodes 18 are pre-sprung or otherwise given memory using metallurgical methods known in the art (such as mandrel shaping) such that their deployed state electrodes 18 assume a curved shape having at least one radius of curvature 18*r*. Further, the electrode 18 can be configured to assume a greater amount of curvature or otherwise be deflected or in response to a force exerted by tissue including tumor mass 5" such that electrode 18 has a changing direction of travel in tissue as the electrode is advanced into tissue. In various embodiments, this can be achieved through the selection of the material properties of the electrode including but not limited to elastic modulus, % elongation, yield strength, column strength, diameter, bending modulus, spring constant, degree of tapering and the like.

In a preferred embodiment, in their non deployed state electrodes 18 are completely contained or recessed within housing 12, particular tissue penetrating distal end 18*de* in the non deployed state and then subsequently during electrode retraction. This configuration provides the benefit of a safety feature to prevent accidental stick injury to medical personnel and the patient. This is achieved by having electrode length 18*l* be less than housing length 12*l*. In its fully deployed state, electrode 18 has a deployed portion 18*dp* protruding distally out of housing 12 and into tissue and a non-deployed portion 18*ndp* that is contained in housing 12. In various embodiments, electrode 18 has a deployed length 18*dl* in the range of 0.25 to 20 cm with specific embodiments of 1.5 cm, 2.5, 4, 5 and 10 cms in order to achieve a penetration depth 18*pd* roughly corresponding to these amounts. In an embodiment, the non-deployed length can be in the range of 0.25 to 3 cm. At the same time, the housing 12 has sufficient length to allow complete withdrawal of electrodes 18 into the housing to prevent accidental stick injury both to the patient and medical personnel during positioning and manipulation of the housing and apparatus. Thus in various embodiments, the length of housing 12 can range of 0.5 cm to 9 cm with specific embodiments of 2.5, 5.0 and 7.5 cm. The actual lengths of electrode 18 depends on the location of tissue site 5' to be ablated, its distance from the site, its accessibility as well as whether or not the physician chooses a open surgical procedure or a percutaneous, or other minimally invasive procedure.

By varying the depth of penetration, the pattern and number of deployed electrodes, electrodes 18 can be selectably deployable from housing 12 to create any desired geometric volume of cell necrosis. Accordingly, electrodes 18 can be configured to create a variety of different geometric ablation volumes or cell necrosis zones including but not limited to spherical, semi-spherical, spheroid, triangular, semi-triangular, square, semi-square, rectangular, semi-rectangular, conical, semi-conical, quadrilateral, semi-quadrilateral, semi-quadrilateral, rhomboidal, semi-rhomboidal, trapezoidal, semi-trapezoidal, combinations of the preceding, geometries with non-planar sections or sides, free-form and the like.

Figure 37:
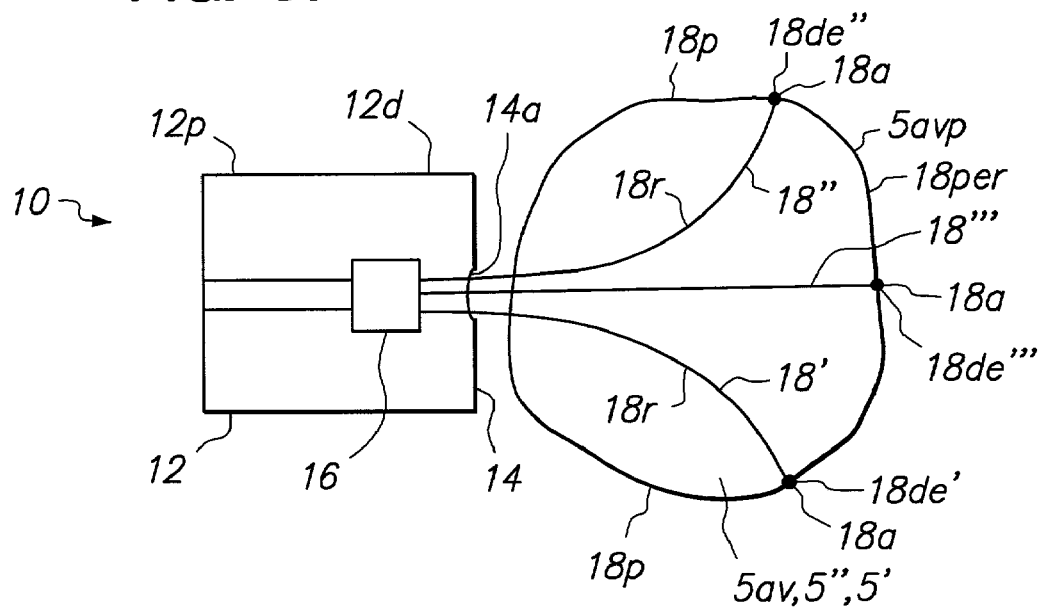
FIG. 37 is a lateral view illustrating an embodiment of the surface treatment apparatus having an array of electrodes.

Referring to FIG. 37 in an embodiment, electrodes 18 can comprise an array 18*a* of deployable electrodes positioned in housing 12. Electrode array 18*a* can include a first, second and third electrode 18, 18" and 18'" with other embodiments including 5, 7, 10, 15 and 20 electrodes. Electrodes 18', 18" and 18'" can have tissue piercing distal ends 18*de*' 18*de*", and 18*de*'" respectively. Electrodes 18', 18" and 18'" are selectably deployed with in straight fashion or with curvature from apertures 14*a* of tissue contact surface 14 to a selected tissue site 5'. Tissue site 5' can be any tissue mass and can be a tumor to be ablated. Electrodes 18', 18" and 18'" are selectably deployed to be controllably positioned at a desired location relative to tissue site 5' that includes internal placement, external placement at a periphery of tissue site 5' and at any desired location relative to tissue site 5'. The selectable deployment of electrodes 18' 18", and 18'" to create a desired pattern of ablation or ablation volume 5*av* can be achieved controlling one or more of the following parameters: (i) the amount of advancement of electrodes 18' 18", and 18'" from housing 12; (ii) the independent advancement of electrodes 18' 18", and 18'" from housing 12; (iii) the lengths and/or sizes of energy delivery surfaces of electrodes 18', 18" and 18'"; (iv) the variation in material properties (e.g. stiffness and column strength) used for electrodes 18' 18", and 18'"; and (v) variation of geometric configuration of electrodes 18' 18", and 18'" in their deployed states. Also, electrodes 18 can be deployed simultaneously, in pairs, in sets, and one at a time. Further, in various embodiments any number of electrodes 18 can be coupled to housing 12 for deployment.

In an embodiment, electrodes 18' and 18" can have a radius of curvature 18*r* in their deployed stated, while electrode 18'"

remains substantially straight or has less curvature than electrodes 18' and 18'. As all three (or more) electrodes are advanced into tissue the shape of their perimeter 18*per* or the perimeter 5*avp* of ablation volume 5*av* stays substantially the same (though it increases in size) independent of the amount of longitudinal deployment of electrodes 18' 18'', and 18''' relative to housing longitudinal axis. This scalability of ablation volume shape is also shown in U.S. application Ser. No. 09/148,571, Filed Sep. 4, 1998, which is incorporated by reference herein.

Figure 38A:
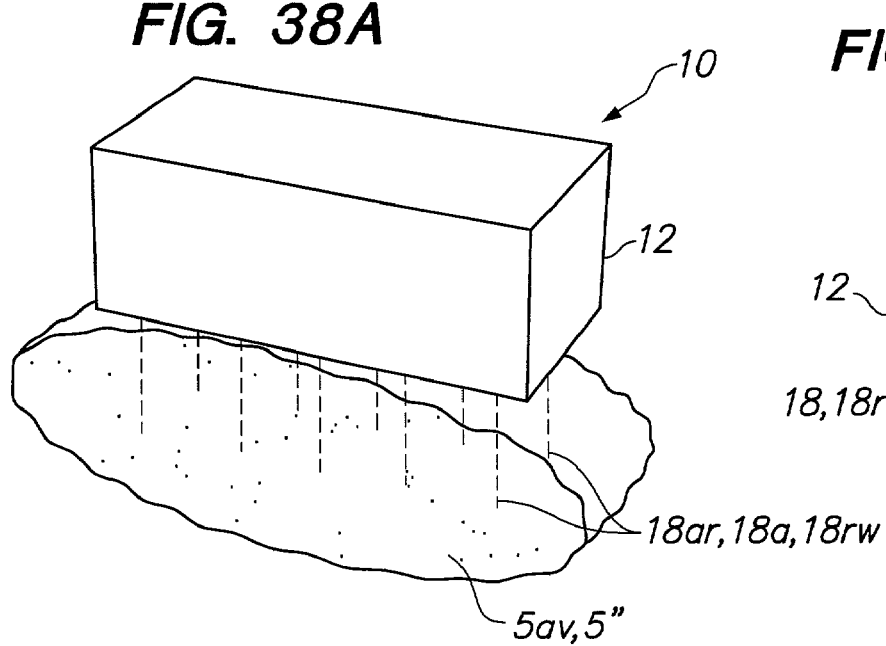
FIG. 38a is a perspective view illustrating an embodiment having a rectangular array of electrodes
Figure 38B:
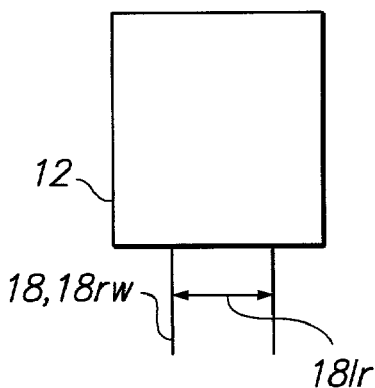

Referring to FIGS. 38*a* and 38*b,* in an embodiment of the apparatus electrode 18*a* can be configured as a substantially rectangular array 18*ar* having four or more electrodes 18. Housing 12 can also have a substantially rectangular shape. The rectangular array 18*ar* can comprise one or more rows of electrodes 18*rw* closely spaced, enabling the physician to create a narrow rectangular and precise ablation volume. Such spacing 18*lr* of electrodes rows can be in the range of 1 to 30 mms with specific embodiments of 10 and 20 mm. In use, embodiments of a rectangular array 18*a* would allow the physician to create a series of sectional ablation volumes which could be individually resected and/or biopsied.

Figure 39:
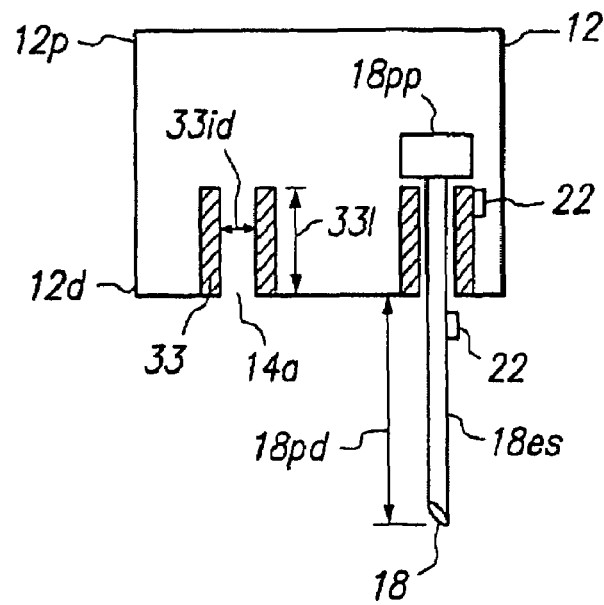
FIG. 39 is a lateral view illustrating an embodiment of the housing having a stop configured to control electrode penetration depth.
Figure 40:
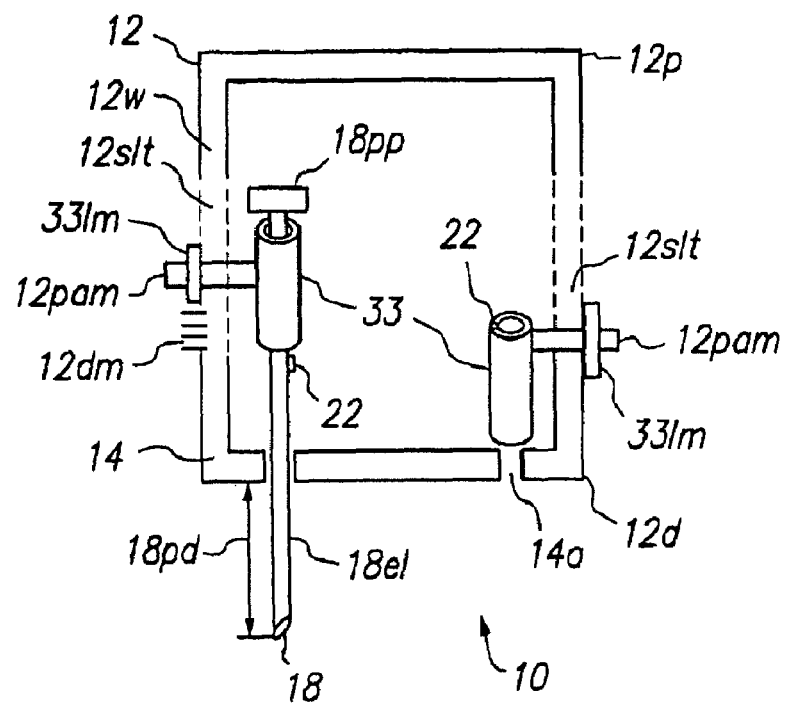
FIG. 40 is a lateral view illustrating an embodiment of the housing having a movably adjustable stop.

The tissue penetration depth of electrodes 18 can be controlled by a variety of means discussed herein including the use of a positioning fixture on the handpiece. Referring now to FIGS. 39–40, in various embodiments penetration depth 18*pd* can be controlled by a stop 33 positioned on or in housing 12. Stop 33 can be a mechanical stop configured to limit a longitudinal or other movement of electrode 18. Stop 33 can positioned in or on the proximal or distal portion 12*p* and 12*d* of housing 12. Further, stop 33 can be movably or fixedly coupled to housing 12 and can be integral to housing 12. In an embodiment shown in FIG. 39, stop 33 is a tubular sleeve of a set length 33*l* that is configured to be coupled to aperture 14*a* and has inner diameter 33*id* configured to allow the advancement of electrode elongated section 18*es* but stop or but up against proximal portion 18*pp*. The length 33*l* of stop sleeve 33 determines or limits electrode penetration depth 18*pd*. In an alternative embodiment, stop 33 can be a latch or clamp that protrudes from the housing wall 12*w* to make contact with proximal portion 18*pp* of electrode 18 having a larger diameter than distal the electrode section 18*ds*.

In a related embodiment shown in FIG. 40, stop sleeve 33 is configured to be movably adjustable (and hence, penetration depth 18*pd* as well) by being coupled to a lateral positioning arm member 12*pam* that is configured to be slidably movable within a longitudinal slot 12*slt* in housing 12. Positioning arm member 12*pam* can be fixed in particular longitudinal position within the slot using a locking mechanism/member 33*lm* such as a locking nut, clamp, or squeezable member. The exterior of slot 12*slt* can have depth/positional markings 12*dm* that are pointed to by arm member 12*pam* as the arm and coupled stop 33 are moved up and down in order to indicate the selected penetration depth 18*pd* to the user.

In related embodiments, penetration depth 18*pd* as well electrode position can also be ascertained through the use of one or more sensors 22 positioned on electrode 18, housing 12 or advancement member 16 on the proximal or distal portions of each. Suitable positional sensors that can be employed include LVDTS and positional sensors known in the art. Such sensors 22 could also be configured to determine, full electrode deployment, partial deployment and full electrode retraction with such conditions being indicated by an audio or visual signal on the display of a coupled power supply 20 or computer/control system 338/329 described further herein. A hall effect switch or other switch sensor 22, could be used to determine full deployment and full retraction. This and related embodiments provides the benefit to the user of being able to reliably ascertain full deployment of the electrodes in tissue site 5' without having to resort to an imaging device such as fluoroscopy which in turn reduces procedure time and exposure to ionizing radiation. Further, the embodiment of FIGS. 39 and 40 also provide the safety benefit of indicating to the user when the electrodes are fully retracted enabling apparatus 10 or housing 12 to be easily removed from the tissue surface without the risk of puncture injury to the patient or associated medical personnel.

Figure 41:
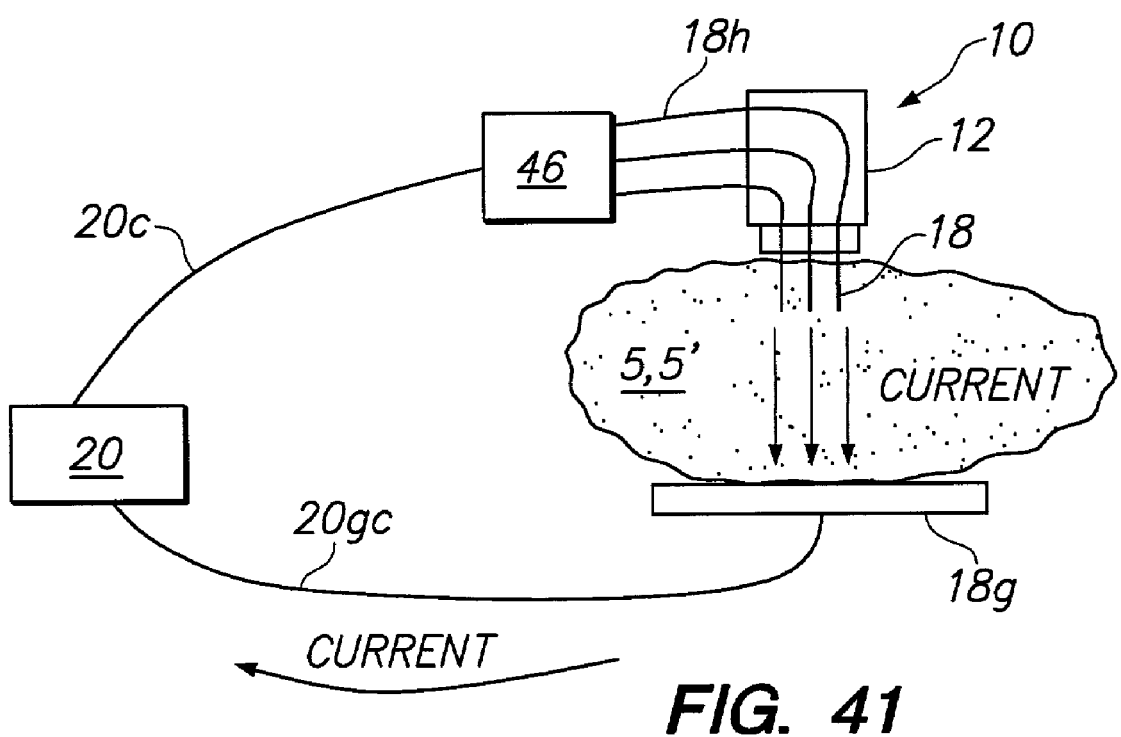
FIG. 41 is a schematic view illustrating an embodiment of the apparatus having multiplexed electrodes configured to produce spatial and temporal patterns of energy delivery.

Turning now to a discussion of the control of energy delivery by electrodes 18, in various embodiments such control can be achieved via the multiplexing of one or more electrodes 18. Referring to FIG. 41, in an embodiment one or more wires 18*h* may be coupled to a multiplexing device 46 or other switching device known 46 in the art coupled to power supply 20, allowing energy to be delivered to selected electrodes to achieve a desired spatial pattern of active electrodes or temporal pattern of or a combination of both. Spatial patterns can include circular, semicircular, oval, crescent, rectangular and triangular. Temporal patterns can include pulsation, a square wave function, a sinusoidal function and combinations thereof.

Figure 42:
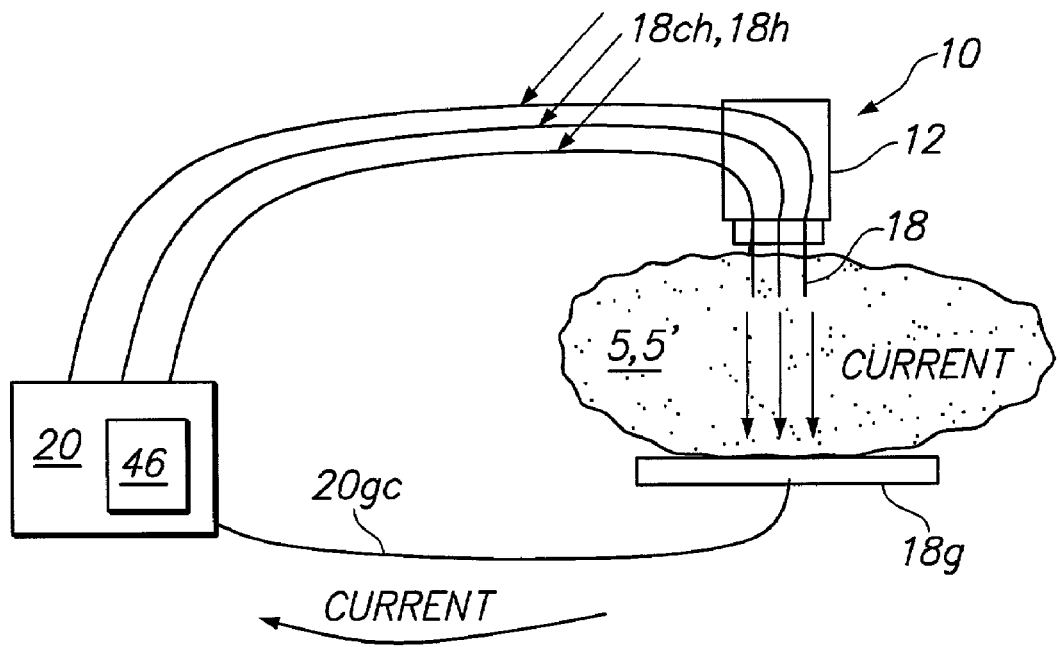
FIG. 42 is a schematic view illustrating an embodiment of the power supply having multiple independent channels to each electrode.

Referring to FIG. 42, in a related embodiment RF power source 20 can have multiple independent channels 20*ch,* delivering separately modulated power to each RF electrode 18. This can be accomplished through the use of separate channels 20*ch* in a parallel connection or timesharing on the same channel using a switching device or multiplexing device 46 and a serial connection or a combination of both. Such configurations reduces preferential heating that occurs when more energy is delivered to a zone of greater conductivity and less heating occurs around RF electrodes 18 which are placed into less conductive tissue. In use, a multichannel RF device 20 produces more uniform tissue ablations by solving the problems of uneven or time varying amounts of tissue hydration or blood perfusion over the target tissue site 5' which tend to cause uneven conductivity and tissue heating.

Figure 43:
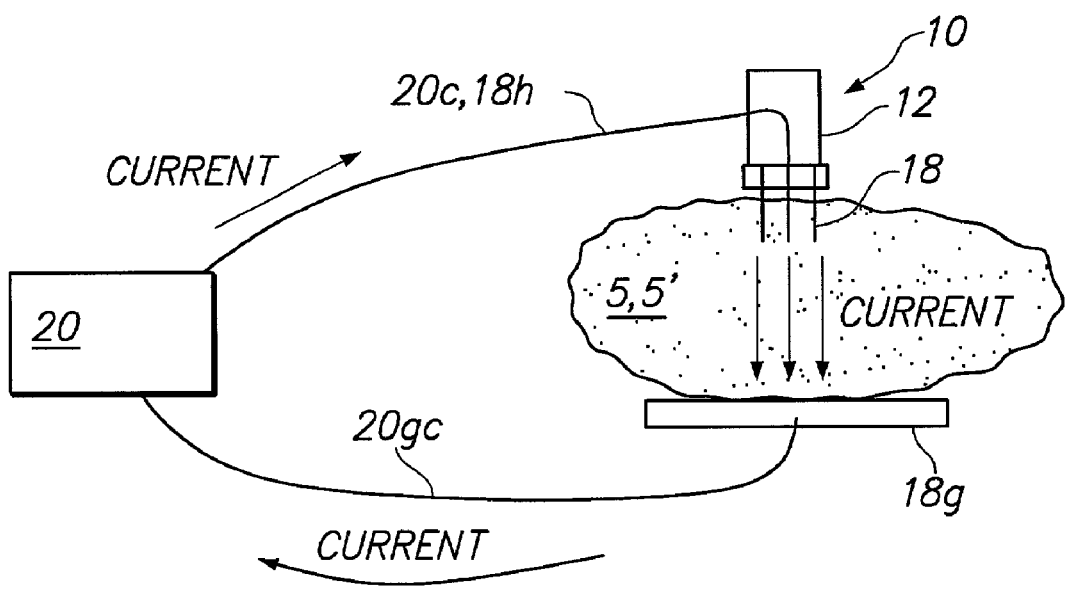
FIG. 43 is a schematic view illustrating use of a ground pad electrode for monopolar embodiments of the invention.

In various embodiments, electrodes 18 can be operated in a monopolar mode, a bipolar mode, or a combination of both and can be switchable between the two. Referring now to FIG. 43, when electrodes 18/apparatus 10 are operated in a monopolar mode, an indifferent electrode patch or ground pad 18*g* (also called a return electrode) is attached to the patients skin using known methods (e.g. use of a conductive gel) and is also electrically coupled to power source 20 by a cable 20*gc* or other connecting means. Ground pad 18*g* serves to complete an electrical circuit between one or more electrodes 18, the tissue site 5' and the power source 20. Ground pad 18*g* can be ground pad known in the art and can be made of a flexible material such as a resilient polymer and can include a smooth, texturized or ridged surface. Ground pad 18*g* has sufficient area to keep the current density at the point of contact with the patient to low enough to prevent any appreciable heating of the patient's skin. The ground pad can be an area in the range of 0.5 to 3 square feet, with specific embodiments of 1, 2, and 2.5 square feet. The use of a texturized or ridged surface serves to increase the amount of pad surface area in electrical contact with tissue and thus reduce current densities and reduce the risk of pad burns.

Figure 44A:
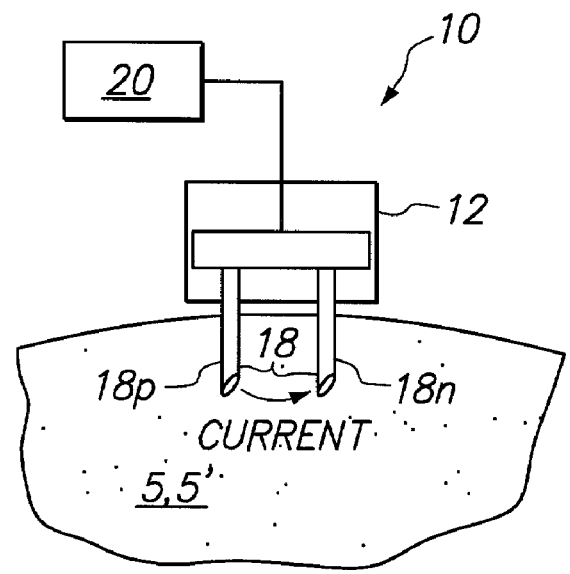
FIGS. 44a–44c are schematic views illustrating configurations of the electrodes in bipolar embodiments of the invention.
Figure 44B:
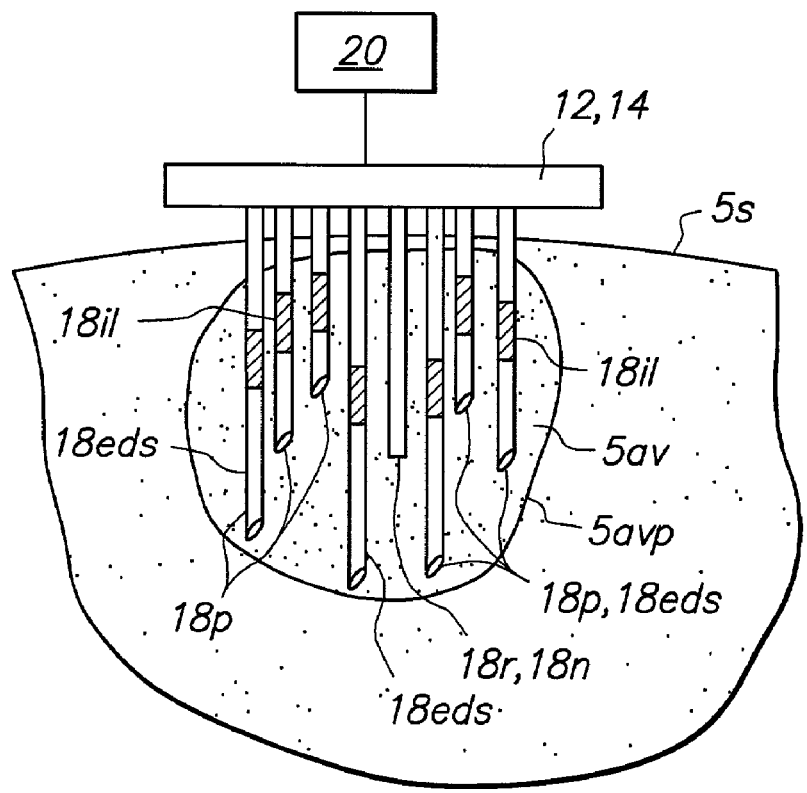
Figure 44C:
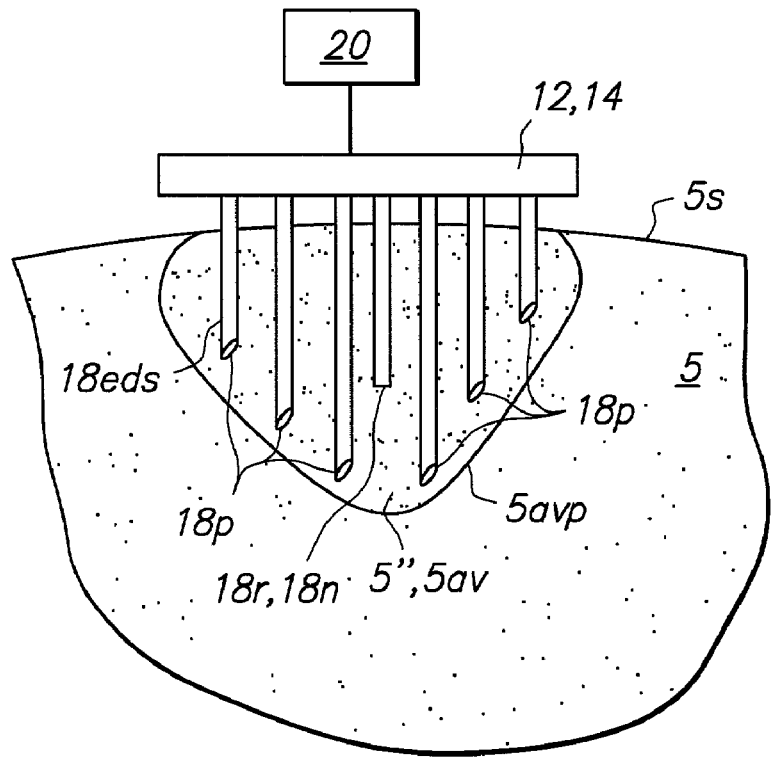

Referring now to FIGS. 44*a*–44*c*, in various embodiments, one or more electrodes 18 coupled to housing 12 can be operated in a bipolar mode. Bipolar mode includes at least two electrode including one electrode that acts as a positive electrode 18*p* and another electrode 18*n* such that current flow from electrode 18*p* to 18*n*. Electrode array 18*a* can be configured with any number of positive or negative electrodes 18p and 18n as long as there is at least one of each. One configuration shown in FIG. 44a includes a single positive and negative electrode 18p and 18n. Other configuration can include multiple positive electrodes 18p and only one negative electrode 18n or multiple positive and multiple negative electrodes. Tissue heating is localized and occurs adjacent both the positive and negative electrodes. The selection of positive and negative electrodes can be configured to control the area of heating to match the tumor shape and also minimize heating of surrounding tissue. In one embodiment shown in FIG. 44b, return electrode 18n is located at the center or locus of circular or other geometric pattern of positive electrode 18p such that heating and the ablation volume 5av are substantially confined to the area bounded by the perimeter of the group of positive electrodes. In another embodiment shown in FIG. 44c, the pattern of positive electrodes is arc shaped again with the return electrode located at the locus of the arc such that a pie shaped ablation volume 5av is produced. This ablation volume can be at least partly bounded by tissue surface 5s or tissue proximate surface 5s.

Figure 45:
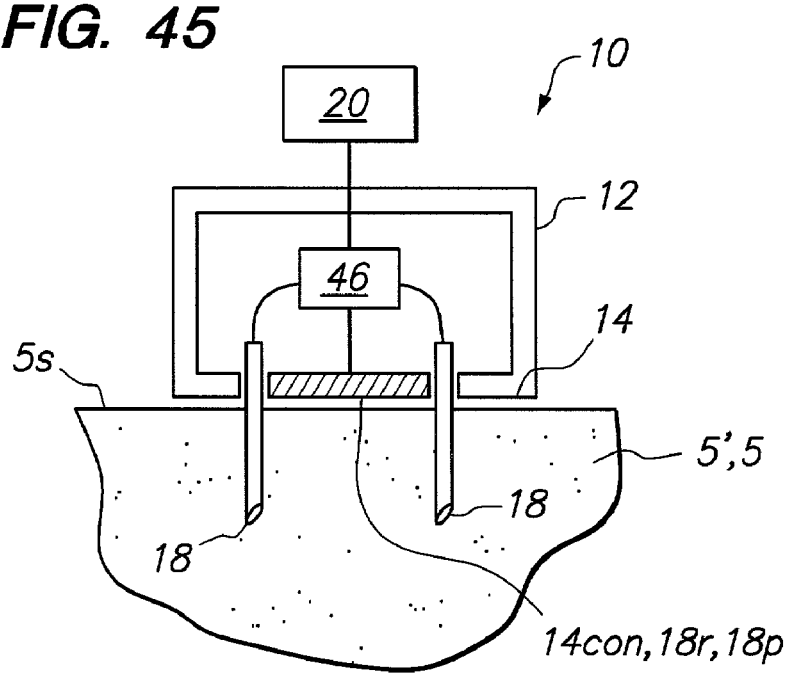
FIG. 45 is a schematic view illustrating an embodiment of tissue contact surface having a conductive tissue portion employed in monopolar and bipolar modes.

Referring to FIG. 45, all or portions of tissue surface 14 can be a conductive surface 14con configured as the either the energy delivery electrode or the return electrode. This can be accomplished by fabricating surface 14 from conductive materials, coatings, or from porous material configured to contain and or weep a conductive fluid film both configurations described herein. In various embodiments conductive surface 14con can be configured as a monopolar positive electrode, a monopolar return electrode or bipolar electrode. Switching between these different modes can be accomplished through the use of a switching device 46 such as a multiplexing device or programmably switching device coupled to one or more conductive surface 14con, electrodes 18 and power supply 20.

Figure 46:
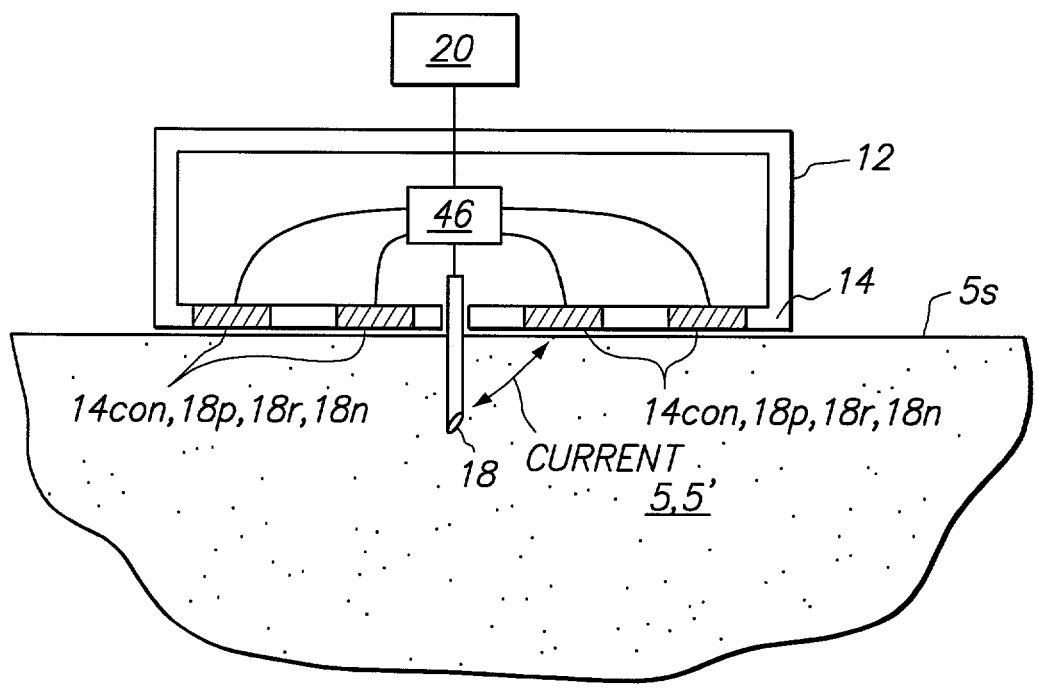
FIG. 46 is a schematic view illustrating an embodiment of the tissue contact surface having multiple conductive portions.

Referring to FIG. 46, in a related embodiment conductive surface 14con can comprise one or more conductive areas 14cona which can each be individually controlled to an on/off state using a coupled multiplexing or switching device 46. The use of switching device 46 allows the user to dynamically increase or decrease the conductive area 14con of contact surface 14 to do one or more of the following: (i) adjust the area of conductive surface 14 con as an energy delivery electrode or return electrode to compensate for changes in tissue impedance; (ii) adjust the area of tissue heated; (iii) adjust the rate of tissue heating; and (iv) adjust the area of area of conductive surface as a return electrode in order to prevent thermal damage to non-target tissue including coagulation of blood vessels such as the hepatic vein.

Figure 47:
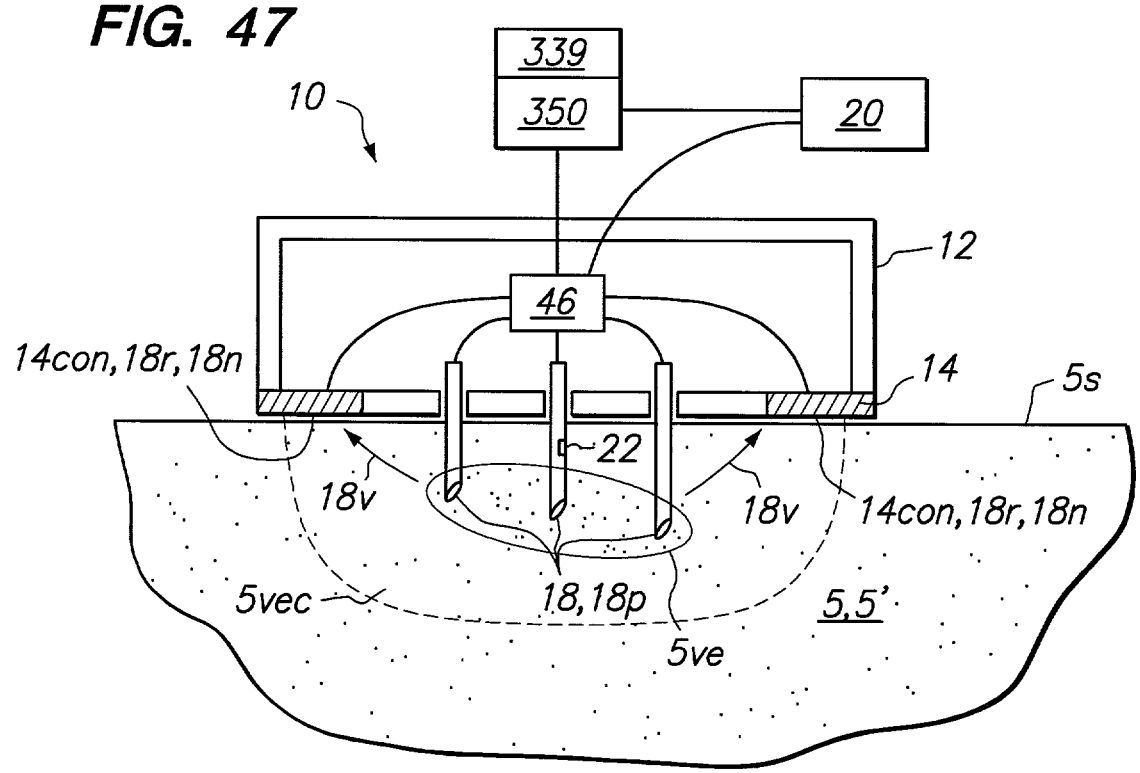
FIG. 47 is a schematic view illustrating an embodiment of a conductive tissue contact surface used to generate and control a current/energy vector within the target tissue volume.

When used as the positive electrode or the return electrode, conductive contact surface 14con can be configured to evenly deliver energy to tissue surface 5s in electrical contact with contact surface 14 and so as to generate a more uniform thermal profile within target tissue volume 5" and hence a more uniformly necrosed and ablated tissue volume. Similar benefits can be obtained for use of a conductive fluid film 14f described herein Referring to FIG. 47, in related embodiments employing a conductive contact surface 14con, one or more conductive portions 14con can be selected as an electrode, including a return electrode 18r or 18n and one or more electrodes 18 can be selected as the positive electrode 18p, using switching device 46 and so create a selectable composite vector(s) 18v of current or energy into target tissue 5' having a selectable direction and magnitude. The selection and configuration of electrodes 18 to produce a given vector 18v can be controlled by logic resources 350 coupled to switching device 46 which can be a multiplexing device. The vector 18v can be in the volume 5ve defined by deployed electrodes 18, or the volume 5vec deployed electrodes 18 and conductive surface 14con. In use, this approach allows the physician to more precisely control or titrate the delivery of RF or others electromagnetic energy to yield higher current densities and hence temperatures in selected portions of the target tissue volume and lower current densities in other selected areas. This configuration in turn provides benefit of providing a higher degree of cell necrosis/ablation with a lower risk of tissue desiccation and excessive impedance build up.

Figure 48:
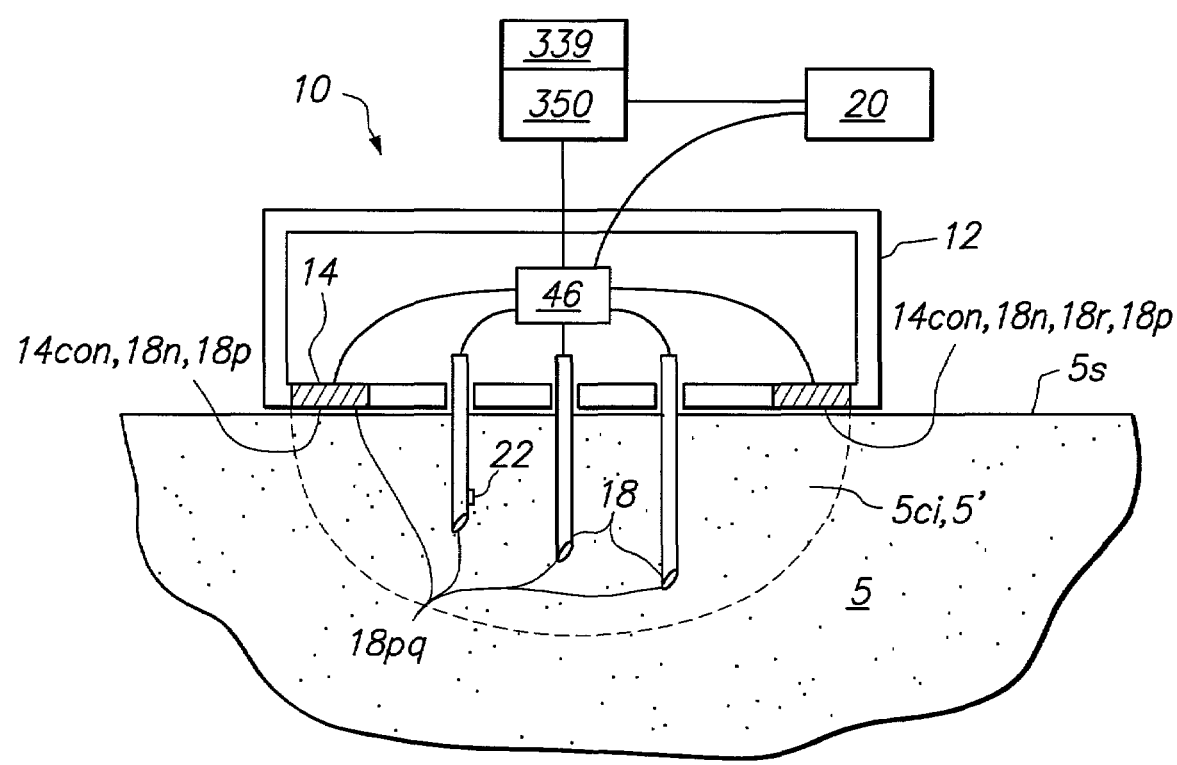
FIG. 48 is a schematic view illustrating an embodiment of the surface treatment apparatus having a phased array of electrodes.

Referring to FIG. 48, in another embodiment one or more electrodes 18 and/or conductive surface 14con can be configured to produce a phased array of RF electrodes 18pa to obtain a zone or area of constructive signal interference 5ci within target tissue volume 5' under tissue surface 5s and hence an enhanced thermal effect with more rapid tissue heating and necrosis. Phased array embodiments can include use of conductive surface 14con as either a positive electrode 18p or return electrode 18r. Electrodes 18 and/or conductive surface 14con can be coupled to a controller 339 described herein having logic resources (e.g. a microprocessor) 350 that adjusts the feedback signal, with a gradient search or matrix inversion algorithm known in the art, to provide a uniform electric field radiation into the target tissue site 5ci.

Figure 49A:
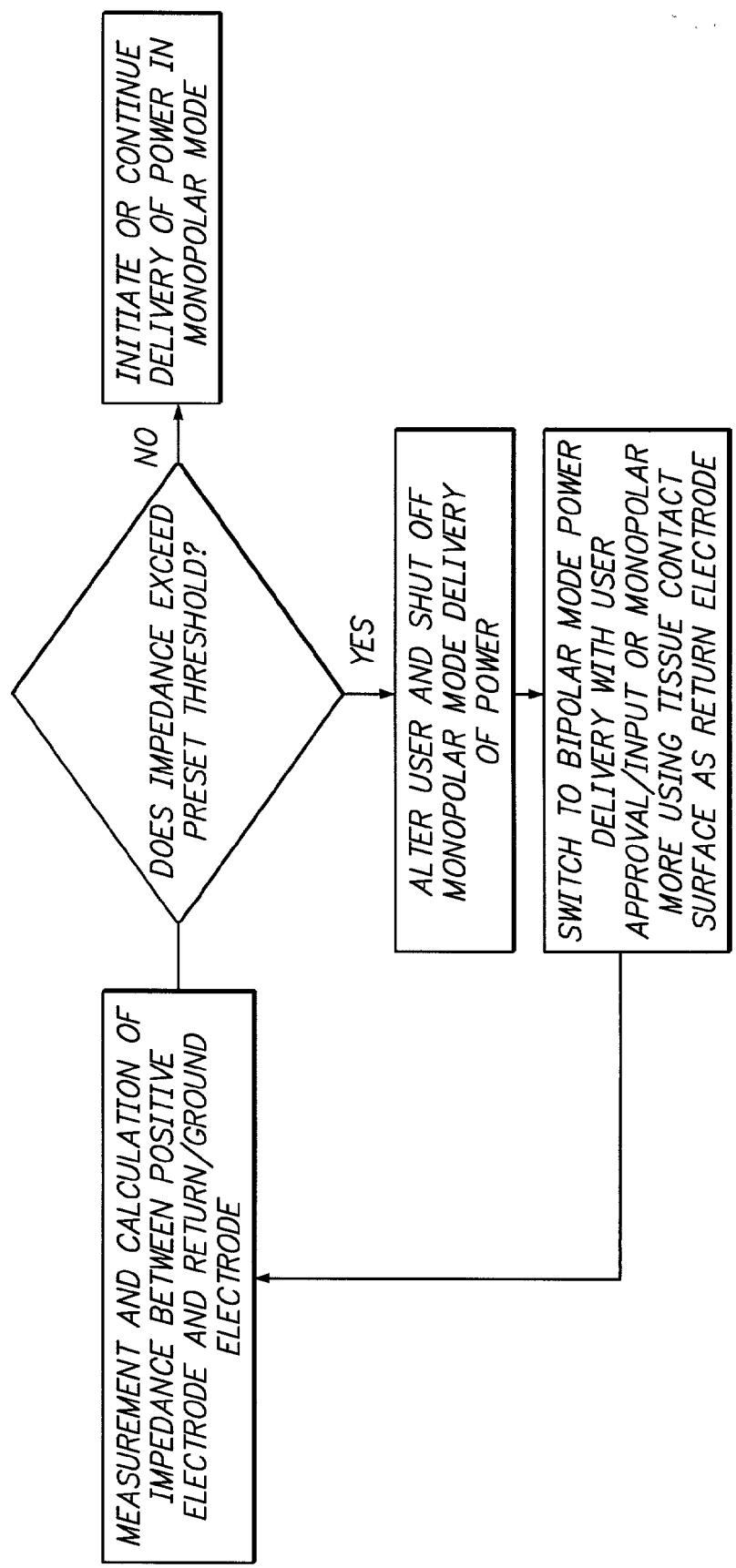
FIG. 49*a* is a flow chart illustrating an embodiment of a method of the invention utilizing an algorithm to switch between monopolar and bipolar modes based on measurement of tissue impedance.
Figure 49B:
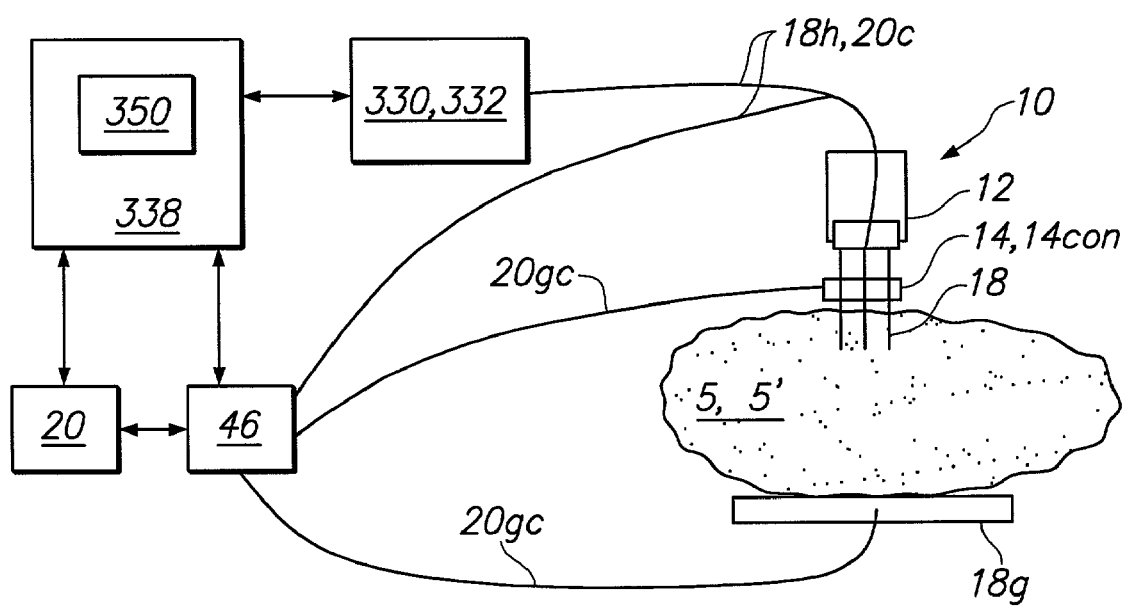
FIG. 49*b* is schematic view of an embodiment of an apparatus for performing the method of FIG. 49*a*.

Depending upon the location of the tumor it may be advantageous to operate in a bipolar mode so as not to have the return electrical current flow through a narrowed or small portion of the liver where the tissue impedance can be great enough to cause a temperature increase sufficient to coagulate or damage the hepatic vein or other hepatic vasculature. Accordingly, referring to FIGS. 49a and 49b, in an embodiment impedance measurement circuitry and/or controller/logic resources 339/350 (coupled to power source 20) can be configured to determine if the return path impedance is sufficient to cause heating anywhere along the return path and automatically switch into a bipolar mode either prior to energy delivery or once such impedance or resulting temperature exceeds a preselected threshold. In a related embodiment, thermal, flow and coagulation sensors 22 can be positioned in the hepatic vasculature within target site 5' or nearby tissue. Sensors 22 can monitor both the temperature of the hepatic vasculature as well as monitor blood flow rates there through the hepatic vasculature. Again sensors 22 are coupled to logic resources which switch from a monopolar to a bipolar mode, shut off or otherwise attenuate the delivery of power to target site 5' when: (i) the tissue temperature exceeds an absolute threshold or a rate of increase; (ii) the blood flow rate falls below an absolute threshold or a rate of decrease; or (iii) a combination of items (i) and (ii). In these and related embodiments, sensors 22 can be positioned on electrode 18 or passive non energy delivering members which can be positioned at varying distances from energy delivery devices 18 so as to be to passively monitor tissue temperatures at selected distances from electrode 18. Sensors 22 can be electronically coupled to logic resource in turn coupled to power source 20. Such resources can include microprocessors containing embedded modules or software programs. Such microprocessors can include an Intel® Pentium® III chip or a PowerPC® chip manufactured by the Motorola Corporation. Such resource can also contained embedded control modules that include process control algorithms known in the art such as PID algorithms. The switching between monopolar to bipolar modes can be achieved by the use of switching circuitry 20s including multiplexer devices (including a densely packed wavelength multiplexor) coupled to one or more electrodes 18 as wells as return electrode 18r and tissue contact surface 14 including conductive portions 14*con*. Switching to bipolar mode also serves to keep RF induced heating closer to tissue surface 5*s* thus preventing the unwanted heating of deeper tissue containing healthy tissue and/or thermally sensitive structures. Thus in use, embodiments having the ability to have feedback control to switch between monopolar and bipolar modes present the advantage of more refined and faster control over the depth of tissue heating to prevent thermal injury of underlying healthy/sensitive tissue without having to reposition the electrodes.

Figure 50A:
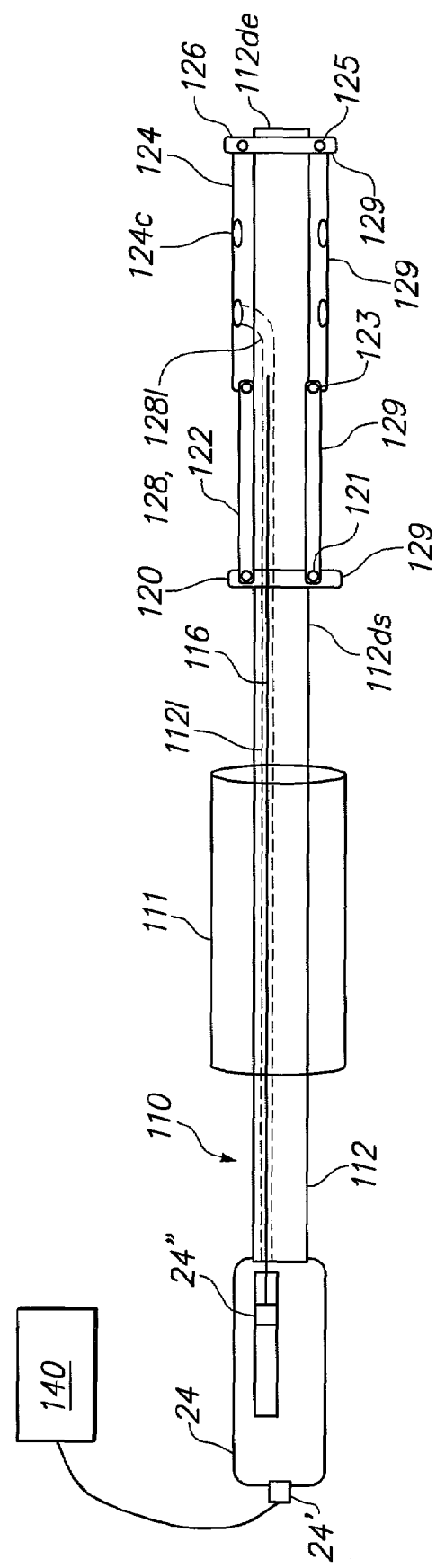
FIGS. 50*a* and 50*b* are lateral views illustrating embodiments of a collapsible strut surface treatment apparatus in a non-deployed and deployed state having a fixed distal hub.
Figure 50B:
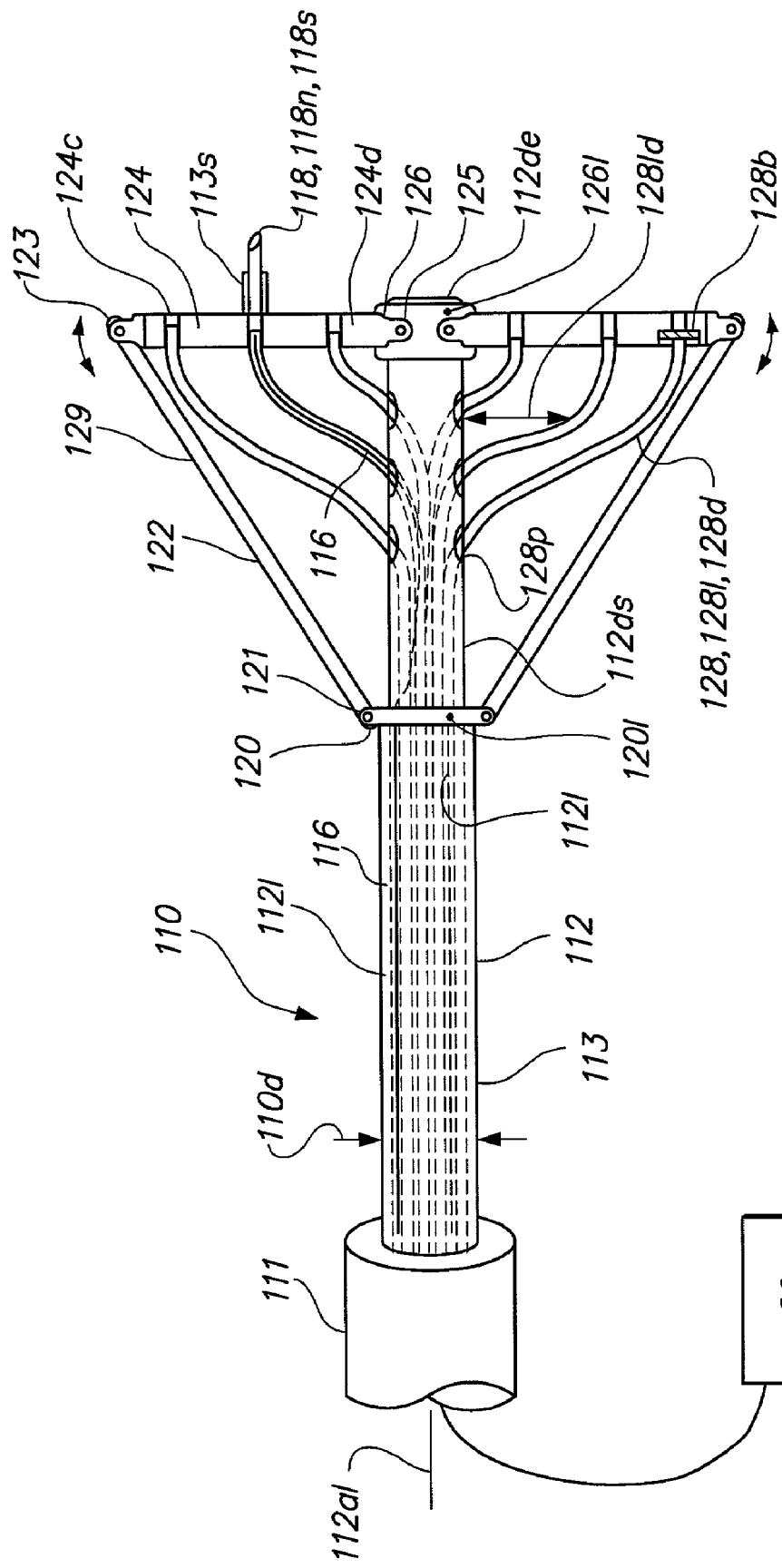
Figure 51:
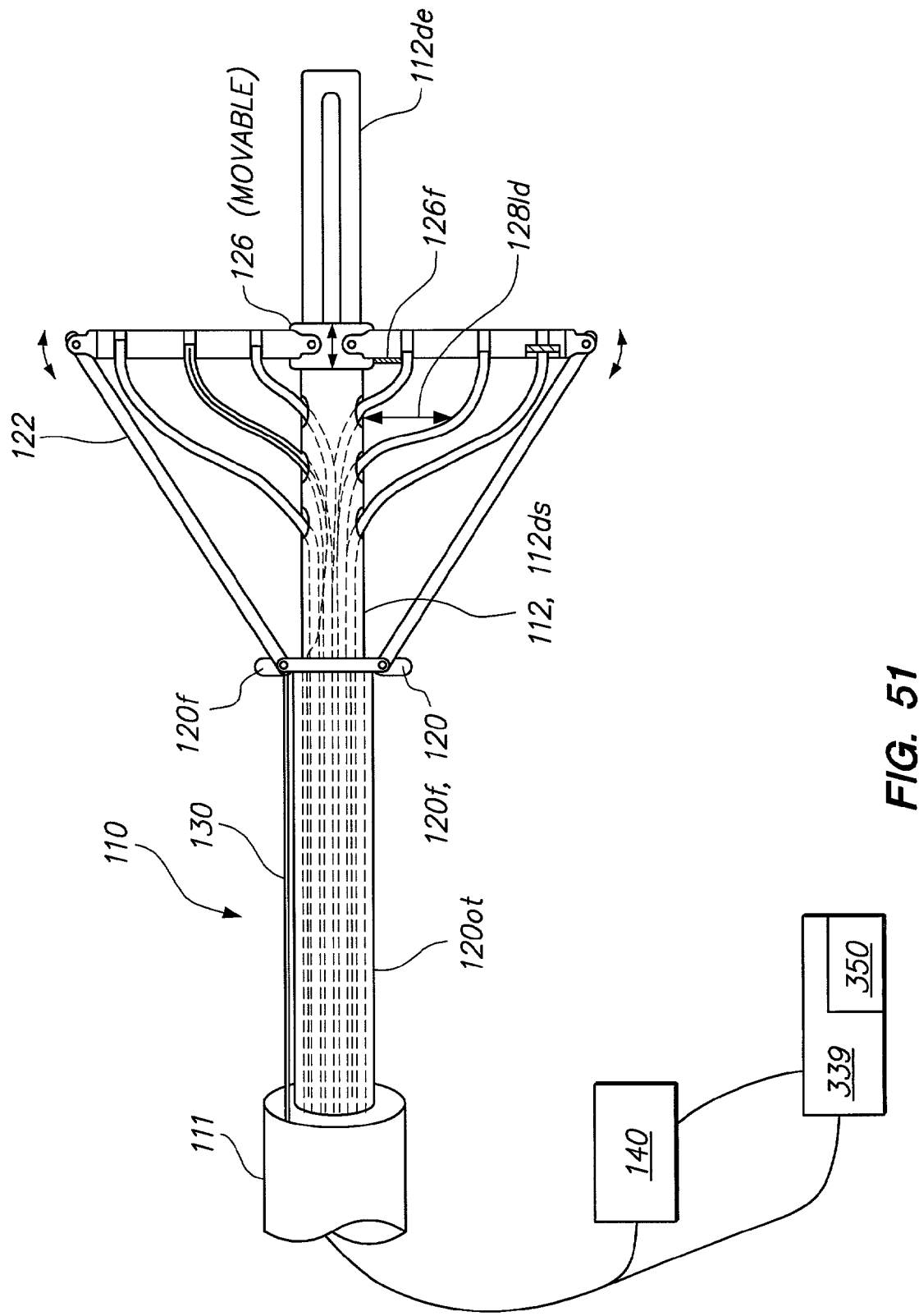
FIG. 51 is a lateral view illustrating an alternative embodiment of the collapsible strut surface treatment apparatus having a movable distal hub.

Referring to FIGS. 50*a*, 50*b* and 51, in another embodiment of the invention surface treatment apparatus 10 can comprise a collapsible strut apparatus 110 configured to be coupled to power source 20. Collapsible apparatus 110 can be configured to positionable within an endoscopic or a surgical introducing device 111 such as an endoscope, trocar and the like. Collapsible apparatus 110 has a collapsed or non deployed position shown in 50*a* and a deployed position shown in FIG. 50*b*. Collapsible apparatus 110 includes a central elongated or shaft member 112 having a distal section 112*ds* including a end 112*de*. A needle electrode 118*n* can be fixedly or movably attached to tip 112*de*. Also shaft member 112 can include a lumen 112*l* which can be configured to allow the advancement of a rigid or a flexible advancement member 116. Advancement member 116 can be flexible or rigid and can be guide wire, hypotube, or polymer shaft all having sufficient column strength to advance a distally coupled needle into tissue. Advancement member 116 can be coupled to a needle electrode 118*n* to allow its advancement into tissue.

A movable proximal hub 120 is slidably positioned over shaft 112 and is configured to slides over distal section 112*ds* and can be releasably locked in position in position using a first locking device 120*l* which can be a latch, locking nut or clamp known in the art. A distal hub 126 is positioned over distal end 112*de* and preferably is fixedly mounted. However the longitudinal position of hub 126 with respect to shaft longitudinal axis 112*al* can be adjusted using a second locking device 126*l*. Alternatively, in embodiment shown in FIG. 51, distal hub 126 can be movable and proximal hub 120 can be fixed. Also, proximal hub 120 can comprise an overtube 120*ot* that is slidably positioned over shaft 112. Both of hubs 120 and 126 can be configured to be advanced and retracted by a coupled guidewire or other mechanical linkage known in the art. In an embodiment one, or both of hubs 120 and 126 can include a flange 121*f* or 126*f* that enables one or both hubs to be pushed (advanced) and pulled pack via means of either stiffened guide wires mechanically coupled (e.g. by welding) to either flange or a hollow advancement tube member 130 that is coupled to or otherwise pushes up against either flange. In yet another embodiment, either flange 121*f* or 126*f* can be configured to act as pneumatic or fluidic seal against the lumen of an overlying introducer 111 such that either hub can be and retracted so as to deploy and retract electrodes 118 pneumatically or hydraulically using an air or fluid pressure source 140 known in the medical device arts. An example of air pressure source includes a tank of compressed gas and a fluid pressure source includes a syringe pump.

A plurality of strut members 122 are pivotally coupled to hub 120 using a pivotal connector 121 which can be a hinged bracket, clamp or other connector known in the art. A second pivotal connector 123 is coupled to the distal end of each strut member 122. A second strut member 124 is pivotally coupled to each connector 121 so as to comprise a plurality of second strut members 124. The distal end 124*d* of each second strut member 124 is pivotally coupled to a third pivotal connector 125 in turn coupled to fixed hub 126.

A flexible guide tube member 128 is coupled to first strut member 122 preferably at pivotal joint 121. In a specific embodiment, guide member 128 is coupled to a channel or slot 124*c* on or adjacent second strut 124. Channel 124*c* can be semicircular, sector or u-shaped to mate and hold guide 128 using an interference fit or adhesive bond. Guide tube member 128 has a lumen 128*l* for positioning and advancement of an electrode 118 by a coupled advancement member 116 or other mechanical means. Guide tube can 128 also be coupled to a tube bracket 128*b* on strut 124. When in the non-deployed state, guide tubes 128 are in proximity to shaft member 112 substantially parallel to axis 112*al*. However, in the deployed state guide tubes 128 are pushed out a lateral distance 128*ld* from shaft 112 at channel 124*c* by the deployment of coupled strut members 122 and 124 such that guide member now assumes a curved shape going from proximal hub 120 to its coupling at channel 124*c*. The curve can have one or more radii of curvature and can be s-shaped. However though curved in portions, guide tube 128 is configured to be substantially parallel to axis 112*al* such that electrodes 118 exiting deployed guide tubes 128 are also substantially parallel to axis 112*al*. This can be achieved by configuring or shaping the distal end of guide tube 128 to curve at least partly inward in the non-deployed state. This can be achieved using metalworking techniques known in the art including mandrel shaping, and also through the use of shape memory materials.

Collectively hub 120, strut members 122, connectors 123, strut members 124, connector 125, hub 126 and the distal portion 112*ds* comprise an expansion device 129 that is used to put apparatus 110 in its deployed state. Apparatus 110 can be put into its deployed state by either the distal advancement of hub 120, when hub 126 is fixed, or the proximal retraction of hub 126 when hub 120 is fixed. In the non deployed state apparatus 110, including the coupled combination of shaft 112, strut 122, strut 124 and guide tube 128 has a cross sectional profile that can be advanced through a standard sized endoscope or trocar (or other surgical introducer), including endoscopes having an internal diameter in the range of 0.1 to 1.0 inch with specific embodiments of 0.2, 0.5 and 0.8 inches. In a preferred embodiment, apparatus 110 is configured to be advanced through an introducing device 111 having an inner diameter of 1 cm thus the maximum radial profile or diameter 110*d* of apparatus in the nondeployed state is less than 1 cm, preferably by 0.002 or more to have 0.001" clearance on either side of apparatus 110 within the introducing device.

When in the deployed state, the linked struts 122 and 124 of expansion device 129 expand out laterally in a triangular shape to push guide tubes 128 out laterally in a substantially, triangular, diamond circular or oval pattern having shaft 120 as its center so as to enable electrodes 118 contact tissue surface 5*s* in such a pattern.

Turning now to a discussion of the materials of apparatus 110, shaft member 112 and advancement member 116 can be fabricated from metals such as 304 stainless steel or Nitinol and the like or a rigid polymer such as a thermoset plastic, NYLON, ULTEM® , polyimide and the like. Also all or portion of shaft 112 can have an insulative (both electrical and thermal) coating 113 which can include TEFLON® , polyimide, or silicone. Coating 113 can also be a lubricous coating such as TEFLON® which serves to reduce the friction of moving components and tissue in contact with shaft 116. The interior of lumen 112*l* as well as advancement member 116 can also have coating 113. Similarly advancement member 116 can have an insulative coating 113 which can be in the form of a movable sleeve 113*s* so as to expose and/or create an energy delivery surface 118*s* of electrode 118. Sleeve 113*s* can be mechanically linked to a coupled mechanical actuator 24" on handpiece 24 which can be coupled to shaft member 112. Struts 122 and 124 can be rigid or flexible and can be constructed from 304 or 304vstainless steel (for both rigid and flexible embodiments) and shaped memory metals such as Nitinol for flexible embodiments. Pivotal joints 121, 123 and 125 can be fabricated from machined or forged metals including 304 stainless steel and hardened tool steel. They can also include hinged, swaged, ball bearing or roller bearing pivot mechanisms known in the art. Guide tubes 128 can include rigid and flexible portions and can be fabricated from metal hypotubes which can be made from shape memory materials or high strength and/or resilient polymers such as polyimide, PEEK™, HDPE, (including radiated materials), PEBAX®, polyurethane and ULTEM®. Additionally, the distal portions 128d of guide tubes 128 can be more flexible than proximal portions 128p in order to assume a curved shape in the deployed state and then reassume a substantially linear shape in the non-deployed state. Accordingly the distal section 128d can be made from flexible polymers such as polyurethane and can have a smaller diameter versus proximal portions 128p.

In an alternative embodiment, one or more of struts members 122 and 124 can be configured as fluidic or hydraulic strut members and can be configured to be deployed via the application of fluidic or pneumatic pressure from a pressure source 140 described herein. This can be achieved by configuring one or more strut members 122 and 124 as hollow (single or multi-lumen) or porous tubular members or catheters fabricated from resilient/inflatable polymers described herein.

Figure 52:
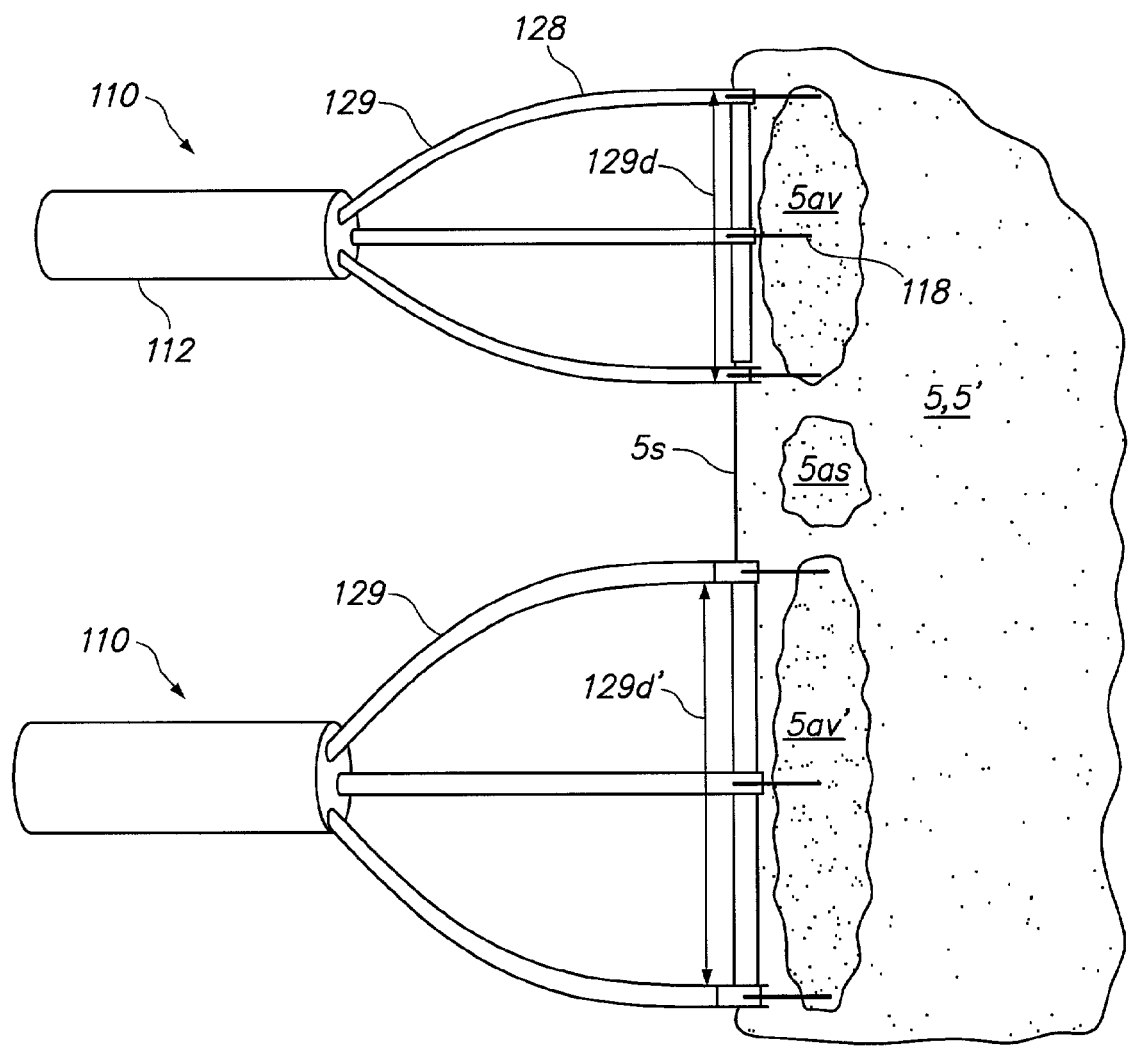
FIG. 52 is a lateral view illustrating the use of the embodiment of FIG. 50*b* or FIG. 51 to produce multiple ablation volumes.

Collapsible apparatus 110 and its methods of use provide the benefit of allowing the physician to treat varying portions of a tumor mass 5" as well as multiple tumor masses without having to significantly reposition the device using either open surgical procedures or endoscopic or other minimally invasive methods. This is due to the ability of apparatus 110 to have its electrode 118 be deployed at varying depths and varying locations without having to significantly reposition the apparatus. Referring now to FIG. 52, in an embodiment of the method of the invention, the physician would position apparatus 110 at the target tissue site 5' deploy the expansion device 129 to a selected first deployed diameter 129d' and deploy one or more electrode 118 through guide tubes 128 and deliver RF energy to produce the desire ablation volume 5av. Having done so, the physician would withdrawal deployed electrode 118 back into the guide tubes 128 and then expand or contract expansion device 129 to a second diameter 129dd" and redeploy one or more electrodes 118 and deliver RF energy to produce a second ablation volume 5av' or expand the first volume 5av. In this way the physician can avoid a critical anatomical structure 5as positioned within a target tissue site 5' including within a tumor mass 5" or between two or more nearby tumor masses 5". This method also provides the benefit of producing larger ablation volumes without the risk of impedance related shut downs, due to excessive tissue desiccation and impedance buildup in the core of the ablation volume 5avc which is continuously heated if the electrodes are not redeployed during the delivery of RF or other energy.

Figure 53A:
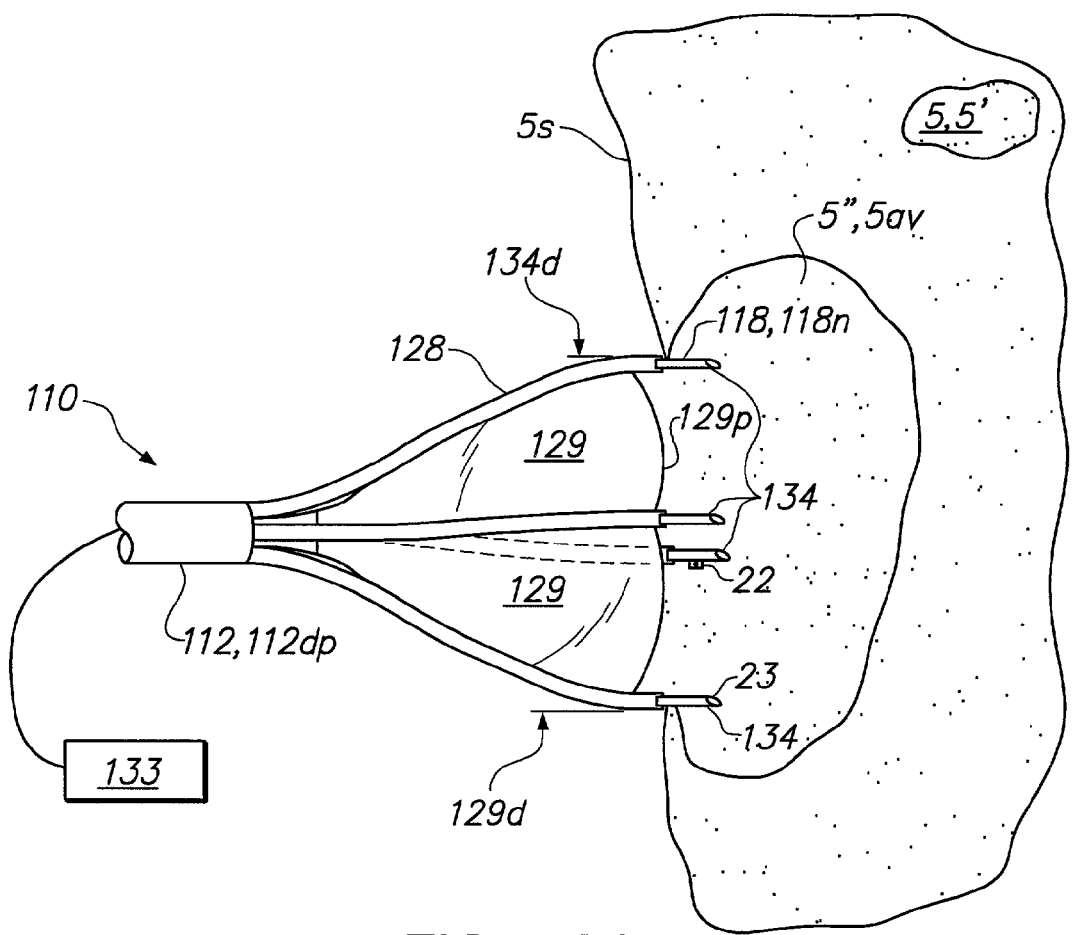
FIG. 53*a* is a lateral view illustrating an embodiment of a collapsible surface treatment apparatus utilizing an expandable balloon device.
Figure 53B:
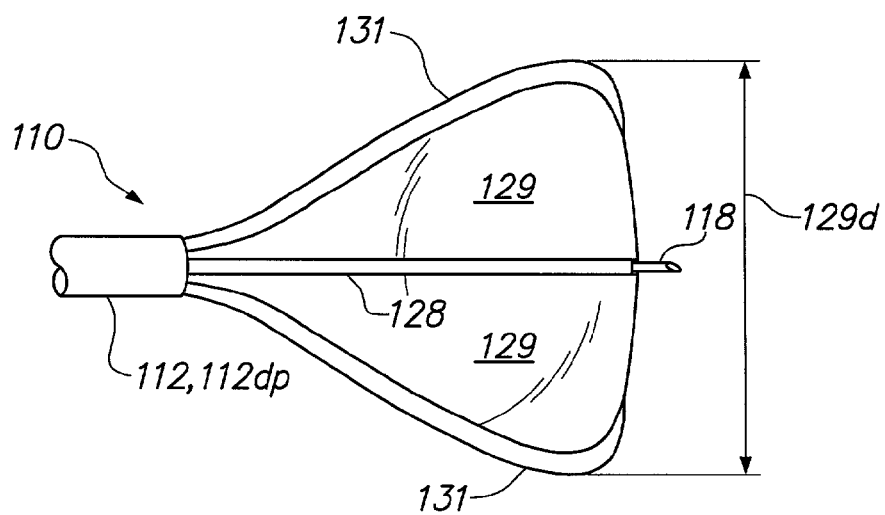
FIG. 53*b* is a lateral view illustrating an embodiment of a collapsible surface treatment apparatus utilizing an expandable balloon device with a restraining member.

Referring now to FIGS. 53a and 53b, in an alternative embodiment expansion device 129 can comprise an expandable balloon device known in the art such as a dilatation balloon known in the art. Guide tubes 128 can be distributed along a perimeter 129p or a portion thereof of balloon device 128. Balloon device 129 can be coupled to guide tubes 128 using adhesive bonding and other polymer bonding methods known in the art (or alternatively balloon device 129 and guide tubes 128 can be integrally formed). Balloon 129 is expanded to a selectable diameter to achieve a selected spacing or diameter 134d of a geometric shape whose perimeter is defined by deployed guide tubes 128. The shape or diameter of this shape in turn defines the collective shape or pattern 134 of deployed electrodes 118. The degree of inflation of balloon 129 can be used to match the diameter of deployed shape 134 to that of the tumor mass 5" or selected target tissue site 5'.

Balloon device 129 can be a balloon catheter or other inflatable device known in the art made from balloon materials known in the medical device arts including non-compliant materials such polyester, polyethylene (HDPE including radiated HDPE) latex and compliant material including silicones, polyurethane and latex. Balloon device 129 can be fabricated using balloon blowing methods known in the art including the use of mold blowing methods.

In an embodiment the maximum inflated diameter 129d of balloon can be selectable and can include diameters in the range of 0.1 to 3 inches with specific embodiments of 0.25, 0.5, 0.75 1, 1.5, 2 and 2.5 inches This can be achieved through the use of non-compliant balloon materials blown in fixed balloon molds of set diameter. The maximum diameter can also be achieved through the of E-beam irradiation (either before or after balloon fabrication) to cross link the polymer chains of the balloon materials such as HDPE and so fix the maximum amount of their expansion.

Balloon 129 can have a variety of shapes including but not limited to spherical, oval, a tapered oval and cylindrical. In a specific embodiment balloon is a disk shaped (e.g. a short cylinder) balloon. Such balloons can be fabricated using disc shaped molds. They can also be fabricated by irradiating the top and bottom faces of the balloon making them hold a shape (e.g. non compliant due to cross linking) while the sides of the balloon that are joined to guide tubes 128 receive less or no irradiation, are less cross linked and hence are free to expand to the selected diameter.

In an alternative embodiment shown in FIG. 53b a sizing or restraining member 131 can be disposed over balloon 129 and used to control the maximum inflated diameter 129d of balloon 129 as well as the inflated shape of balloon 129. The sizing member can be coupled to the proximal and distal portions of balloon 129 and can comprise a DACRON sheath or other collapsible yet substantially non-compliant material known in the biomedical material arts including polyesters, PET and the like.

In various methods of use, expandable balloon 129 can be expanded in diameter (using an inflation device described herein) in incremental amounts for the use of compliant material such as silicone or for non compliant materials expandable balloon is expanded to final set diameter preselected by the physician depending upon the size of the tissue mass 5" or desired ablation volume 5av. To facilitate selection of different diameter balloons, in an embodiment the expandable balloon can be detachably coupled to the distal portion 112dp of shaft 112

Expandable balloon 129 can be expanded using any number of inflation devices 133 and pressure sources known in the art including a automated pumps and syringes pumps with coupled pressure gauges, including screw type syringe pumps (handheld and automated) and computer controlled inflation devices that automatically adjust the pressure to produce a selected diameter using coupled position and sizing sensors. The balloon can be inflated by means of an inflation lumen 112l in shaft 112 which is coupled to balloon 129. The balloon can also be configured to receive a liquid media including a radio-opaque contrast solution known in the art such that the physician can observe the amount of expansion under fluoroscopy or other imaging modality known in the art. In a related embodiment balloon 120 can be configured to receive an echogenic solution such that balloon can visible under ultrasonagraphy.

In use, expandable balloon device 129 provides the advantage to the physician of expansion device that can be readily advanced through endoscopic and other minimally invasive introducing devices and at the same time achieve a selectable and controlled size and shape for the pattern of deployed electrodes 118 such that this pattern is matched to the size of the desired ablation volume 5$av$ to treat a selected tumor mass 5". More importantly, use of expandable balloon 129 in various embodiments enables the creation of progressively larger ablation volumes simply by expanding balloon 129 and subsequently deploying the electrode and delivering ablative energy without having to reposition apparatus 110. This reduces both procedure time and reduces the risks of contamination of healthy tissue with cancerous cells from a tumor mass 5' by unnecessary movement of the apparatus 110 at the treatment site.

Figure 54:
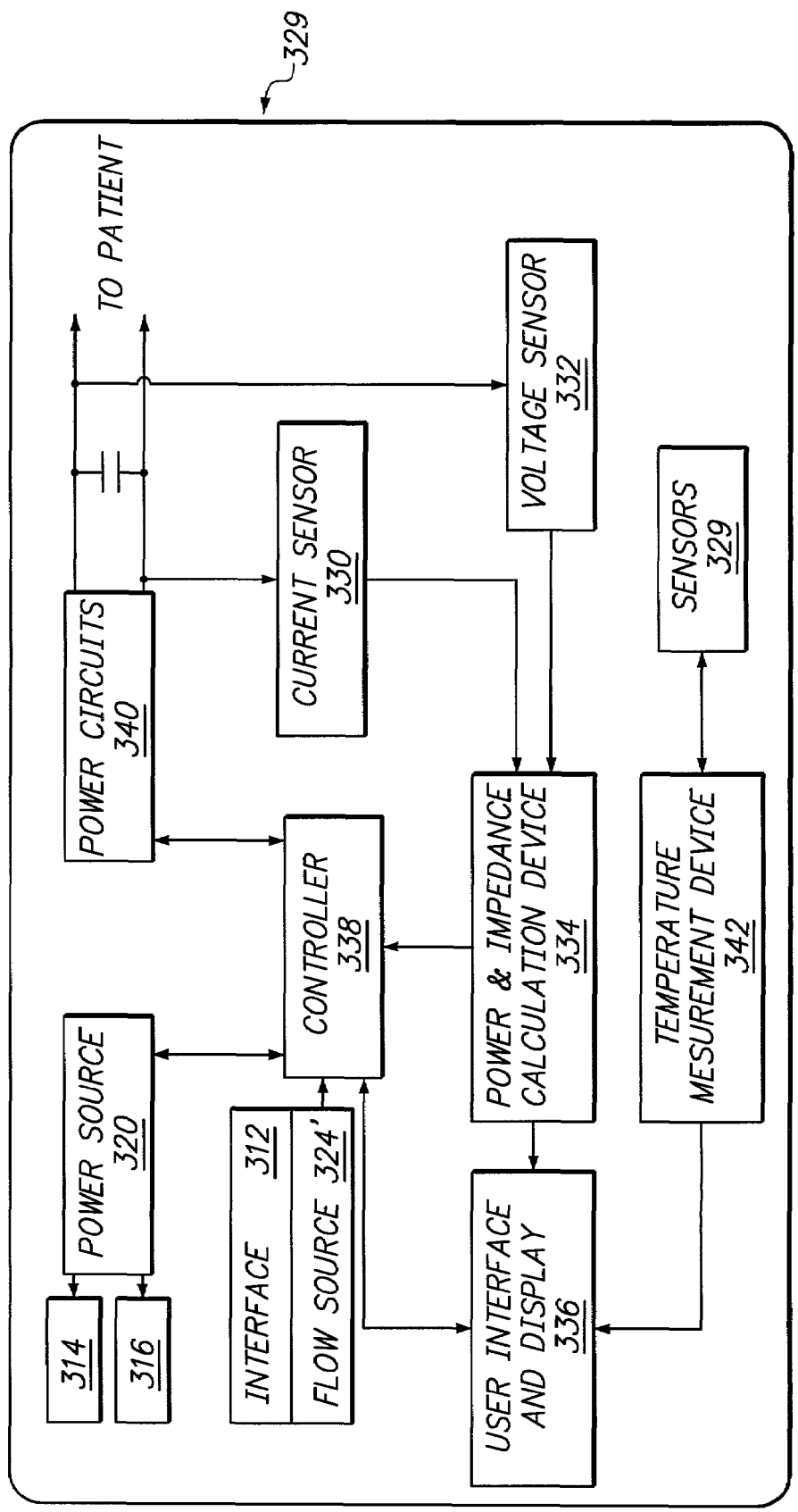
FIG. 54 is a block diagram illustrating a controller, power source, power circuits and other electronic components used with an embodiment of a control system other embodiments of the invention.
Figure 55:
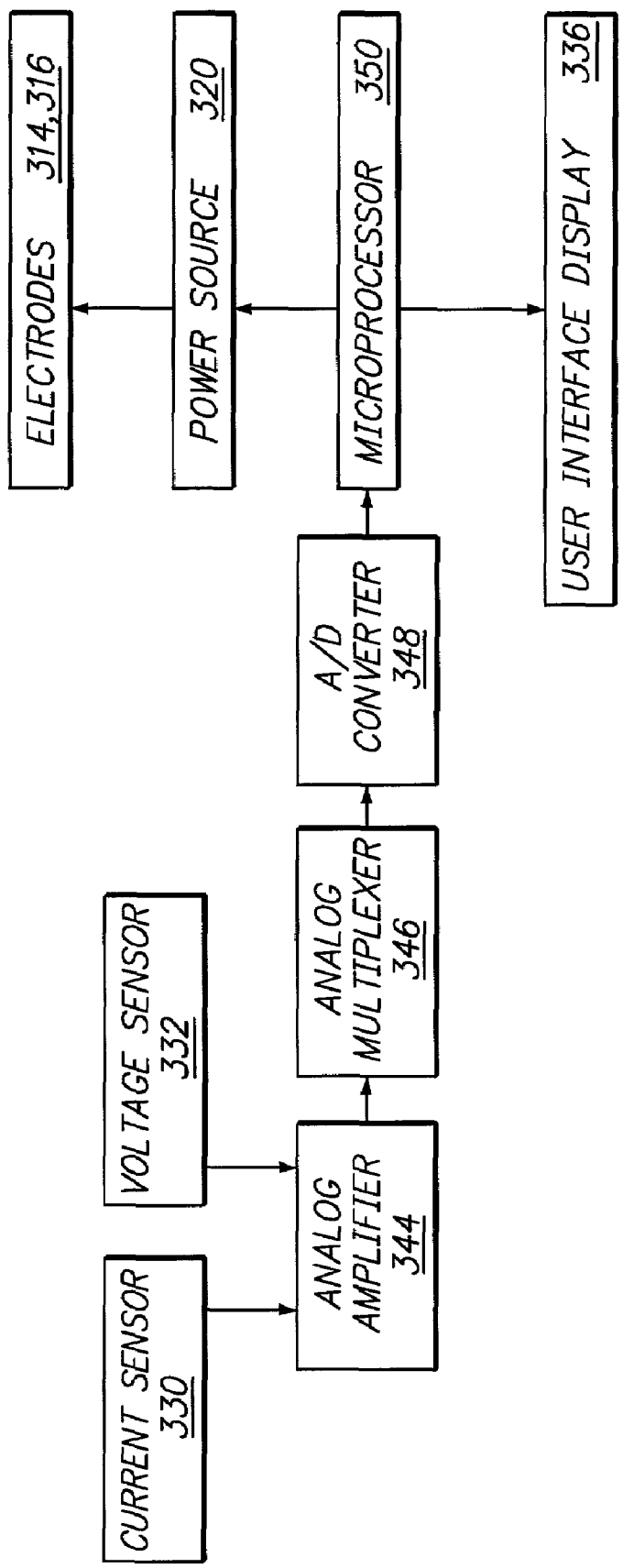
FIG. 55 is a block diagram illustrating an analog amplifier, analog multiplexer and microprocessor used with an embodiment of a control system other embodiments of the invention.

The following discussion pertains particularly to the use of an RF energy source and surface treatment apparatus 10 or 110 with control systems including feedback control systems, computer and microprocessor based control systems. Referring now to FIGS. 54 and 55, in various embodiments a feedback control system 329 can be connected to energy source 320, sensors 324 and energy delivery devices 314 and 316. For purposes of this discussion, energy delivery devices 314 and 316 will now be referred to as RF electrodes or antennas 314 and 316 and energy source 320 will now be an RF energy source. However it will be appreciated that all other energy delivery devices and sources discussed herein are equally applicable and devices similar to those associated with surface treatment ablation apparatus 10 can be utilized with laser optical fibers, microwave devices and the like. The impedance or temperature of the tissue, or of RF electrodes 314 and 316 is monitored, and the output power of energy source 320 adjusted accordingly. The physician can, if desired, override the closed or open loop system.

In an embodiment, feedback control system 329 receives temperature or impedance data from sensors 324 and the amount of electromagnetic energy received by energy delivery devices 314 and 316 is modified from an initial setting of ablation energy output, ablation time, temperature, and current density (the "Four Parameters"). Feedback control system 329 can automatically change any of the Four Parameters individually or in combination. Feedback control system 329 can detect impedance or temperature and change any of the Four Parameters. Feedback control system 329 can include a multiplexer to multiplex different energy delivery devices/ electrodes, a temperature detection circuit that provides a control signal representative of temperature or impedance detected at one or more sensors 324. A microprocessor 339 can be connected to the temperature control circuit.

The user of apparatus 10 can input an impedance value that corresponds to a setting position located at apparatus 10. Based on this value, along with measured impedance values, feedback control system 329 determines an optimal power and time need in the delivery of RF energy. Temperature is also sensed for monitoring and feedback purposes. Temperature can be maintained to a certain level by having feedback control system 329 adjust the power output automatically to maintain that level.

In another embodiment, feedback control system 329 determines an optimal power and time for a baseline setting. Ablation volumes or lesions are formed at the baseline first. Larger lesions can be obtained by extending the time of ablation after a center core is formed at the baseline. The completion of lesion creation can be checked by advancing energy delivery device 316 from distal end 16 of introducer 12 to a position corresponding to a desired lesion size and monitoring the temperature at the periphery of the lesion such that a temperature sufficient to produce a lesion is attained.

The closed loop system 329 can also utilize a controller 338 to monitor the temperature, adjust the RF power, analyze the result, refeed the result, and then modulate the power. More specifically, controller 338 governs the power levels, cycles, and duration that the RF energy is distributed to electrodes 314 and 316 to achieve and maintain power levels appropriate to achieve the desired treatment objectives and clinical endpoints. Controller 338 can also in tandem govern the delivery of electrolytic, cooling fluid and, the removal of aspirated tissue. Controller 338 can also in tandem monitor for excessive impedance at the tissue site and switch power sources 320 and electrodes 314 and 316 from a monopolar mode to a bipolar mode or switch from use of ground pad electrode 18$g$ to conductive portions 14 con of tissue contact surface 14. Controller 338 can be integral to or otherwise coupled to power source 320. The controller 338 can be also be coupled to an input/output (PO) device such as a keyboard, touchpad, PDA, microphone (coupled to speech recognition software resident in controller 338 or other computer) and the like.

Referring now to FIG. 54, all or portions of feedback control system 329 are illustrated. Current delivered through RF electrodes 314 and 316 (also called primary and secondary RF electrodes/antennas 314 and 316) is measured by a current sensor 330. Voltage is measured by voltage sensor 332. Impedance and power are then calculated at power and impedance calculation device 334. These values can then be displayed at a user interface and display 336. Signals representative of power and impedance values are received by controller 338 which can be a microprocessor 338.

A control signal is generated by controller 338 that is proportional to the difference between an actual measured value, and a desired value. The control signal is used by power circuits 340 to adjust the power output in an appropriate amount in order to maintain the desired power delivered at the respective primary and/or secondary antennas 314 and 316. In a similar manner, temperatures detected at sensors 324 provide feedback for maintaining a selected power. The actual temperatures are measured at temperature measurement device 342, and the temperatures are displayed at user interface and display 336. A control signal is generated by controller 338 that is proportional to the difference between an actual measured temperature, and a desired temperature. The control signal is used by power circuits 340 to adjust the power output in an appropriate amount in order to maintain the desired temperature delivered at the respective sensor 324. A multiplexer 346 can be included to measure current, voltage and temperature, at the numerous sensors 324 as will deliver and distribute energy between primary electrodes 314 and secondary electrodes 316.

Controller 338 can be a digital or analog controller, or a computer with embedded, resident or otherwise coupled software. In an embodiment, controller 338 can be a Pentium® family microprocessor manufacture by the Intel® Corporation (Santa Clara, Calif.). When controller 338 is a computer it can include a CPU coupled through a system bus. On this system can be a keyboard, a disk drive, or other non-volatile memory systems, a display, and other peripherals, as are known in the art. Also coupled to the bus are a program memory and a data memory. In various embodiments controller 338 can be coupled to imaging systems, including but not limited to ultrasound, CT scanners (including fast CT scanners such as those manufacture by the Imatron Corporation (South San Francisco, Calif.), X-ray, MRI, mammographic X-ray and the like. Further, direct visualization and tactile imaging can be utilized.

User interface and display 336 can include operator controls and a display. In an embodiment, user interface 336 can be a PDA device known in the art such as a Palm® family computer manufactured by Palm® Computing (Santa Clara, Calif.). Interface 336 can be configured to allow the user to input control and processing variables, to enable the controller to generate appropriate command signals. Interface 336 can also receives real time processing feedback information from one or more sensors 324 for processing by controller 338, to govern the delivery and distribution of energy, fluid etc.

The output of current sensor 330 and voltage sensor 332 is used by controller 338 to maintain a selected power level at primary and secondary antennas 314 and 316. The amount of RF energy delivered controls the amount of power. A profile of power delivered can be incorporated in controller 338, and a preset amount of energy to be delivered can also be profiled.

Circuitry, software and feedback to controller 338 result in process control, and the maintenance of the selected power, and are used to change, (i) the selected power, including RF, microwave, laser and the like; (ii) the duty cycle (on-off and wattage); (iii) bipolar or monopolar energy delivery; and (iv) infusion medium delivery, including flow rate and pressure. These process variables are controlled and varied, while maintaining the desired delivery of power independent of changes in voltage or current, based on temperatures monitored at sensors 324. A controller 338 can be incorporated into feedback control system 329 to switch power on and off, as well as modulate the power. Also, with the use of sensor 324 and feedback control system 329, tissue adjacent to RF electrodes 314 and 316 can be maintained at a desired temperature for a selected period of time without causing a shut down of the power circuit to electrode 314 due to the development of excessive electrical impedance at electrode 314 or adjacent tissue. In related embodiment control system 329 can be used to determine and control the deployment position and penetration depth of electrode 314.

Referring now to FIG. 55, current sensor 330 and voltage sensor 332 are connected to the input of an analog amplifier 344. Analog amplifier 344 can be a conventional differential amplifier circuit for use with sensors 324. The output of analog amplifier 344 is sequentially connected by an analog multiplexer 346 to the input of A/D converter 348. The output of analog amplifier 344 is a voltage which represents the respective sensed temperatures. Digitized amplifier output voltages are supplied by A/D converter 348 to a microprocessor 350. Microprocessor 350 may be Model No. 68HCII available from Motorola. However, it will be appreciated that any suitable microprocessor or general purpose digital or analog computer can be used to calculate impedance or temperature.

Microprocessor 350 sequentially receives and stores digital representations of impedance and temperature. Each digital value received by microprocessor 350 corresponds to different temperatures and impedances. Calculated power and impedance values can be indicated on user interface and display 336. Alternatively, or in addition to the numerical indication of power or impedance, calculated impedance and power values can be compared by microprocessor 350 with power and impedance limits. When the values exceed predetermined power or impedance values, a warning can be given on user interface and display 336, and additionally, the delivery of RF energy can be reduced, modified or interrupted. A control signal from microprocessor 350 can modify the power level supplied by energy source 320 to RF electrodes 314 and 316. In a similar manner, temperatures and positions detected at sensors 324 provide feedback for determining the extent and rate of (i) tissue hyperthermia; (ii) cell necrosis or ablation; and (iii) when a boundary of desired cell necrosis or ablation has reached the physical location of sensors 324.

CONCLUSION

It will be appreciated that the applicants have provided a novel and useful apparatus and method for the treatment of tumors using surgical or minimally invasive methods. The foregoing description of a preferred embodiment of the invention has been presented for purposes of illustration and description. It is not intended to be exhaustive or to limit the invention to the precise forms disclosed. Embodiments of the invention can be configured for the treatment of tumor and tissue masses at or beneath a tissue surface in a number of organs including but no limited to the liver, breast, bone and lung. However, embodiments of the invention are applicable to other organs and tissue as well. Obviously, many modifications and variations will be apparent to practitioners skilled in this art. Further, elements from one embodiment can be readily recombined with elements from one or more other embodiments. Such combinations can form a number of embodiments within the scope of the invention. It is intended that the scope of the invention be defined by the following claims and their equivalents.

What is claimed is:

1. A tissue surface treatment apparatus, comprising:
a housing having a proximal end and, a distal end including a tissue contacting surface having a plurality of apertures thereon, the housing defining an interior therein, wherein at least a portion of the tissue contacting surface is a conductive contact surface;
an energy delivery device positionable in the housing interior, the energy delivery device including a plurality of energy delivery electrodes, each having a tissue penetrating distal end, the plurality of energy delivery electrodes configured to be advanced from the housing interior through the apertures and deployed into a target tissue site, the tissue contacting surface and the energy delivery electrodes being configured to define an ablation volume that is at least partly bounded by a tissue surface in contact with the tissue contacting surface of the housing; and
an advancement device coupled to the energy delivery device, the advancement device being configured to selectively advance at least a portion of at least one of the energy delivery electrodes from the housing interior into the target tissue site and withdraw the at least one electrode into the housing interior.

2. The apparatus of claim 1, wherein the at least one of the plurality of electrodes is an RF electrode.

3. The apparatus of claim 1, wherein the advancement device is configured to move reciprocally within the housing.

4. The apparatus of claim 1, wherein the advancement device includes a cam member.

5. The apparatus of claim 1, wherein at least a portion of the tissue contacting surface includes an insulative layer or coating.

6. A tissue surface treatment apparatus of claim 1 further comprising:
a multiplexing device coupled to at least one of the plurality of electrodes, a power supply coupled to the at least one electrode or a ground pad electrode coupled to a power supply.

7. A tissue surface treatment apparatus of claim 1, wherein at least a portion of the tissue contact surface has a lubricous coating.

8. The apparatus of claim 7, wherein the lubricous coating is one of a non-stick coating, a hydrophobic coating, a polymer coating, a fluoro-polymer coating, or a silicone coating.

9. The apparatus of claim 7, wherein the lubricous coating is configured to reduce a tissue adhesion to the portion of the tissue contacting surface.

10. The tissue surface treatment apparatus of claim 1, further comprising:
at least one stop coupled to one of the housing or the advancement device, wherein the stop is configured for controlling a depth of tissue penetration of at least one of the plurality of electrodes.

11. The apparatus of claim 10, wherein the stop is positionable.

12. The apparatus of claim 10, wherein the stop comprises one of an indexing device or an indexing mechanism.

13. The apparatus of claim 1, wherein at least one of the plurality of electrodes is configured for linear movement with respect to a longitudinal axis of the advancement device.

14. The tissue surface treatment apparatus of claim 1, further comprising an insulator positioned in a surrounding relationship to the at least one electrode.

15. The apparatus of claim 14, wherein the insulator is slidably positionable over the at least one electrode to produce a selectable energy delivery surface.

16. The tissue surface treatment apparatus of claim 1, further comprising:
a sensor coupled to at least one of the housing, the tissue contact surface, the energy delivery device, at least one of the plurality of electrodes, or the advancement member.

17. The apparatus of claim 16, wherein the sensor is a thermal sensor, a thermocouple, a pressure sensor, a force sensor, a strain gauge, a positional sensor, an LVDT, an optical sensor, a current sensor, voltage sensor or a pH sensor.

18. The apparatus of claim 16, wherein the sensor is configured to sense one of an electrode position, an electrode deployment depth or a fully withdrawn position of the electrode.

19. The apparatus of claim 1, further comprising: one or more feedback control resources.

20. The apparatus of claim 19, wherein the feedback control resources includes at least one of a microprocessor, a controller, a software module, a software program set forth in a tangible media, a power control ciruit, a voltage and current monitor, a user interface or a display.

21. The apparatus of claim 19, wherein the feedback control resources are configured to control process variables to reduce one of a tissue desiccation in proximity to the energy delivery device or an impedance rise.

22. The apparatus of claim 21, wherein the process variables include at least one of a power level, a duty cycle, an energy delivery, an RF energy delivery, or a rate of RF energy delivery to the tissue site.

23. A tissue surface treatment apparatus, comprising: a housing means having a proximal end, and a distal end including a substantially planar tissue contacting means having a plurality of apertures each positioned in the tissue contacting means, the housing means defining an interior therein, wherein at least a portion of the tissue contacting means is a conductive contact surface; an energy delivery device positionable in the housing means interior, the energy delivery device including a plurality of energy delivery means, each having a tissue penetrating distal end, the plurality of energy delivery means configured to be advanced from the housing means interior through the apertures into a target tissue site, the tissue contacting means and the energy delivery means being configured to define an ablation volume at least partly bounded by a tissue surface; an advancement means coupled to the plurality of energy delivery means, the advancement means configured to sectively advance at least one of the plurality of energy delivery means from the housing means interior into the target tissue site and withdraw the plurality of electrode means into the housing means interior.

* * * * *